US007348406B2

(12) United States Patent
Erickson et al.

(10) Patent No.: US 7,348,406 B2
(45) Date of Patent: Mar. 25, 2008

(54) METABOLIC GENE POLYNUCLEOTIDES AND POLYPEPTIDES AND USES THEREOF

(75) Inventors: Mary Ruth Erickson, San Diego, CA (US); Barbara A. Chicca, San Diego, CA (US); Bernard Bihain, Cancale (FR); Hiroaki Tanaka, Antony (FR)

(73) Assignee: Serono Genetics Institute S.A., Evry (FR)

( * ) Notice: Subject to any disclaimer, the term of this patent is extended or adjusted under 35 U.S.C. 154(b) by 615 days.

(21) Appl. No.: 10/466,376

(22) PCT Filed: Jan. 15, 2002

(86) PCT No.: PCT/IB02/01215

§ 371 (c)(1),
(2), (4) Date: Feb. 5, 2004

(87) PCT Pub. No.: WO02/055694

PCT Pub. Date: Jul. 18, 2002

(65) Prior Publication Data

US 2006/0247160 A1   Nov. 2, 2006

Related U.S. Application Data

(60) Provisional application No. 60/262,235, filed on Jan. 16, 2001.

(51) Int. Cl.
*C07K 14/00* (2006.01)
*C07K 16/00* (2006.01)
*A61K 38/00* (2006.01)

(52) U.S. Cl. ............... 530/350; 530/388.2; 514/12
(58) Field of Classification Search ............... 530/350, 530/388.2; 514/12
See application file for complete search history.

(56) References Cited

U.S. PATENT DOCUMENTS

| 5,336,603 A | 8/1994 | Capon et al. |
| 5,480,981 A | 1/1996 | Goodwin et al. |
| 5,541,087 A | 7/1996 | Lo et al. |
| 5,670,625 A | 9/1997 | Lyman et al. |
| 5,738,844 A | 4/1998 | Beckmann et al. |
| 6,444,425 B1 | 9/2002 | Reed et al. |
| 6,759,508 B2 | 7/2004 | Lodes et al. |

FOREIGN PATENT DOCUMENTS

| WO | WO 99/04000 | 1/1999 |
| WO | WO 99/38973 | 8/1999 |

OTHER PUBLICATIONS

Database: EMBL: Accession No. P23435; Created Nov. 1, 1991, Description: Cerebellin precursor (Precerebellin) XP-002209555.
Database: EMBL: Accession No. Q96JF4; Created Dec. 1, 2001, Description: Hypothetical protein KIAA1873 (Fragment) XP-002209556.
Database EMBL: Accession No. Q15848; Created Nov. 1, 1997, Description: Adiponectin precursor (30 kDa adipocyte complement-related protein) (ACRP30) (Adipose most abundant gene transcript 1) (apM-1) (Gelatin-binding protein) XP-002208112.
Saito et al. "Organization of the gene for gelatin-binding protein (GBP28)" *Gene* 1999, vol. 229, pp. 67-73.
Maeda et al. "cDNA Cloning and Expression of a Novel Adipose Specific Collagen-like Factor, apM1 (Adipose Most Abundant Gene Transcript 1)" *Biochemical and Biophysical Research Communications* 1996, vol. 221, pp. 286-289. XP 000612064.
Schäffler et al. "The Human apM-1, an Adipocyte-Specific Gene Linked to the Family of TNF's and to Genes Expressed in Activated T Cells, Is Mapped to Chromosome 1q21.3-q23, a Susceptibility Locus Identified for Familial Combined Hyperlipidaemia (FCH)" *Biochemical and Biophysical Research Communications* 1999, vol. 260, pp. 416-425. XP-000867718.
Barsh, G.S. et al. "Genetics of body-weight regulation", *Nature*, Apr. 6, 2000, pp. 644-651, vol. 404.

*Primary Examiner*—Jon Weber
*Assistant Examiner*—Rita Mitra
(74) *Attorney, Agent, or Firm*—Saliwanchik, Lloyd & Saliwanchik

(57) ABSTRACT

The present invention relates to the field of metabolic research. Metabolic disorders, such as obesity, are a public health problem that is serious and widespread. GMG-3, GMG-4, Cluster 1, GMG-6A, or GMG-6B polypeptides have been identified that are beneficial in the treatment of metabolic disorders. These compounds should be effective for reducing body mass and for treating metabolic-related diseases and disorders. These metabolic-related diseases and disorders include hyperlipidemias, atherosclerosis, diabetes, and hypertension.

15 Claims, No Drawings

SEQUENCE LISTING

```
<160> NUMBER OF SEQ ID NOS: 12

<210> SEQ ID NO 1
<211> LENGTH: 2257
<212> TYPE: DNA
<213> ORGANISM: Homo sapiens
<220> FEATURE:
<221> NAME/KEY: CDS
<222> LOCATION: (37)...(2169)

<400> SEQUENCE: 1
ttggccaagg aaagaaagt accactggag gaagaa atg cta ata caa tca gag      54
                                      Met Leu Ile Gln Ser Glu
                                       1               5 aaa aaa aca caa tta tcg aag act gaa tct gtc aaa gag tca gag tct    102
Lys Lys Thr Gln Leu Ser Lys Thr Glu Ser Val Lys Glu Ser Glu Ser
             10                  15                  20 cta atg gaa ttt gcc cag cca gag ata caa cca caa gag ttt ctt aac    150
Leu Met Glu Phe Ala Gln Pro Glu Ile Gln Pro Gln Glu Phe Leu Asn
         25                  30                  35 aga cgc tat atg aca gaa gta gat tat tca aac aaa caa ggc gaa gag    198
Arg Arg Tyr Met Thr Glu Val Asp Tyr Ser Asn Lys Gln Gly Glu Glu
     40                  45                  50 caa cct tgg gaa gca gat tat gct aga aaa cca aat ctc cca aaa cgt    246
Gln Pro Trp Glu Ala Asp Tyr Ala Arg Lys Pro Asn Leu Pro Lys Arg
 55                  60                  65                  70 tgg gat atg ctt act gaa cca gat ggt caa gag aag aaa cag gag tcc    294
Trp Asp Met Leu Thr Glu Pro Asp Gly Gln Glu Lys Lys Gln Glu Ser
                 75                  80                  85 ttt aag tcc tgg gag gct tct ggt aag cac cag gag gta tcc aag cct    342
Phe Lys Ser Trp Glu Ala Ser Gly Lys His Gln Glu Val Ser Lys Pro
             90                  95                 100 gca gtt tcc tta gaa cag agg aaa caa gac acc tca aaa ctc agg tct    390
Ala Val Ser Leu Glu Gln Arg Lys Gln Asp Thr Ser Lys Leu Arg Ser
        105                 110                 115 act ctg ccg gaa gag cag aag aag cag gag atc tcc aaa tcc aag cca    438
Thr Leu Pro Glu Glu Gln Lys Lys Gln Glu Ile Ser Lys Ser Lys Pro
    120                 125                 130
```

| | | |
|---|---|---|
| tct cct agc cag tgg aag caa gat aca cct aaa tcc aaa gca ggg tat<br>Ser Pro Ser Gln Trp Lys Gln Asp Thr Pro Lys Ser Lys Ala Gly Tyr<br>135                   140                     145                   150 | 486 |

```
tct cct agc cag tgg aag caa gat aca cct aaa tcc aaa gca ggg tat      486
Ser Pro Ser Gln Trp Lys Gln Asp Thr Pro Lys Ser Lys Ala Gly Tyr
135                 140                 145                 150 gtt caa gag gaa caa aag aaa cag gag aca cca aag ctg tgg cca gtt      534
Val Gln Glu Glu Gln Lys Lys Gln Glu Thr Pro Lys Leu Trp Pro Val
                155                 160                 165 cag ctg cag aaa gaa caa gat cca aag aag caa act cca aag tct tgg      582
Gln Leu Gln Lys Glu Gln Asp Pro Lys Lys Gln Thr Pro Lys Ser Trp
        170                 175                 180 aca cct tcc gtg cag agc gaa cag aac acc acc aag tca tgg acc act      630
Thr Pro Ser Val Gln Ser Glu Gln Asn Thr Thr Lys Ser Trp Thr Thr
    185                 190                 195 ccc atg tgt gaa gaa cag gat tca aaa cag cca gag act cca aaa tcc      678
Pro Met Cys Glu Glu Gln Asp Ser Lys Gln Pro Glu Thr Pro Lys Ser
200                 205                 210 tgg gaa aac aat gtt gag agt caa aaa cac tct tta aca tca cag tca      726
Trp Glu Asn Asn Val Glu Ser Gln Lys His Ser Leu Thr Ser Gln Ser
215                 220                 225                 230 cag att tct cca aag tcc tgg gga gta gct aca gca agc ctc ata cca      774
Gln Ile Ser Pro Lys Ser Trp Gly Val Ala Thr Ala Ser Leu Ile Pro
                235                 240                 245 aat gac cag ctg ctg ccc agg aag ttg aac aca gaa ccc aaa gat gtg      822
Asn Asp Gln Leu Leu Pro Arg Lys Leu Asn Thr Glu Pro Lys Asp Val
        250                 255                 260 cct aag cct gtg cat cag cct gta ggt tct tcc tct acc ctt ccg aag      870
Pro Lys Pro Val His Gln Pro Val Gly Ser Ser Ser Thr Leu Pro Lys
    265                 270                 275 gat cca gta ttg agg aaa gaa aaa ctg cag gat ctg atg act cag att      918
Asp Pro Val Leu Arg Lys Glu Lys Leu Gln Asp Leu Met Thr Gln Ile
280                 285                 290 caa gga act tgt aac ttt atg caa gag tct gtt ctt gac ttt gac aaa      966
Gln Gly Thr Cys Asn Phe Met Gln Glu Ser Val Leu Asp Phe Asp Lys
295                 300                 305                 310 cct tca agt gca att cca acg tca caa ccg cct tca gct act cca ggt     1014
Pro Ser Ser Ala Ile Pro Thr Ser Gln Pro Pro Ser Ala Thr Pro Gly
                315                 320                 325 agc ccc gta gca tct aaa gaa caa aat ctg tcc agt caa agt gat ttt     1062
Ser Pro Val Ala Ser Lys Glu Gln Asn Leu Ser Ser Gln Ser Asp Phe
        330                 335                 340 ctt caa gag ccg tta cag gta ttt aac gtt aat gca cct ctg cct cca     1110
Leu Gln Glu Pro Leu Gln Val Phe Asn Val Asn Ala Pro Leu Pro Pro
    345                 350                 355 cga aaa gaa caa gaa ata aaa gaa tcc cct tat tca cct ggc tac aat     1158
Arg Lys Glu Gln Glu Ile Lys Glu Ser Pro Tyr Ser Pro Gly Tyr Asn
360                 365                 370 caa agt ttt acc aca gca agt aca caa aca cca ccc cag tgc caa ctg     1206
Gln Ser Phe Thr Thr Ala Ser Thr Gln Thr Pro Pro Gln Cys Gln Leu
375                 380                 385                 390 cca tct ata cat gta gaa caa act gtc cat tct caa gag act gca gca     1254
Pro Ser Ile His Val Glu Gln Thr Val His Ser Gln Glu Thr Ala Ala
                395                 400                 405 aat tat cat cct gat gga act att caa gta agc aat ggt agc ctt gcc     1302
Asn Tyr His Pro Asp Gly Thr Ile Gln Val Ser Asn Gly Ser Leu Ala
        410                 415                 420 ttt tac cca gca cag acg aat gta ttt ccc aga cct act cag cca ttt     1350
Phe Tyr Pro Ala Gln Thr Asn Val Phe Pro Arg Pro Thr Gln Pro Phe
    425                 430                 435 gtc aat agc cgg gga tct gtt aga gga tgt act cgt ggt ggg aga tta     1398
Val Asn Ser Arg Gly Ser Val Arg Gly Cys Thr Arg Gly Gly Arg Leu
```

-continued

```
                  440                 445                 450
ata acc aat tcc tat cgg tcc cct ggt ggt tat aaa ggt ttt gat act        1446
Ile Thr Asn Ser Tyr Arg Ser Pro Gly Gly Tyr Lys Gly Phe Asp Thr
455                 460                 465                 470 tat aga gga ctc cct tca att tcc aat gga aat tat agc cag ctg cag        1494
Tyr Arg Gly Leu Pro Ser Ile Ser Asn Gly Asn Tyr Ser Gln Leu Gln
                475                 480                 485 ttc caa gct aga gag tat tct gga gca cct tat tcc caa agg gat aat        1542
Phe Gln Ala Arg Glu Tyr Ser Gly Ala Pro Tyr Ser Gln Arg Asp Asn
            490                 495                 500 ttc cag cag tgt tat aag cga gga ggg aca tct ggt ggt cca cga gca        1590
Phe Gln Gln Cys Tyr Lys Arg Gly Gly Thr Ser Gly Gly Pro Arg Ala
        505                 510                 515 aat tcg aga gca ggg tgg agt gat tct tct cag gtg agc agc cca gaa        1638
Asn Ser Arg Ala Gly Trp Ser Asp Ser Ser Gln Val Ser Ser Pro Glu
    520                 525                 530 aga gac aac gaa acc ttt aac agt ggt gac tct gga caa gga gac tcc        1686
Arg Asp Asn Glu Thr Phe Asn Ser Gly Asp Ser Gly Gln Gly Asp Ser
535                 540                 545                 550 cgt agc atg acc cct gtg gat gtg cca gtg aca aat cca gca gcc acc        1734
Arg Ser Met Thr Pro Val Asp Val Pro Val Thr Asn Pro Ala Ala Thr
                555                 560                 565 ata ctg cca gta cac gtc tac cct ctg cct cag cag atg cga gtt gcc        1782
Ile Leu Pro Val His Val Tyr Pro Leu Pro Gln Gln Met Arg Val Ala
            570                 575                 580 ttc tca gca gcc aga acc tct aat ctg gcc cct gga act tta gac caa        1830
Phe Ser Ala Ala Arg Thr Ser Asn Leu Ala Pro Gly Thr Leu Asp Gln
        585                 590                 595 cct att gtg ttt gat ctt ctt ctg aac aac tta gga gaa act ttt gat        1878
Pro Ile Val Phe Asp Leu Leu Leu Asn Asn Leu Gly Glu Thr Phe Asp
    600                 605                 610 ctt cag ctt ggt aga ttt aat tgc cca gtg aat ggc act tac gtt ttc        1926
Leu Gln Leu Gly Arg Phe Asn Cys Pro Val Asn Gly Thr Tyr Val Phe
615                 620                 625                 630 att ttt cac atg cta aag ctg gca gtg aat gtg cca ctg tat gtc aac        1974
Ile Phe His Met Leu Lys Leu Ala Val Asn Val Pro Leu Tyr Val Asn
                635                 640                 645 ctc atg aag aat gaa gag gtc ttg gta tca gcc tat gcc aat gat ggt        2022
Leu Met Lys Asn Glu Glu Val Leu Val Ser Ala Tyr Ala Asn Asp Gly
            650                 655                 660 gct cca gac cat gaa act gct agc aat cat gca att ctt cag ctc ttc        2070
Ala Pro Asp His Glu Thr Ala Ser Asn His Ala Ile Leu Gln Leu Phe
        665                 670                 675 cag gga gac cag ata tgg tta cgt ctg cac agg gga gca att tat gga        2118
Gln Gly Asp Gln Ile Trp Leu Arg Leu His Arg Gly Ala Ile Tyr Gly
    680                 685                 690 agt agc tgg aaa tat tct acg ttt tca ggc tat ctt ctt tat caa gat        2166
Ser Ser Trp Lys Tyr Ser Thr Phe Ser Gly Tyr Leu Leu Tyr Gln Asp
695                 700                 705                 710 tga aagtcagtac agtattgaca ataaaaggat ggtgttctaa ttagtgggat             2219
tgaaggaaaa gtagtctttg ccctcatgac tgattgga                              2257
```

<210> SEQ ID NO 2
<211> LENGTH: 710
<212> TYPE: PRT
<213> ORGANISM: Homo sapiens

<400> SEQUENCE: 2

Met Leu Ile Gln Ser Glu Lys Lys Thr Gln Leu Ser Lys Thr Glu Ser

-continued

```
  1               5                   10                  15
Val Lys Glu Ser Glu Ser Leu Met Glu Phe Ala Gln Pro Glu Ile Gln
                20                  25                  30

Pro Gln Glu Phe Leu Asn Arg Arg Tyr Met Thr Glu Val Asp Tyr Ser
                35                  40              45

Asn Lys Gln Gly Glu Glu Gln Pro Trp Glu Ala Asp Tyr Ala Arg Lys
                50                  55                  60

Pro Asn Leu Pro Lys Arg Trp Asp Met Leu Thr Glu Pro Asp Gly Gln
 65                 70                  75                  80

Glu Lys Lys Gln Glu Ser Phe Lys Ser Trp Glu Ala Ser Gly Lys His
                    85                  90                  95

Gln Glu Val Ser Lys Pro Ala Val Ser Leu Glu Gln Arg Lys Gln Asp
                100                 105                 110

Thr Ser Lys Leu Arg Ser Thr Leu Pro Glu Glu Gln Lys Lys Gln Glu
                115                 120                 125

Ile Ser Lys Ser Lys Pro Ser Pro Ser Gln Trp Lys Gln Asp Thr Pro
                130                 135                 140

Lys Ser Lys Ala Gly Tyr Val Gln Glu Glu Gln Lys Lys Gln Glu Thr
145                 150                 155                 160

Pro Lys Leu Trp Pro Val Gln Leu Gln Lys Glu Gln Asp Pro Lys Lys
                165                 170                 175

Gln Thr Pro Lys Ser Trp Thr Pro Ser Val Gln Ser Glu Gln Asn Thr
                180                 185                 190

Thr Lys Ser Trp Thr Thr Pro Met Cys Glu Glu Gln Asp Ser Lys Gln
                195                 200                 205

Pro Glu Thr Pro Lys Ser Trp Glu Asn Asn Val Glu Ser Gln Lys His
                210                 215                 220

Ser Leu Thr Ser Gln Ser Gln Ile Ser Pro Lys Ser Trp Gly Val Ala
225                 230                 235                 240

Thr Ala Ser Leu Ile Pro Asn Asp Gln Leu Leu Pro Arg Lys Leu Asn
                245                 250                 255

Thr Glu Pro Lys Asp Val Pro Lys Pro Val His Gln Pro Val Gly Ser
                260                 265                 270

Ser Ser Thr Leu Pro Lys Asp Pro Val Leu Arg Lys Glu Lys Leu Gln
                275                 280                 285

Asp Leu Met Thr Gln Ile Gln Gly Thr Cys Asn Phe Met Gln Glu Ser
                290                 295                 300

Val Leu Asp Phe Asp Lys Pro Ser Ser Ala Ile Pro Thr Ser Gln Pro
305                 310                 315                 320

Pro Ser Ala Thr Pro Gly Ser Pro Val Ala Ser Lys Glu Gln Asn Leu
                325                 330                 335

Ser Ser Gln Ser Asp Phe Leu Gln Glu Pro Leu Gln Val Phe Asn Val
                340                 345                 350

Asn Ala Pro Leu Pro Pro Arg Lys Glu Gln Glu Ile Lys Glu Ser Pro
                355                 360                 365

Tyr Ser Pro Gly Tyr Asn Gln Ser Phe Thr Thr Ala Ser Thr Gln Thr
                370                 375                 380

Pro Pro Gln Cys Gln Leu Pro Ser Ile His Val Glu Gln Thr Val His
385                 390                 395                 400

Ser Gln Glu Thr Ala Ala Asn Tyr His Pro Asp Gly Thr Ile Gln Val
                405                 410                 415

Ser Asn Gly Ser Leu Ala Phe Tyr Pro Ala Gln Thr Asn Val Phe Pro
                420                 425                 430
```

```
Arg Pro Thr Gln Pro Phe Val Asn Ser Arg Gly Ser Val Arg Gly Cys
        435                 440                 445

Thr Arg Gly Gly Arg Leu Ile Thr Asn Ser Tyr Arg Ser Pro Gly Gly
450                 455                 460

Tyr Lys Gly Phe Asp Thr Tyr Arg Gly Leu Pro Ser Ile Ser Asn Gly
465                 470                 475                 480

Asn Tyr Ser Gln Leu Gln Phe Gln Ala Arg Glu Tyr Ser Gly Ala Pro
                485                 490                 495

Tyr Ser Gln Arg Asp Asn Phe Gln Gln Cys Tyr Lys Arg Gly Gly Thr
            500                 505                 510

Ser Gly Gly Pro Arg Ala Asn Ser Arg Ala Gly Trp Ser Asp Ser Ser
        515                 520                 525

Gln Val Ser Ser Pro Glu Arg Asp Asn Glu Thr Phe Asn Ser Gly Asp
    530                 535                 540

Ser Gly Gln Gly Asp Ser Arg Ser Met Thr Pro Val Asp Val Pro Val
545                 550                 555                 560

Thr Asn Pro Ala Ala Thr Ile Leu Pro Val His Val Tyr Pro Leu Pro
                565                 570                 575

Gln Gln Met Arg Val Ala Phe Ser Ala Ala Arg Thr Ser Asn Leu Ala
            580                 585                 590

Pro Gly Thr Leu Asp Gln Pro Ile Val Phe Asp Leu Leu Leu Asn Asn
        595                 600                 605

Leu Gly Glu Thr Phe Asp Leu Gln Leu Gly Arg Phe Asn Cys Pro Val
    610                 615                 620

Asn Gly Thr Tyr Val Phe Ile Phe His Met Leu Lys Leu Ala Val Asn
625                 630                 635                 640

Val Pro Leu Tyr Val Asn Leu Met Lys Asn Glu Val Leu Val Ser
                645                 650                 655

Ala Tyr Ala Asn Asp Gly Ala Pro Asp His Glu Thr Ala Ser Asn His
            660                 665                 670

Ala Ile Leu Gln Leu Phe Gln Gly Asp Gln Ile Trp Leu Arg Leu His
        675                 680                 685

Arg Gly Ala Ile Tyr Gly Ser Ser Trp Lys Tyr Ser Thr Phe Ser Gly
    690                 695                 700

Tyr Leu Leu Tyr Gln Asp
705                 710

<210> SEQ ID NO 3
<211> LENGTH: 1630
<212> TYPE: DNA
<213> ORGANISM: Homo sapiens
<220> FEATURE:
<221> NAME/KEY: CDS
<222> LOCATION: (37)...(1452)

<400> SEQUENCE: 3
tttgccaagg aaaaggaagt accactggag gaagaa atg cta ata caa tca gag      54
                                       Met Leu Ile Gln Ser Glu
                                         1               5 aaa aaa aca caa tta tcg aag act gaa tct gtc aaa gag tca gag tct     102
Lys Lys Thr Gln Leu Ser Lys Thr Glu Ser Val Lys Glu Ser Glu Ser
             10                  15                  20 cta atg gaa ttt gcc cag cca gag ata caa cca cag gag ttt ctt aac     150
Leu Met Glu Phe Ala Gln Pro Glu Ile Gln Pro Gln Glu Phe Leu Asn
         25                  30                  35 aga cgc tat atg aca gaa gta gat tat tca aac aaa caa ggc gaa gag     198
```

```
                Arg Tyr Met Thr Glu Val Asp Tyr Ser Asn Lys Gln Gly Glu Glu
                 40                  45                  50 caa cct tgg gaa gca gat tat gct aga aaa cca aat ctc cca aaa cgt        246
Gln Pro Trp Glu Ala Asp Tyr Ala Arg Lys Pro Asn Leu Pro Lys Arg
 55                  60                  65                  70 tgg gat atg ctt act gaa cca gat ggt caa gag aag aaa cag gag tcc        294
Trp Asp Met Leu Thr Glu Pro Asp Gly Gln Glu Lys Lys Gln Glu Ser
                 75                  80                  85 ttt aag tcc tgg gag gct tct ggt aag cac cag gag gta tcc aag cct        342
Phe Lys Ser Trp Glu Ala Ser Gly Lys His Gln Glu Val Ser Lys Pro
                 90                  95                 100 gca gtt tcc tta gaa cag agg aaa caa gac acc tca aaa ctc agg tct        390
Ala Val Ser Leu Glu Gln Arg Lys Gln Asp Thr Ser Lys Leu Arg Ser
                105                 110                 115 act ctg ccg gaa gag cag aag aag cag gag atc tcc aaa tcc aag cca        438
Thr Leu Pro Glu Glu Gln Lys Lys Gln Glu Ile Ser Lys Ser Lys Pro
                120                 125                 130 tct cct agc cag tgg aag caa gat aca cct aaa tcc aaa gca ggg tat        486
Ser Pro Ser Gln Trp Lys Gln Asp Thr Pro Lys Ser Lys Ala Gly Tyr
135                 140                 145                 150 gtt caa gag gaa caa aag aaa cag gag aca cca aag ctg tgg cca gtt        534
Val Gln Glu Glu Gln Lys Lys Gln Glu Thr Pro Lys Leu Trp Pro Val
                155                 160                 165 cag ctg cag aaa gag caa gat cca aag aag caa act cca aag tct tgg        582
Gln Leu Gln Lys Glu Gln Asp Pro Lys Lys Gln Thr Pro Lys Ser Trp
                170                 175                 180 aca cct tcc gtg cag agc gaa cag aac acc acc aag tca tgg acc act        630
Thr Pro Ser Val Gln Ser Glu Gln Asn Thr Thr Lys Ser Trp Thr Thr
                185                 190                 195 ccc atg tgt gaa gaa cag gat tca aaa cag cca gag act cca aaa tcc        678
Pro Met Cys Glu Glu Gln Asp Ser Lys Gln Pro Glu Thr Pro Lys Ser
                200                 205                 210 tgg gaa aac aat gtt gag agt caa aaa cac tct tta aca tca cag tca        726
Trp Glu Asn Asn Val Glu Ser Gln Lys His Ser Leu Thr Ser Gln Ser
215                 220                 225                 230 cag att tct cca aag tcc tgg gga gta gct aca gca agc ctc ata cca        774
Gln Ile Ser Pro Lys Ser Trp Gly Val Ala Thr Ala Ser Leu Ile Pro
                235                 240                 245 aat gac cag ctg ctg ccc agg aag ttg aac aca gaa ccc aaa gat gtg        822
Asn Asp Gln Leu Leu Pro Arg Lys Leu Asn Thr Glu Pro Lys Asp Val
                250                 255                 260 cct aag cct gtg cat cag cct gta ggt tct tcc tct acc ctt ccg aag        870
Pro Lys Pro Val His Gln Pro Val Gly Ser Ser Ser Thr Leu Pro Lys
                265                 270                 275 gat cca gta ttg agg aaa gaa aaa ctg cag gat ctg atg act cag att        918
Asp Pro Val Leu Arg Lys Glu Lys Leu Gln Asp Leu Met Thr Gln Ile
280                 285                 290 caa gga act tgt aac ttt atg caa gag tct gtt ctt gac ttt gac aaa        966
Gln Gly Thr Cys Asn Phe Met Gln Glu Ser Val Leu Asp Phe Asp Lys
295                 300                 305                 310 cct tca agt gca att cca acg tca caa ccg cct tca gct act cca ggt       1014
Pro Ser Ser Ala Ile Pro Thr Ser Gln Pro Pro Ser Ala Thr Pro Gly
                315                 320                 325 agc ccc gta gca tct aaa gaa caa aat ctg tcc agt caa agt gat ttt       1062
Ser Pro Val Ala Ser Lys Glu Gln Asn Leu Ser Ser Gln Ser Asp Phe
                330                 335                 340 ctt caa gag ccg tta cag gct act tct tct cca gtt act tgt agc tca       1110
Leu Gln Glu Pro Leu Gln Ala Thr Ser Ser Pro Val Thr Cys Ser Ser
                345                 350                 355
```

-continued

```
aat gct tgc ttg gtt act acc gat cag gct tct tct gga tct gaa aca      1158
Asn Ala Cys Leu Val Thr Thr Asp Gln Ala Ser Ser Gly Ser Glu Thr
360                 365                 370 gag ttt atg acc tca gag act cct gag gca gca att ccc cca ggc aag      1206
Glu Phe Met Thr Ser Glu Thr Pro Glu Ala Ala Ile Pro Pro Gly Lys
375                 380                 385                 390 caa ccg tct tca cta gct tct cca aat cct ccc atg gca aag ggc tct      1254
Gln Pro Ser Ser Leu Ala Ser Pro Asn Pro Pro Met Ala Lys Gly Ser
            395                 400                 405 gaa cag ggc ttc cag tca cct cca gca agt agt agt tca gta acc att      1302
Glu Gln Gly Phe Gln Ser Pro Pro Ala Ser Ser Ser Ser Val Thr Ile
        410                 415                 420 aac aca gca ccc ttt caa gcc atg cag aca gta ttt aac gtt aat gca      1350
Asn Thr Ala Pro Phe Gln Ala Met Gln Thr Val Phe Asn Val Asn Ala
    425                 430                 435 cct ctg cct cca cga aaa gaa caa gaa ata aaa gaa tcc cct tat tca      1398
Pro Leu Pro Pro Arg Lys Glu Gln Glu Ile Lys Glu Ser Pro Tyr Ser
440                 445                 450 cct ggc tac aat caa agt ctt acc aca gca agt aca caa aca cca ccc      1446
Pro Gly Tyr Asn Gln Ser Leu Thr Thr Ala Ser Thr Gln Thr Pro Pro
455                 460                 465                 470 cag tga atgtgccact gtaacgtctg cacaggggag caatttatgg aagtagctgg       1502
Gln * aaatattcta cgttttcagg ctatcttctt tatcaagatt gaaagtcagt acagtattga    1562
caataaaagg atggtgttct aattagtggg attgaaggaa aagtagtctt tgccctcatg    1622
actgataa                                                             1630

<210> SEQ ID NO 4
<211> LENGTH: 471
<212> TYPE: PRT
<213> ORGANISM: Homo sapiens

<400> SEQUENCE: 4

Met Leu Ile Gln Ser Glu Lys Lys Thr Gln Leu Ser Lys Thr Glu Ser
1               5                   10                  15

Val Lys Glu Ser Glu Ser Leu Met Glu Phe Ala Gln Pro Glu Ile Gln
            20                  25                  30

Pro Gln Glu Phe Leu Asn Arg Arg Tyr Met Thr Glu Val Asp Tyr Ser
        35                  40                  45

Asn Lys Gln Gly Glu Glu Gln Pro Trp Glu Ala Asp Tyr Ala Arg Lys
    50                  55                  60

Pro Asn Leu Pro Lys Arg Trp Asp Met Leu Thr Glu Pro Asp Gly Gln
65                  70                  75                  80

Glu Lys Lys Gln Glu Ser Phe Lys Ser Trp Glu Ala Ser Gly Lys His
                85                  90                  95

Gln Glu Val Ser Lys Pro Ala Val Ser Leu Glu Gln Arg Lys Gln Asp
            100                 105                 110

Thr Ser Lys Leu Arg Ser Thr Leu Pro Glu Glu Gln Lys Lys Gln Glu
        115                 120                 125

Ile Ser Lys Ser Lys Pro Ser Pro Ser Gln Trp Lys Gln Asp Thr Pro
    130                 135                 140

Lys Ser Lys Ala Gly Tyr Val Gln Glu Glu Lys Lys Gln Glu Thr
145                 150                 155                 160

Pro Lys Leu Trp Pro Val Gln Leu Gln Lys Glu Gln Asp Pro Lys Lys
                165                 170                 175

Gln Thr Pro Lys Ser Trp Thr Pro Ser Val Gln Ser Glu Gln Asn Thr
```

-continued

```
                180                 185                 190
Thr Lys Ser Trp Thr Thr Pro Met Cys Glu Glu Gln Asp Ser Lys Gln
            195                 200                 205

Pro Glu Thr Pro Lys Ser Trp Glu Asn Asn Val Glu Ser Gln Lys His
        210                 215                 220

Ser Leu Thr Ser Gln Ser Gln Ile Ser Pro Lys Ser Trp Gly Val Ala
225                 230                 235                 240

Thr Ala Ser Leu Ile Pro Asn Asp Gln Leu Leu Pro Arg Lys Leu Asn
                245                 250                 255

Thr Glu Pro Lys Asp Val Pro Lys Pro Val His Gln Pro Val Gly Ser
            260                 265                 270

Ser Ser Thr Leu Pro Lys Asp Pro Val Leu Arg Lys Glu Lys Leu Gln
        275                 280                 285

Asp Leu Met Thr Gln Ile Gln Gly Thr Cys Asn Phe Met Gln Glu Ser
290                 295                 300

Val Leu Asp Phe Asp Lys Pro Ser Ser Ala Ile Pro Thr Ser Gln Pro
305                 310                 315                 320

Pro Ser Ala Thr Pro Gly Ser Pro Val Ala Ser Lys Glu Gln Asn Leu
                325                 330                 335

Ser Ser Gln Ser Asp Phe Leu Gln Glu Pro Leu Gln Ala Thr Ser Ser
            340                 345                 350

Pro Val Thr Cys Ser Ser Asn Ala Cys Leu Val Thr Thr Asp Gln Ala
        355                 360                 365

Ser Ser Gly Ser Glu Thr Glu Phe Met Thr Ser Glu Thr Pro Glu Ala
370                 375                 380

Ala Ile Pro Pro Gly Lys Gln Pro Ser Ser Leu Ala Ser Pro Asn Pro
385                 390                 395                 400

Pro Met Ala Lys Gly Ser Glu Gln Gly Phe Gln Ser Pro Pro Ala Ser
                405                 410                 415

Ser Ser Ser Val Thr Ile Asn Thr Ala Pro Phe Gln Ala Met Gln Thr
            420                 425                 430

Val Phe Asn Val Asn Ala Pro Leu Pro Pro Arg Lys Glu Gln Glu Ile
        435                 440                 445

Lys Glu Ser Pro Tyr Ser Pro Gly Tyr Asn Gln Ser Leu Thr Thr Ala
450                 455                 460

Ser Thr Gln Thr Pro Pro Gln
465                 470

<210> SEQ ID NO 5
<211> LENGTH: 611
<212> TYPE: DNA
<213> ORGANISM: Homo sapiens
<220> FEATURE:
<221> NAME/KEY: CDS
<222> LOCATION: (1)...(606)

<400> SEQUENCE: 5 atg ggc tcc ggg cgc cgg gcg ctg tcc gcg gtg ccg gcc gtg ctg ctg      48
Met Gly Ser Gly Arg Arg Ala Leu Ser Ala Val Pro Ala Val Leu Leu
 1               5                  10                  15 gtc ctc acg ctg ccg ggg ctg ccc gtc tgg gca cag aac gac acg gag      96
Val Leu Thr Leu Pro Gly Leu Pro Val Trp Ala Gln Asn Asp Thr Glu
            20                  25                  30 ccc atc gtg ctg gag ggc aag tgt ctg gtg gtg tgc gac tca aac ccg     144
Pro Ile Val Leu Glu Gly Lys Cys Leu Val Val Cys Asp Ser Asn Pro
        35                  40                  45
```

```
gcc acg gac tcc aag ggc tcc tct tcc tcc ccg ctg ggg ata tcg gtc      192
Ala Thr Asp Ser Lys Gly Ser Ser Ser Ser Pro Leu Gly Ile Ser Val
 50                  55                  60 cgg gcg gcc aac tcc aag gtc gcc ttc tcg gcg gtg cgg agc acc aac      240
Arg Ala Ala Asn Ser Lys Val Ala Phe Ser Ala Val Arg Ser Thr Asn
 65                  70                  75                  80 cac gag cca tcc gag atg agc aac aag acg cgc atc att tac ttc gat      288
His Glu Pro Ser Glu Met Ser Asn Lys Thr Arg Ile Ile Tyr Phe Asp
                     85                  90                  95 cag atc ctg gtg aat gtg ggt aat ttt ttc aca ttg gag tct gtc ttt      336
Gln Ile Leu Val Asn Val Gly Asn Phe Phe Thr Leu Glu Ser Val Phe
                 100                 105                 110 gta gca cca aga aaa gga att tac agt ttc agt ttt cac gtg att aaa      384
Val Ala Pro Arg Lys Gly Ile Tyr Ser Phe Ser Phe His Val Ile Lys
             115                 120                 125 tac cag agc caa act atc cag gtt aac ttg atg tta aat gga aaa          432
Val Tyr Gln Ser Gln Thr Ile Gln Val Asn Leu Met Leu Asn Gly Lys
 130                 135                 140 cca gta ata tct gcc ttt gcg ggg gac aaa gat gtt act cgt gaa gct      480
Pro Val Ile Ser Ala Phe Ala Gly Asp Lys Asp Val Thr Arg Glu Ala
145                 150                 155                 160 gcc acg aat ggt gtc ctg ctc tac cta gat aaa gag gat aag gtt tac      528
Ala Thr Asn Gly Val Leu Leu Tyr Leu Asp Lys Glu Asp Lys Val Tyr
                 165                 170                 175 cta aaa ctg gag aaa ggt aat ttg gtt gga ggc tgg cag tat tcc acg      576
Leu Lys Leu Glu Lys Gly Asn Leu Val Gly Gly Trp Gln Tyr Ser Thr
             180                 185                 190 ttt tct ggc ttt ctg gtg ttc ccc cta tag gattc                        611
Phe Ser Gly Phe Leu Val Phe Pro Leu *
 195                 200
```

<210> SEQ ID NO 6
<211> LENGTH: 201
<212> TYPE: PRT
<213> ORGANISM: Homo sapiens

<400> SEQUENCE: 6

```
Met Gly Ser Gly Arg Arg Ala Leu Ser Ala Val Pro Ala Val Leu Leu
 1               5                  10                  15

Val Leu Thr Leu Pro Gly Leu Pro Val Trp Ala Gln Asn Asp Thr Glu
                 20                  25                  30

Pro Ile Val Leu Glu Gly Lys Cys Leu Val Val Cys Asp Ser Asn Pro
             35                  40                  45

Ala Thr Asp Ser Lys Gly Ser Ser Ser Ser Pro Leu Gly Ile Ser Val
 50                  55                  60

Arg Ala Ala Asn Ser Lys Val Ala Phe Ser Ala Val Arg Ser Thr Asn
 65                  70                  75                  80

His Glu Pro Ser Glu Met Ser Asn Lys Thr Arg Ile Ile Tyr Phe Asp
                     85                  90                  95

Gln Ile Leu Val Asn Val Gly Asn Phe Phe Thr Leu Glu Ser Val Phe
                 100                 105                 110

Val Ala Pro Arg Lys Gly Ile Tyr Ser Phe Ser Phe His Val Ile Lys
             115                 120                 125

Val Tyr Gln Ser Gln Thr Ile Gln Val Asn Leu Met Leu Asn Gly Lys
 130                 135                 140

Pro Val Ile Ser Ala Phe Ala Gly Asp Lys Asp Val Thr Arg Glu Ala
145                 150                 155                 160

Ala Thr Asn Gly Val Leu Leu Tyr Leu Asp Lys Glu Asp Lys Val Tyr
```

```
                    165                 170                 175
Leu Lys Leu Glu Lys Gly Asn Leu Val Gly Gly Trp Gln Tyr Ser Thr
            180                 185                 190

Phe Ser Gly Phe Leu Val Phe Pro Leu
        195                 200

<210> SEQ ID NO 7
<211> LENGTH: 1338
<212> TYPE: DNA
<213> ORGANISM: Homo sapiens
<220> FEATURE:
<221> NAME/KEY: CDS
<222> LOCATION: (1)...(1338)

<400> SEQUENCE: 7 atg tgc cca ctg agt tgt cag ctt ctc gtt ggt tgt ttc tca ttt ttt     48
Met Cys Pro Leu Ser Cys Gln Leu Leu Val Gly Cys Phe Ser Phe Phe
1               5                   10                  15 ctg gaa tgt cct ggt gcc cca ggt tta cca caa tat aca gga gaa ata     96
Leu Glu Cys Pro Gly Ala Pro Gly Leu Pro Gln Tyr Thr Gly Glu Ile
            20                  25                  30 agt gaa atg aca aaa tgc ccc tgt cct gat ata gaa agg tca gcc ttt    144
Ser Glu Met Thr Lys Cys Pro Cys Pro Asp Ile Glu Arg Ser Ala Phe
        35                  40                  45 act gtg aag ctc agt gga aaa ctt cct ctt cct ttc aag ccc atc atc    192
Thr Val Lys Leu Ser Gly Lys Leu Pro Leu Pro Phe Lys Pro Ile Ile
    50                  55                  60 ttc aca ggg gtc ctg tac aat gcc cag agg gat tta aag gag gcc atg    240
Phe Thr Gly Val Leu Tyr Asn Ala Gln Arg Asp Leu Lys Glu Ala Met
65                  70                  75                  80 gga gtc ttt gct tgc agg gtg cct ggg aat tac tac tcc agc ttt gat    288
Gly Val Phe Ala Cys Arg Val Pro Gly Asn Tyr Tyr Ser Ser Phe Asp
                85                  90                  95 gtt gag ctg cat cat tgc aag gtg aat att tgg cta atg agg aag caa    336
Val Glu Leu His His Cys Lys Val Asn Ile Trp Leu Met Arg Lys Gln
            100                 105                 110 att ttg gct aat aag gaa gaa att tct aag cag caa agc att caa gag    384
Ile Leu Ala Asn Lys Glu Glu Ile Ser Lys Gln Gln Ser Ile Gln Glu
        115                 120                 125 gtg act tgg gtg ctg tta aag gca ttc agt ttc ata agg gag gca gag    432
Val Thr Trp Val Leu Leu Lys Ala Phe Ser Phe Ile Arg Glu Ala Glu
    130                 135                 140 cat aag agt tca gaa aat ttg cac cct gac aat gtg ata aaa aag aaa    480
His Lys Ser Ser Glu Asn Leu His Pro Asp Asn Val Ile Lys Lys Lys
145                 150                 155                 160 aac cca ttt tct gag ggg aaa ttc aag ctg gct gca gaa att tgc ata    528
Asn Pro Phe Ser Glu Gly Lys Phe Lys Leu Ala Ala Glu Ile Cys Ile
                165                 170                 175 tgt aat gag gag ctg aat gtt aat cct caa gac aat ggg gaa aat atc    576
Cys Asn Glu Glu Leu Asn Val Asn Pro Gln Asp Asn Gly Glu Asn Ile
            180                 185                 190 tcc tgg aca tgt cag agg tct tca cag cag tcc atc aaa tca ctg gcc    624
Ser Trp Thr Cys Gln Arg Ser Ser Gln Gln Ser Ile Lys Ser Leu Ala
        195                 200                 205 tgg agg cct agg aga aaa tgg ttt tgt ggg aca ggc cca ggt ccc ctg    672
Trp Arg Pro Arg Arg Lys Trp Phe Cys Gly Thr Gly Pro Gly Ser Leu
    210                 215                 220 tgc tgt gtg cag cct aga gac ttg gtg ccc tgt gtc cca gtt aat tca    720
Cys Cys Val Gln Pro Arg Asp Leu Val Pro Cys Val Pro Val Asn Ser
225                 230                 235                 240
```

-continued

| | |
|---|---|
| gct gtg gct tca gag ggt gca agc ccc aag cct tgg cag ctt cca agt<br>Ala Val Ala Ser Glu Gly Ala Ser Pro Lys Pro Trp Gln Leu Pro Ser<br>245 250 255 | 768 |
| ggt gtt gag cct gtg ggt gca aag aag tca aga att gag gtt tgg gaa<br>Gly Val Glu Pro Val Gly Ala Lys Lys Ser Arg Ile Glu Val Trp Glu<br>260 265 270 | 816 |
| cct cca atc aga ttt cag aag ata tat gga aac ccc tgg atg ccc agg<br>Pro Pro Ile Arg Phe Gln Lys Ile Tyr Gly Asn Pro Trp Met Pro Arg<br>275 280 285 | 864 |
| cag aag ttt gct gta ggg gtg ggg tcc tca tgg aga acc tct gca agg<br>Gln Lys Phe Ala Val Gly Val Gly Ser Ser Trp Arg Thr Ser Ala Arg<br>290 295 300 | 912 |
| gta gta caa aag gga aat gtt ggg tgg gag ccc cca cac aga gtc ccc<br>Val Val Gln Lys Gly Asn Val Gly Trp Glu Pro Pro His Arg Val Pro<br>305 310 315 320 | 960 |
| agt ggg gct cca tct agt aga gct gtg aga aga agt cca cca tcc tcc<br>Ser Gly Ala Pro Ser Ser Arg Ala Val Arg Arg Ser Pro Pro Ser Ser<br>325 330 335 | 1008 |
| aga ctc cag aag ggt aga tcc act gac agc ttg cag cat gtg cct gaa<br>Arg Leu Gln Lys Gly Arg Ser Thr Asp Ser Leu Gln His Val Pro Glu<br>340 345 350 | 1056 |
| aaa tcc aca gac act cag tgc cag cct gtg aaa gca gca ggg atg gag<br>Lys Ser Thr Asp Thr Gln Cys Gln Pro Val Lys Ala Ala Gly Met Glu<br>355 360 365 | 1104 |
| tct gta ccc tac aaa acc gta gtg gca gag ctg acc aag acc gtg gga<br>Ser Val Pro Tyr Lys Thr Val Val Ala Glu Leu Thr Lys Thr Val Gly<br>370 375 380 | 1152 |
| atc tac ctc ttg cat tgt cat gac ctg gac gtg aga cat gga gtc aaa<br>Ile Tyr Leu Leu His Cys His Asp Leu Asp Val Arg His Gly Val Lys<br>385 390 395 400 | 1200 |
| aga gat cat ttt gga gct tta aga ttt gac tgc ccc act gga ttt cgg<br>Arg Asp His Phe Gly Ala Leu Arg Phe Asp Cys Pro Thr Gly Phe Arg<br>405 410 415 | 1248 |
| act tat atg ggg ccc gta ccc ctt tgt ttt ggc caa ttt ttt cca ttt<br>Thr Tyr Met Gly Pro Val Pro Leu Cys Phe Gly Gln Phe Phe Pro Phe<br>420 425 430 | 1296 |
| gga act gcc gta ttt acc caa tgc ctg tac ctc cat tgt atg<br>Gly Thr Ala Val Phe Thr Gln Cys Leu Tyr Leu His Cys Met<br>435 440 445 | 1338 |

<210> SEQ ID NO 8
<211> LENGTH: 446
<212> TYPE: PRT
<213> ORGANISM: Homo sapiens

<400> SEQUENCE: 8

Met Cys Pro Leu Ser Cys Gln Leu Leu Val Gly Cys Phe Ser Phe Phe
1               5                   10                  15

Leu Glu Cys Pro Gly Ala Pro Gly Leu Pro Gln Tyr Thr Gly Glu Ile
                20                  25                  30

Ser Glu Met Thr Lys Cys Pro Cys Pro Asp Ile Glu Arg Ser Ala Phe
            35                  40                  45

Thr Val Lys Leu Ser Gly Lys Leu Pro Leu Pro Phe Lys Pro Ile Ile
        50                  55                  60

Phe Thr Gly Val Leu Tyr Asn Ala Gln Arg Asp Leu Lys Glu Ala Met
65                  70                  75                  80

Gly Val Phe Ala Cys Arg Val Pro Gly Asn Tyr Tyr Ser Ser Phe Asp
                85                  90                  95

Val Glu Leu His His Cys Lys Val Asn Ile Trp Leu Met Arg Lys Gln

```
                100                 105                 110
Ile Leu Ala Asn Lys Glu Glu Ile Ser Lys Gln Gln Ser Ile Gln Glu
        115                 120                 125

Val Thr Trp Val Leu Leu Lys Ala Phe Ser Phe Ile Arg Glu Ala Glu
130                 135                 140

His Lys Ser Ser Glu Asn Leu His Pro Asp Asn Val Ile Lys Lys Lys
145                 150                 155                 160

Asn Pro Phe Ser Glu Gly Lys Phe Lys Leu Ala Ala Glu Ile Cys Ile
                165                 170                 175

Cys Asn Glu Glu Leu Asn Val Asn Pro Gln Asp Asn Gly Glu Asn Ile
            180                 185                 190

Ser Trp Thr Cys Gln Arg Ser Ser Gln Gln Ser Ile Lys Ser Leu Ala
        195                 200                 205

Trp Arg Pro Arg Arg Lys Trp Phe Cys Gly Thr Gly Pro Gly Ser Leu
210                 215                 220

Cys Cys Val Gln Pro Arg Asp Leu Val Pro Cys Val Pro Val Asn Ser
225                 230                 235                 240

Ala Val Ala Ser Glu Gly Ala Ser Pro Lys Pro Trp Gln Leu Pro Ser
                245                 250                 255

Gly Val Glu Pro Val Gly Ala Lys Lys Ser Arg Ile Glu Val Trp Glu
            260                 265                 270

Pro Pro Ile Arg Phe Gln Lys Ile Tyr Gly Asn Pro Trp Met Pro Arg
        275                 280                 285

Gln Lys Phe Ala Val Gly Val Gly Ser Ser Trp Arg Thr Ser Ala Arg
    290                 295                 300

Val Val Gln Lys Gly Asn Val Gly Trp Glu Pro Pro His Arg Val Pro
305                 310                 315                 320

Ser Gly Ala Pro Ser Ser Arg Ala Val Arg Arg Ser Pro Pro Ser Ser
                325                 330                 335

Arg Leu Gln Lys Gly Arg Ser Thr Asp Ser Leu Gln His Val Pro Glu
            340                 345                 350

Lys Ser Thr Asp Thr Gln Cys Gln Pro Val Lys Ala Ala Gly Met Glu
        355                 360                 365

Ser Val Pro Tyr Lys Thr Val Val Ala Glu Leu Thr Lys Thr Val Gly
    370                 375                 380

Ile Tyr Leu Leu His Cys His Asp Leu Asp Val Arg His Gly Val Lys
385                 390                 395                 400

Arg Asp His Phe Gly Ala Leu Arg Phe Asp Cys Pro Thr Gly Phe Arg
                405                 410                 415

Thr Tyr Met Gly Pro Val Pro Leu Cys Phe Gly Gln Phe Phe Pro Phe
            420                 425                 430

Gly Thr Ala Val Phe Thr Gln Cys Leu Tyr Leu His Cys Met
        435                 440                 445

<210> SEQ ID NO 9
<211> LENGTH: 1242
<212> TYPE: DNA
<213> ORGANISM: Homo sapiens
<220> FEATURE:
<221> NAME/KEY: CDS
<222> LOCATION: (251)...(1141)

<400> SEQUENCE: 9
ctcaggaggt tgtttaaact gagaaagaca gttgcaaaac ttcgtacaac agcatgagct     60
ccaagcttca aacgcattct catgctcaga cgagcacttt atttttcatc aagttatttt   120
```

```
ttgcattgtt ttggagtagc ttcgaataat aaacacatat ttctgcttta aatttttaat      180
agttaactac attcatggga caaccaaagc aagaaagcct catgttttgg gggaaagttt      240
gatatcagca atg tcc aga caa gag cca aag atg ttt gtc ttg ctc tat         289
          Met Ser Arg Gln Glu Pro Lys Met Phe Val Leu Leu Tyr
           1               5                   10 gtt aca agt ttt gcc att tgt gcc agt gga caa ccc cgg ggt aat cag        337
Val Thr Ser Phe Ala Ile Cys Ala Ser Gly Gln Pro Arg Gly Asn Gln
 15                  20                  25 ttg aaa gga gag aac tac tcc ccc agg tat atc tgc agc att cct ggc        385
Leu Lys Gly Glu Asn Tyr Ser Pro Arg Tyr Ile Cys Ser Ile Pro Gly
 30                  35                  40                  45 ttg cct gga cct cca ggg ccc cct gga gca aat ggt tcc cct ggg ccc        433
Leu Pro Gly Pro Pro Gly Pro Pro Gly Ala Asn Gly Ser Pro Gly Pro
                 50                  55                  60 cat ggt cgc atc ggc ctt cca gga aga gat ggt aga gac ggc agg aaa        481
His Gly Arg Ile Gly Leu Pro Gly Arg Asp Gly Arg Asp Gly Arg Lys
             65                  70                  75 gga gag aaa ggt gaa aag gga act gca ggt ttg aga ggt aag act gga        529
Gly Glu Lys Gly Glu Lys Gly Thr Ala Gly Leu Arg Gly Lys Thr Gly
         80                  85                  90 ccg cta ggt ctt gcc ggt gag aaa ggg gac caa gga gag act ggg aag        577
Pro Leu Gly Leu Ala Gly Glu Lys Gly Asp Gln Gly Glu Thr Gly Lys
     95                  100                 105 aaa gga ccc ata gga cca gag gga gag aaa gga gaa gta ggt cca att        625
Lys Gly Pro Ile Gly Pro Glu Gly Glu Lys Gly Glu Val Gly Pro Ile
110                 115                 120                 125 ggt cct cct gga cca aag gga gac aga gga gaa caa ggg gac ccg ggg        673
Gly Pro Pro Gly Pro Lys Gly Asp Arg Gly Glu Gln Gly Asp Pro Gly
                 130                 135                 140 ctg cct gga gtt tgc aga tgt gga agc atc gtg ctc aaa tcc gcc ttt        721
Leu Pro Gly Val Cys Arg Cys Gly Ser Ile Val Leu Lys Ser Ala Phe
             145                 150                 155 tct gtt ggc atc aca acc agc tac cca gaa gaa aga cta cct att ata        769
Ser Val Gly Ile Thr Thr Ser Tyr Pro Glu Glu Arg Leu Pro Ile Ile
         160                 165                 170 ttt aac aag gtc ctc ttc aac gag gga gag cac tac aac cct gcc aca        817
Phe Asn Lys Val Leu Phe Asn Glu Gly Glu His Tyr Asn Pro Ala Thr
     175                 180                 185 ggg aag ttc atc tgt gct ttc cca ggg atc tat tac ttt tct tat gat        865
Gly Lys Phe Ile Cys Ala Phe Pro Gly Ile Tyr Tyr Phe Ser Tyr Asp
190                 195                 200                 205 atc aca ttg gct aat aag cat ctg gca atc gga ctg gta cac aat ggg        913
Ile Thr Leu Ala Asn Lys His Leu Ala Ile Gly Leu Val His Asn Gly
                 210                 215                 220 caa tac cgg ata aag acc ttc gac gcc aac aca gga aac cat gat gtg        961
Gln Tyr Arg Ile Lys Thr Phe Asp Ala Asn Thr Gly Asn His Asp Val
             225                 230                 235 gct tcg ggg tcc aca gtc atc tat ctg cag cca gaa gat gaa gtc tgg        1009
Ala Ser Gly Ser Thr Val Ile Tyr Leu Gln Pro Glu Asp Glu Val Trp
         240                 245                 250 ctg gag att ttc ttc aca gac cag aat ggc ctc ttc tca gac cca ggt        1057
Leu Glu Ile Phe Phe Thr Asp Gln Asn Gly Leu Phe Ser Asp Pro Gly
     255                 260                 265 tgg gca gac agc tta ttc tcc ggg ttt ctc tta tac gtt gac aca gat        1105
Trp Ala Asp Ser Leu Phe Ser Gly Phe Leu Leu Tyr Val Asp Thr Asp
270                 275                 280                 285 tac cta gat tcc ata tca gaa gat gat gaa ttg tga tcaggccaag             1151
Tyr Leu Asp Ser Ile Ser Glu Asp Asp Glu Leu *
```

```
                290             295
atcctgtggt aacacttgtt gatctggggt tcagaagtgg acaagcagga atgggatcca        1211
agagactccc tcagatctaa gcattaagca t                                       1242
```

<210> SEQ ID NO 10
<211> LENGTH: 296
<212> TYPE: PRT
<213> ORGANISM: Homo sapiens

<400> SEQUENCE: 10

```
Met Ser Arg Gln Glu Pro Lys Met Phe Val Leu Leu Tyr Val Thr Ser
 1               5                  10                  15
Phe Ala Ile Cys Ala Ser Gly Gln Pro Arg Gly Asn Gln Leu Lys Gly
            20                  25                  30
Glu Asn Tyr Ser Pro Arg Tyr Ile Cys Ser Ile Pro Gly Leu Pro Gly
        35                  40                  45
Pro Pro Gly Pro Pro Gly Ala Asn Gly Ser Pro Gly Pro His Gly Arg
    50                  55                  60
Ile Gly Leu Pro Gly Arg Asp Gly Arg Asp Gly Arg Lys Gly Glu Lys
65                  70                  75                  80
Gly Glu Lys Gly Thr Ala Gly Leu Arg Gly Lys Thr Gly Pro Leu Gly
                85                  90                  95
Leu Ala Gly Glu Lys Gly Asp Gln Gly Glu Thr Gly Lys Lys Gly Pro
            100                 105                 110
Ile Gly Pro Glu Gly Glu Lys Gly Glu Val Gly Pro Ile Gly Pro Pro
        115                 120                 125
Gly Pro Lys Gly Asp Arg Gly Glu Gln Gly Asp Pro Gly Leu Pro Gly
    130                 135                 140
Val Cys Arg Cys Gly Ser Ile Val Leu Lys Ser Ala Phe Ser Val Gly
145                 150                 155                 160
Ile Thr Thr Ser Tyr Pro Glu Glu Arg Leu Pro Ile Ile Phe Asn Lys
                165                 170                 175
Val Leu Phe Asn Glu Gly Glu His Tyr Asn Pro Ala Thr Gly Lys Phe
            180                 185                 190
Ile Cys Ala Phe Pro Gly Ile Tyr Tyr Phe Ser Tyr Asp Ile Thr Leu
        195                 200                 205
Ala Asn Lys His Leu Ala Ile Gly Leu Val His Asn Gly Gln Tyr Arg
    210                 215                 220
Ile Lys Thr Phe Asp Ala Asn Thr Gly Asn His Asp Val Ala Ser Gly
225                 230                 235                 240
Ser Thr Val Ile Tyr Leu Gln Pro Glu Asp Glu Val Trp Leu Glu Ile
                245                 250                 255
Phe Phe Thr Asp Gln Asn Gly Leu Phe Ser Asp Pro Gly Trp Ala Asp
            260                 265                 270
Ser Leu Phe Ser Gly Phe Leu Leu Tyr Val Asp Thr Asp Tyr Leu Asp
        275                 280                 285
Ser Ile Ser Glu Asp Asp Glu Leu
    290                 295
```

<210> SEQ ID NO 11
<211> LENGTH: 770
<212> TYPE: DNA
<213> ORGANISM: Homo sapiens
<220> FEATURE:
<221> NAME/KEY: CDS
<222> LOCATION: (1)...(618)

```
<400> SEQUENCE: 11 atg ttg gga gcc aag cca cac tgg cta cca ggt ccc cta cgc agt ccc      48
Met Leu Gly Ala Lys Pro His Trp Leu Pro Gly Pro Leu Arg Ser Pro
 1               5                  10                  15 ggg ctg ccc ttg gtt ctg gtg ctt ctg gcc ctg ggg gcc ggg tgg gcc      96
Gly Leu Pro Leu Val Leu Val Leu Leu Ala Leu Gly Ala Gly Trp Ala
             20                  25                  30 cag gag ggg tca gag ccc gtc ctg ctg gag ggg gag tgc ctg gtg gtc     144
Gln Glu Gly Ser Glu Pro Val Leu Leu Glu Gly Glu Cys Leu Val Val
         35                  40                  45 tgt gag cct ggc cga gct gct gca ggg ggg ccc ggg gga gca gcc ctg     192
Cys Glu Pro Gly Arg Ala Ala Ala Gly Gly Pro Gly Gly Ala Ala Leu
 50                  55                  60 gga gag gca ccc cct ggg cga gtg gca ttt gct gcg gtc cga agc cac     240
Gly Glu Ala Pro Pro Gly Arg Val Ala Phe Ala Ala Val Arg Ser His
 65                  70                  75                  80 cac cat gag cca gca ggg gaa acc ggc aat ggc acc agt ggg gcc atc     288
His His Glu Pro Ala Gly Glu Thr Gly Asn Gly Thr Ser Gly Ala Ile
                 85                  90                  95 tac ttc gac cag gtc ctg gtg aac gag ggc ggt ggc ttt gac cgg gcc     336
Tyr Phe Asp Gln Val Leu Val Asn Glu Gly Gly Gly Phe Asp Arg Ala
            100                 105                 110 tct ggc tcc ttc gta gcc cct gtc cgg ggt gtc tac agc ttc cgg ttc     384
Ser Gly Ser Phe Val Ala Pro Val Arg Gly Val Tyr Ser Phe Arg Phe
        115                 120                 125 cat gtg gtg aag gtg tac aac cgc caa act gtc cag gtg agc ctg atg     432
His Val Val Lys Val Tyr Asn Arg Gln Thr Val Gln Val Ser Leu Met
130                 135                 140 ctg aac acg tgg cct gtc atc tca gcc ttt gcc aat gat cct gac gtg     480
Leu Asn Thr Trp Pro Val Ile Ser Ala Phe Ala Asn Asp Pro Asp Val
145                 150                 155                 160 acc cgg ggg gca gcc acc agc tct gtg cta ctg ccc ttg gac cct ggg     528
Thr Arg Gly Ala Ala Thr Ser Ser Val Leu Leu Pro Leu Asp Pro Gly
                165                 170                 175 gac cga gtg tct ctg cgc ctg cgt cgg ggg aat cta ctg ggt ggt tgg     576
Asp Arg Val Ser Leu Arg Leu Arg Arg Gly Asn Leu Leu Gly Gly Trp
            180                 185                 190 aaa tac tca agt ttc tct ggc ttc ctc atc ttc cct ctc tga             618
Lys Tyr Ser Ser Phe Ser Gly Phe Leu Ile Phe Pro Leu *
        195                 200                 205 aggacccaag tctttcaagc acaagaatcc agccctgac aactttcttc tgccctctct     678
tgccccaaaa acagcagagg caggagagag actccctctg gctcctatcc cacctctttg     738
catgggaccc tgtgccaaac acccaagttt aa                                   770

<210> SEQ ID NO 12
<211> LENGTH: 205
<212> TYPE: PRT
<213> ORGANISM: Homo sapiens

<400> SEQUENCE: 12

Met Leu Gly Ala Lys Pro His Trp Leu Pro Gly Pro Leu Arg Ser Pro
 1               5                  10                  15

Gly Leu Pro Leu Val Leu Val Leu Leu Ala Leu Gly Ala Gly Trp Ala
             20                  25                  30

Gln Glu Gly Ser Glu Pro Val Leu Leu Glu Gly Glu Cys Leu Val Val
         35                  40                  45

Cys Glu Pro Gly Arg Ala Ala Ala Gly Gly Pro Gly Gly Ala Ala Leu
```

```
                          -continued
        50                   55                   60
Gly Glu Ala Pro Pro Gly Arg Val Ala Phe Ala Ala Val Arg Ser His
65                       70                  75                  80

His His Glu Pro Ala Gly Glu Thr Gly Asn Gly Thr Ser Gly Ala Ile
                85                  90                  95

Tyr Phe Asp Gln Val Leu Val Asn Glu Gly Gly Gly Phe Asp Arg Ala
                100                 105                 110

Ser Gly Ser Phe Val Ala Pro Val Arg Gly Val Tyr Ser Phe Arg Phe
            115                 120                 125

His Val Val Lys Val Tyr Asn Arg Gln Thr Val Gln Val Ser Leu Met
        130                 135                 140

Leu Asn Thr Trp Pro Val Ile Ser Ala Phe Ala Asn Asp Pro Asp Val
145                 150                 155                 160

Thr Arg Gly Ala Ala Thr Ser Ser Val Leu Leu Pro Leu Asp Pro Gly
                165                 170                 175

Asp Arg Val Ser Leu Arg Leu Arg Arg Gly Asn Leu Leu Gly Gly Trp
            180                 185                 190

Lys Tyr Ser Ser Phe Ser Gly Phe Leu Ile Phe Pro Leu
            195                 200                 205
```

METABOLIC GENE POLYNUCLEOTIDES AND POLYPEPTIDES AND USES THEREOF

FIELD OF THE INVENTION

The present invention relates to the field of metabolic research, in particular the discovery of compounds effective for reducing body mass and useful for treating metabolic-related diseases and disorders. The metabolic-related diseases or disorders envisioned to be treated by the methods of the invention include, but are not limited to, hyperlipidemia, atherosclerosis, diabetes, and hypertension.

BACKGROUND OF THE INVENTION

The following discussion is intended to facilitate the understanding of the invention, but is not intended nor admitted to be prior art to the invention.

Obesity is a public health problem that is serious, widespread, and increasing. In the United States, 20 percent of the population is obese; in Europe, a slightly lower percentage is obese (Friedman (2000) Nature 404:632-634). Obesity is associated with increased risk of hypertension, cardiovascular disease, diabetes, and cancer as well as respiratory complications and osteoarthritis (Kopelman (2000) Nature 404:635-643). Even modest weight loss ameliorates these associated conditions.

While still acknowledging that lifestyle factors including environment, diet, age and exercise play a role in obesity, twin studies, analyses of familial aggregation, and adoption studies all indicate that obesity is largely the result of genetic factors (Harsh et al (2000) Nature 404:644-651). In agreement with these studies, is the fact that an increasing number of metabolic-related genes are being identified. Some of the more extensively studied genes include those encoding leptin (ob) and its receptor (db), pro-opiomelanocortin (Poinc), melanocortin-4-receptor (Mc4r), agouti protein ($A^y$), carboxypeptidase E (fat), 5-hydroxytryptamine receptor 2C (Htr2c), nescient basic helix-loop-helix 2 (Nhlh2), prohormone convertase 1 (PCSK1), and tubby protein (tubby) (rev'd in Barsh et al (2000) Nature 404:644-651).

SUMMARY OF THE INVENTION

The instant invention is based on Genset Metabolic Genes-7, 8, 9, 10, and 11 (GMG-7), (GMG-8; previously referred to as Cluster 9), (GMG-9; previously referred to as Cluster 10), (GMG-10; previously referred to as Cluster 17(a)) and (GMG-11; previously referred to as Cluster 19) of human origin. GMG-7A (previously referred to as Cluster 6 (1900)) and GMG-7B (previously referred to as Cluster 6 (d)) correspond to splice variants of GMG-7. GMG-7A, GMG-8, GMG-10, and GMG-11 are comprised of a C-terminal globular C1q homology domain. GMG-7B lacks the C-terminal globular C1q homology domain present in GMG-7A. GMG-9 is comprised near its N-terminus of a truncated globular C1q homology domain. Analysis of the C-terminal globular C1q homology domain of APM1 has shown it to structurally resemble TNFα. By analogy to APM1, biological activity can also reside in polypeptide fragments exclusive of all or part of the globular C1q homology domain. Results from Northern blot analysis indicate expression of GMG-7 in heart and brain, expression of GMG-8 in brain, and expression of GMG-11 in brain and pancreas.

The invention includes polypeptides encoded by GMG-7A, GMG-7B, GMG-8, GMG-9, GMG-10, and GMG-11, which include both the full-length polypeptide and fragments thereof, preferably but not intended to be limited to said polypeptide fragments comprising all or part of the C-terminal globular C1q homology domain. The GMG-7A, GMG-7B, GMG-8, GMG-9, GMG-10, and GMG-11 polypeptide fragments of the invention have in vitro and in vivo biological activity as described herein, including utility for weight reduction, prevention of weight gain and control of blood glucose levels in humans and other mammals. More specifically, the biological activities of the GMG-7A, GMG-7B, GMG-8, GMG-9, GMG-10, and GMG-11 polypeptides, including fragments, include reduction of elevated free fatty acid levels caused by administration of epinephrine, i.v. injection of "intralipid", or administration of a high fat test meal, as well as increased fatty acid oxidation in muscle cells, reduction in glucose levels, modulation of energy expenditure, resistance to insulin and weight reduction in mammals consuming a high fat/high sucrose diet. Polypeptide fragments of the invention have activities overlapping but distinct from that of the full-length polypeptide.

Thus, the invention is drawn to GMG-7A, GMG-7B, GMG-8, GMG-9, GMG-10, and GMG-11 polypeptides, polynucleotides encoding said GMG-7A, GMG-7B, GMG-8, GMG-9, GMG-10, and GMG-11 polypeptides, vectors comprising said GMG-7A, GMG-7B, GMG-8, GMG-9, GMG-10, and GMG-11 polynucleotides, and cells recombinant for said GMG-7A, GMG-7B, GMG-8, GMG-9, GMG-10, and GMG-11 polynucleotides, as well as to pharmaceutical and physiologically acceptable compositions comprising said GMG-7A, GMG-7B, GMG-8, GMG-9, GMG-10, and GMG-11 polypeptides and methods of administering said GMG-7A, GMG-7B, GMG-8, GMG-9, GMG-10, and GMG-11 pharmaceutical and physiologically acceptable compositions in order to reduce body weight or to treat metabolic-related diseases and disorders. Assays for identifying agonists and antagonists of metabolic-related activity are also part of the invention.

In a first aspect, the invention features purified, isolated, or recombinant GMG-7A, GMG-7B, GMG-8, GMG-9, GMG-10, and GMG-11 polypeptides or GMG-7A, GMG-7B, GMG-8, GMG-9, GMG-10, and GMG-11 polypeptide fragments that have lipid partitioning, lipid metabolism, and insulin-like activities. Preferred GMG-7A, GMG-7B, GMG-8, GMG-9, GMG-10, and GMG-11 polypeptide fragments have activity, wherein said activity is also selected from the group consisting of lipid partitioning, lipid metabolism, and insulin-like activity. In preferred embodiments, said polypeptide fragment comprises, consists essentially of, or consists of, at least 6 consecutive amino acids and not more than 710 consecutive amino acids of SEQ ID NO: 2; at least 6 and not more than 471 consecutive amino acids of SEQ ID NO: 4; at least 6 consecutive amino acids and not more than 201 consecutive amino acids of SEQ ID NO: 6; at least 6 and not more than 446 consecutive amino acids of SEQ ID NO: 8; at least 6 consecutive amino acids and not more than 296 consecutive amino acids of SEQ ID NO: 10; or at least 6 and not more than 205 consecutive amino acids of SEQ ID NO: 12.

In preferred embodiments, GMG-7A polypeptide fragments having activity are selected from amino acids 2-710, 1-262, 263-710, 1-263, 264-710 1-552, 553-710, 554-710, 561-710, 568-710, 575-710, 580-710, 581-710, 1-275 or 276-710 of SEQ ID NO: 2. In other preferred embodiments, GMG-7B polypeptide fragments having activity are selected from amino acids 2-471, 1-442, 443-471, 1-443, 444-471, 1-262, 263-471, 1-263, 264-471, 1-275 or 276-471 of SEQ ID NO: 4. In other preferred embodiments, GMG-8 polypeptide fragments having activity are selected from amino acids 28-201, 40-201, 54-201, 66-201, 70-201, or 71-201 of SEQ ID NO: 6. In other preferred embodiments, GMG-9 polypeptide fragments having activity are selected from amino acids 25-446, 228-356, 228-360, 228-431, 228-446, 231-356, 231-360, 231-431, 231-446, 233-356, 233-360, 233-431, 233-446, 236-356, 236-360, 236-431, 236-446, 240-356, 240-360, 240-431, 240-446, 241-356, 241-360, 241-431, 241-446, 242-356, 242-360, 242-431, or 242-446 of SEQ ID NO: 8. In other preferred embodiments, GMG-10 polypeptide fragments having activity are selected from amino acids 8-296, 9-296, 24-296, 32-296, 39-296, 52-296, 65-296, 71-296, 74-296, 77-296, 78-296, 81-296, 84-296, 90-296, 92-296, 102-296, 110-296, 111-296, 120-296, 132-296, 135-296, 148-296, 154-296 or 155-296 of SEQ ID NO: 10. In other preferred embodiments, GMG-11 polypeptide fragments having activity are selected from amino acids 33-205, 53-205, 54-205, 59-205, 71-205 or 72-205 of SEQ ID NO: 12.

In more preferred embodiments, GMG-7A polypeptide fragments having activity are selected from amino acids 2-710, 1-262, 1-263, 553-710, 554-710, 568-710, 575-710 or 1-275 of SEQ ID NO: 2. In other more preferred embodiments, GMG-7B polypeptide fragments having activity are selected from amino acids 2-471, 14-42, 1-443, 1-262, 1-263, or 1-275 of SEQ ID NO: 4. In other more preferred embodiments, GMG-8 polypeptide fragments having activity are selected from amino acids 28-201, 54-201 or 66-201 of SEQ ID NO: 6. In other more preferred embodiments, GMG-9 polypeptide fragments having activity are selected from amino acids 254-46, 228-356, 228-360, 228-431, 228-446, 231-356, 231-360, 231-431, 231-446, 241-356, 241-360, 241-431 or 241-446 of SEQ ID NO: 8. In other more preferred embodiments, GMG-10 polypeptide fragments having activity are selected from amino acids 8-296, 9-296, 24-296, 52-296, 71-296, 74-296, 81-296, 84-296, 110-296, 111-296, 120-296, 132-296, 135-296, 148-296, 154-296 or 155-296 of SEQ ID NO: 10. In other more preferred embodiments, GMG-11 polypeptide fragments having activity are selected from amino acids 33-205, 53-205, 54-205 or 59-205 of SEQ ID NO: 12.

In further preferred embodiments, said polypeptide fragment comprises an amino acid sequence at least 70%, 75%, 80%, 85%, 90%, 91%, 92%, 93%, 94%, 95%, 96%, 97%, 98%, or 99% identical to the corresponding consecutive amino acids of the polypeptide sequences identified in SEQ ED NO: 2, 4, 6, 8, 10, or 12.

The invention further provides a purified or isolated polypeptide comprising, consisting of, or consisting essentially of an amino acid sequence selected from the group consisting of: (a) a full-length at least 90%, 91%, 92%, 93%, 94%, 95%, 96%, 97%, 98%, or 99% identical to the corresponding amino acids polypeptide of SEQ ID NOs: 2, 4, 6, 8, 10, or 12; (b) a full-length GMG-7A, GMG-7B, GMG-8, GMG-9, GMG-10, or GMG-11 polypeptide of SEQ ID NOs: 2, 4, 6, 8, 10, or 12 absent the N-terminal Met; (c) a mature GMG-8, GMG-9, GMG-10 or GMG-11 polypeptide of SEQ ID NOs: 6, 8, 10, or 12 lacking signal peptide; (d) a GMG-7A polypeptide of SEQ ID NO: 2 wherein said GMG-7A polypeptide is of any one integer in length between 6 amino acids and 710 amino acids (full-length) inclusive of SEQ ED NO: 2, a GMG-7B polypeptide of SEQ ID NO: 4 wherein said GMG-7B polypeptide is of any one integer in length between 6 amino acids and 471 amino acids (full-length) inclusive of SEQ ID NO: 4, a GMG-8 polypeptide of SEQ ID NO: 6 wherein said GMG-8 polypeptide is of any one integer in length between 6 amino acids and 201 amino acids (full-length) inclusive of SEQ ID NO: 6, a GMG-9 polypeptide of SEQ ID NO: 8 wherein said GMG-8 polypeptide is of any one integer in length between 6 amino acids and 446 amino acids (full-length) inclusive of SEQ ID NO: 8; or a GMG-10 polypeptide of SEQ ID NO: 10 wherein said GMG-10 polypeptide is of any one integer in length between 6 amino acids and 296 amino acids (full-length) inclusive of SEQ ID NO: 10; or a GMG-11 polypeptide of SEQ ID NO: 12 wherein said GMG-11 polypeptide is of any one integer in length between 6 amino acids and 205 amino acids (full-length) inclusive of SEQ ID NO: 12; (e) the epitope-bearing fragments of a GMG-7A, GMG-7B, GMG-8, GMG-9, GMG-10, or GMG-11 polypeptide of SEQ ED NO: 2, 4, 6, 8, 10, or 12; (f) the allelic variant polypeptides of any of the polypeptides of (a)-(e). The invention further provides for fragments of the polypeptides of (a)-(f) above, such as those having biological activity or comprising biologically functional domain(s).

In other highly preferred embodiments, GMG-7A, GMG-7B, GMG-8, GMG-9, GMG-10, or GMG-11 polypeptides comprise, consist essentially of, or consist of, a purified, isolated, or a recombinant GMG-7A, GMG-7B, GMG-8, GMG-9, GMG-10, or GMG-11 polypeptide fragment comprised of all or part of the C-terminal globular C1q homology domain. Preferably, said GMG-7A polypeptide fragment comprises, consists essentially of, or consists of, at least 6 consecutive amino acids of amino acids 2-710 of SEQ ID NO: 2. Preferably, said GMG-8 polypeptide fragment comprises, consists essentially of, or consists of, at least 6 consecutive amino acids of amino acids 28-201 of SEQ ID NO: 6. Preferably, said GMG-10 polypeptide fragment comprises, consists essentially of, or consists of, at least 6 consecutive amino acids of amino acids 24296 of SEQ ID NO: 10. Preferably, said GMG-11 polypeptide fragment comprises, consists essentially of, or consists of, at least 6 consecutive amino acids of amino acids 33-205 of SEQ ID NO: 12. In preferred embodiments, said GMG-7A polypeptide fragments comprised of all or part of the C-terminal globular C1q homology domain and having activity are selected from amino acids 2-710, 263-710, 264-710, 553-710, 554-710, 561-710, 568-710, 575-710, 580-710, 581-710, or 276-710 of SEQ ID NO: 2. In other preferred embodiments, said GMG-8 polypeptide fragments having activity are selected from amino acids 28-201, 40-201, 54-201, 66-201, 70-210 or 71-201 of SEQ ID NO: 6. In other preferred embodiments, said GMG-10 polypeptide fragments having activity are selected from amino acids 8-296, 9-296, 24-296, 32-296, 39-296, 52-296, 65-296, 71-296, 74-296, 77-296, 78-296, 81-296, 84-296, 90-296, 92-296, 102-296, 110-296, 111-296, 120-296, 132-296, 135-296, 148-296, 154-296 or 155-296 of SEQ ID NO: 10. In other preferred embodiments, said GMG-11 polypeptide fragments having activity are selected from amino acids 33-205, 53-205, 54-205, 59-205, 71-205 or 72-205 of SEQ ID NO: 12.

In more preferred embodiments, said GMG-7A polypeptide fragments comprised of all or part of the C-terminal globular C1q homology domain and having activity are selected from amino acids 2-710, 553-710, 554-710, 568-710, or 575-710 of SEQ ID NO: 2. In other more preferred embodiments, said GMG-8 polypeptide fragments having activity are selected from amino acids 28-201, 54-201 or 66-201 of SEQ ID NO: 6. In other more preferred embodiments, said GMG-10 polypeptide fragments having activity are selected from amino acids 8-296, 9-296, 24-296, 52-296, 71-296, 74-296, 81-296, 84-296, 110-296, 111-296, 120-296, 132-296, 135-296, 148-296, 154-296 or 155-296 of SEQ ID NO: 10. In other more preferred embodiments, said GMG-11 polypeptide fragments having activity are selected from amino acids 33-205, 53-205, 54-205 or 59-205 of SEQ ID NO: 12.

Alternatively, said GMG-7A, GMG-8, GMG-10, or GMG-11 polypeptide fragment comprises, consists essentially of, or consists of, an amino acid sequence at least 90%, 91%, 92%, 93%, 94%, 95%, 96%, 97%, 98%, or 99% identical to the corresponding amino acids 568-710 of SEQ ID NO: 2, at least 90%, 91%, 92%, 93%, 94%, 95%, 96%, 97%, 98%, or 99% identical to the corresponding amino acids 54-201 of SEQ ID NO: 6, at least 90%, 91%, 92%, 93%, 94%, 95%, 96%, 97%, 98%, or 99% identical to the corresponding amino acids 135-296 of SEQ ED NO: 10, or at least 90%, 91%, 92%, 93%, 94%, 95%, 96%, 97%, 98%, or 99% identical to the corresponding amino acids 53-205 of SEQ ID NO: 12.

In a further preferred embodiment, GMG-7A, GMG-7B, GMG-8, GMG-9, GMG-10, and GMG-11 polypeptides are able to lower circulating (either in blood, serum or plasma) levels (concentration) of: (i) free fatty acids, (ii) glucose, and/or (iii) triglycerides. Further preferred polypeptides of the invention demonstrating free fatty acid level lowering activity, glucose level lowering activity, and/or triglyceride level lowering activity, have an activity that is the same or greater than full-length GMG-7A, GMG-7B, GMG-8, GMG-9, GMG-10, or GMG-11 polypeptides at the same molar concentration, have the same or greater than transient activity and/or have a sustained activity.

Further preferred GMG-7A, GMG-7B, GMG-8, GMG-9, GMG-10, and GMG-11 polypeptides are those that significantly stimulate muscle lipid or free fatty acid oxidation. Further preferred GMG-7A, GMG-7B, GMG-8, GMG-9, GMG-10, and GMG-11 polypeptides are those that significantly stimulate muscle lipid or free fatty acid oxidation.

Further preferred GMG-7A, GMG-7B, GMG-8, GMG-9, GMG-10, and GMG-11 polypeptides are those that cause C2C12 cells differentiated in the presence of said polypeptides to undergo at least 10%, 20%, 30%, 35%, or 40% more oleate oxidation as compared to untreated cells.

Further preferred GMG-7A, GMG-7B, GMG-8, GMG-9, GMG-10, and GMG-11 polypeptides are those that increase leptin uptake in a liver cell line (preferably BPRCL mouse liver cells (ATCC CRL-2217)).

Further preferred GMG-7A, GMG-7B, GMG-8, GMG-9, GMG-10, and GMG-11 polypeptides are those that significantly reduce the postprandial increase in plasma free fatty acids due to a high fat meal.

Further preferred GMG-7A, GMG-7B, GMG-8, GMG-9, GMG-10, and GMG-11 polypeptides are those that significantly reduce or eliminate ketone body production as the result of a high fat meal.

Further preferred GMG-7A, GMG-7B, GMG-8, GMG-9, GMG-10, and GMG-11 polypeptides are those that increase glucose uptake in skeletal muscle cells.

Further preferred GMG-7A, GMG-7B, GMG-8, GMG-9, GMG-10, and GMG-11 polypeptides are those that increase glucose uptake in adipose cells.

Further preferred GMG-7A, GMG-7B, GMG-8, GMG-9, GMG-10, and GMG-11 polypeptides are those that increase glucose uptake in neuronal cells.

Further preferred GMG-7A, GMG-7B, GMG-8, GMG-9, GMG-10, and GMG-11 polypeptides are those that increase glucose uptake in red blood cells.

Further preferred GMG-7A, GMG-7B, GMG-8, GMG-9, GMG-10, and GMG-11 polypeptides are those that increase glucose uptake in the brain.

Further preferred GMG-7A, GMG-7B, GMG-8, GMG-9, GMG-10, and GMG-11 polypeptides are those that significantly reduce the postprandial increase in plasma glucose following a meal, particularly a high carbohydrate meal.

Further preferred GMG-7A, GMG-7B, GMG-8, GMG-9, GMG-10, and GMG-11 polypeptides are those that significantly prevent the postprandial increase in plasma glucose following a meal, particularly a high fat or a high carbohydrate meal.

Further preferred GMG-7A, GMG-7B, GMG-8, GMG-9, GMG-10, and GMG-11 polypeptides are those that increase insulin sensitivity.

Further preferred GMG-7A, GMG-7B, GMG-8, GMG-9, GMG-10, and GMG-11 polypeptides are those that inhibit the progression from impaired glucose tolerance to insulin resistance.

Further preferred GMG-7A, GMG-7B, GMG-8, GMG-9, GMG-10, and GMG-11 polypeptides are those that form multimers (e.g., heteromultimers or homomultimers) in vitro and/or in vivo. Preferred multimers are homodimers or homotrimers. Other preferred multimers are homomultimers comprising at least 4, 6, 8, 9, 10 or 12 GMG-7A, GMG-7B, GMG-8, GMG-9, GMG-10, or GMG-11 polypeptide subunits. Other preferred mulimers are hetero multimers comprising a GMG-7A, GMG-7B, GMG-8, GMG-9, GMG-10, or GMG-11 polypeptide of the invention.

Further preferred embodiments include heterologous polypeptides comprising one of the GMG-7A, GMG-7B, GMG-8, GMG-9, GMG-10, or GMG-11 polypeptides of the invention.

In a second aspect, the invention features purified, isolated, or recombinant polynucleotides encoding said GMG-7A, GMG-7B, GMG-8, GMG-9, GMG-10, or GMG-11 polypeptides described in the first aspect, or the complement thereof. A further preferred embodiment of the invention is a recombinant, purified or isolated polynucleotide comprising, or consisting of a mammalian genomic sequence, gene, or fragments thereof. In one aspect the sequence is derived from a human, mouse or other mammal. In a preferred aspect, the genomic sequence includes isolated, purified, or recombinant polynucleotides comprising a contiguous span of at least 12, 15, 18, 20, 22, 25, 30, 35, 40, 50, 60, 70, 80, 90, 100, 150, 200, 500, 1000, 2000, 5000, 10000 or 50000 nucleotides of any one of the polynucleotide sequences described in SEQ ID NOs: 1, 3, 5, 7, 9, or 11 or the complements thereof, wherein said contiguous span comprises a nucleotide sequence at least 90%, 91%, 92%, 93%, 94%, 95%, 96%, 97%, 98%, or 99% identical to the corresponding nucleotide sequence of the C-terminal globular C1q homology domains of SEQ ID NOs: 1, 3, 5, 7, 9, or 11. In further embodiments the polynucleotides are DNA, RNA, DNA/RNA hybrids, single-stranded, and double-stranded.

In a third aspect, the invention features a recombinant vector comprising, consisting essentially of, or consisting of, said polynucleotide described in the second aspect.

In a fourth aspect, the invention features a recombinant cell comprising, consisting essentially of, or consisting of, said recombinant vector described in the third aspect. A further embodiment includes a host cell recombinant for a polynucleotide of the invention.

In a fifth aspect, the invention features a pharmaceutical or physiologically acceptable composition comprising, consisting essentially of, or consisting of, said GMG-7A, GMG-7B, GMG-8, GMG-9, GMG-10, or GMG-11 polypeptides described in the first aspect and, alternatively, a pharmaceutical or physiologically acceptable diluent.

In a sixth aspect, the invention features a method of reducing body mass comprising providing or administering to individuals in need of reducing body mass said pharmaceutical or physiologically acceptable composition described in the fifth aspect.

In preferred embodiments, the identification of said individuals in need of reducing body mass to be treated with said pharmaceutical or physiologically acceptable composition comprises genotyping GMG-7A, GMG-7B, GMG-8, GMG-9, GMG-10, or GMG-11 single nucleotide polymorphisms (SNPs) or measuring metabolic polypeptide or mRNA levels in clinical samples from said individuals. Preferably, said clinical samples are selected from the group consisting of plasma, urine, and saliva. Preferably, a GMG-7A, GMG-7B, GMG-8, GMG-9, GMG-10, or GMG-11 polypeptide fragment of the present invention is administered to an individual with at least a 10%, 20%, 30%, 40%, 50%, 60%, 70%, 80%, 90%, or 100% reduction in blood, serum or plasma levels of full-length any one or all of the GMG-7A, GMG-7B, GMG-8, GMG-9, GMG-11, or GMG-11 polypeptides or the naturally proteolytically cleaved GMG-7A, GMG-7B, GMG-8, GMG-9, GMG-10, or GMG-11 fragments as compared to healthy, non-obese patients.

In a seventh aspect, the invention features a method of preventing or treating an metabolic-related disease or disorder comprising providing or administering to an individual in need of such treatment said pharmaceutical or physiologically acceptable composition described in the fifth aspect. In preferred embodiments, the identification of said individuals in need of such treatment to be treated with said pharmaceutical or physiologically acceptable composition comprises genotyping GMG-7A, GMG-7B, GMG-8, GMG-9, GMG-10, or GMG-11 single nucleotide polymorphisms (SNPs) or measuring GMG-7A, GMG-7B, GMG-8, GMG-9, GMG-10, or GMG-11 polypeptide or mRNA levels in clinical samples from said individuals. Preferably, said clinical samples are selected from the group consisting of blood, serum, plasma, urine, and saliva. Preferably, said metabolic-related disease or disorder is selected from the group consisting of obesity, impaired glucose tolerance, insulin resistance, atherosclerosis, atheromatous disease, heart disease, hypertension, stroke, Syndrome X, non-insulin-dependent diabetes and Type II diabetes. Type II diabetes-related complications to be treated by the methods of the invention include microangiopathic lesions, ocular lesions, and renal lesions. Heart disease includes, but is not limited to, cardiac insufficiency, coronary insufficiency, and high blood pressure. Other metabolic-related disorders to be treated by compounds of the invention include hyperlipidemia and hyperuricemia. Yet other metabolic-related diseases or disorders of the invention include cachexia, wasting, AIDS-related weight loss, cancer-related weight loss, anorexia, and bulimia. In preferred embodiments, said individual is a mammal, preferably a human.

In related aspects, embodiments of the present invention includes methods of causing or inducing a desired biological response in an individual comprising the steps of: providing or administering to an individual a composition comprising a GMG-7A, GMG-7B, GMG-8, GMG-9, GMG-10, or GMG-11 polypeptide, wherein said biological response is selected from the group consisting of:

(a) modulating circulating (either blood, serum, or plasma) levels (concentration) of free fatty acids, wherein said modulating is preferably lowering;

(b) modulating circulating (either blood, serum or plasma) levels (concentration) of glucose, wherein said modulating is preferably lowering;

(c) modulating circulating (either blood, serum or plasma) levels (concentration) of triglycerides, wherein said modulating is preferably lowering;

(d) stimulating muscle lipid or free fatty acid oxidation;

(c) modulating leptin uptake in the liver or liver cells, wherein said modulating is preferably increasing;

(e) modulating the postprandial increase in plasma free fatty acids due to a high fat meal, wherein said modulating is preferably reducing;

(f) modulating ketone body production as the result of a high fat meal, wherein said modulating is preferably reducing or eliminating;

(g) increasing cell or tissue sensitivity to insulin, particularly muscle, adipose, liver or brain; and (h) inhibiting the progression from impaired glucose tolerance to insulin resistance;

and further wherein said biological response is significantly greater than, or at least 10%, 20%, 30%, 35%, 40%, 50% 75% 100% or 500% greater than, the biological response caused or induced by insulin alone at the same molar concentration. In further preferred embodiments, the present invention of said pharmaceutical or physiologically acceptable composition can be used as a method to control blood glucose in some persons with Non-Insulin Dependent Diabetes Mellitus (NIDDM, Type II diabetes) in combination with insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control body weight in some persons with Non-Insulin Dependent Diabetes Mellitus (NIDDM, Type II diabetes) in combination with insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control blood glucose in some persons with Non-Insulin Dependent Diabetes Mellitus (NIDDM, Type II diabetes) alone, without combination of insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) alone, without combination of insulin therapy.

In further preferred embodiments, the present invention of said pharmaceutical or physiologically acceptable composition can be used as a method to control body weight in some persons with Non-Insulin Dependent Diabetes Mellitus (NIDDM, Type II diabetes) alone, without combination of insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) alone, without combination of insulin therapy.

In a further preferred embodiment, the present invention may be used in complementary therapy of NIDDM patients to improve their weight or glucose control in combination with an insulin secretagogue (preferably oral form) or an insulin sensitising (preferably oral form) agent. Preferably, the oral insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of NIDDM patients alone, without an insulin secretagogue or an insulin sensitising agent.

In a further preferred embodiment, the present invention may be used in complementary therapy of IDDM patients to improve their weight or glucose control in combination with an insulin secretagogue (preferably oral form) or an insulin sensitising (preferably oral form) agent. Preferably, the insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of IDDM patients alone, without an insulin secretagogue or an insulin sensitising agent.

In a further preferred embodiment, the present invention may be administered either concomitantly or concurrently, with the insulin secretagogue or insulin sensitising agent for example in the form of separate dosage units to be used simultaneously, separately or sequentially (either before or after the secretagogue or either before or after the sensitising agent). Accordingly, the present invention further provides for a composition of pharmaceutical or physiologically acceptable composition and an insulin secretagogue or insulin sensitising agent as a combined preparation for simultaneous, separate or sequential use for the improvement of body weight or glucose control in NIDDM or IDDM patients.

In further preferred embodiments, the present invention of said pharmaceutical or physiologically acceptable composition further provides a method for the use as an insulin sensitiser.

In further preferred embodiments, the present invention of said pharmaceutical or physiologically acceptable composition can be used as a method to improve insulin sensitivity in some persons with Non-Insulin Dependent Diabetes Mellitus (NIDDM, Type II diabetes) in combination with insulin therapy.

In further preferred embodiments, the present invention of said pharmaceutical or physiologically acceptable composition can be used as a method to improve insulin sensitivity in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to improve insulin sensitivity in some persons with Non-Insulin Dependent Diabetes Mellitus (NIDDM, Type II diabetes) without insulin therapy.

In an eighth aspect, the invention features a method of making the GMG-7A, GMG-7B, GMG-8, GMG-9, GMG-10, and GMG-11 polypeptides described in the first aspect, wherein said method is selected from the group consisting of: proteolytic cleavage, recombinant methodology and artificial synthesis.

In a ninth aspect, the present invention provides a method of making a recombinant GMG-7A, GMG-7B, GMG-8, GMG-9, GMG-10, or GMG-11 polypeptide fragment or a full length GMG-7A, GMG-7B, GMG-8, GMG-9, GMG-10, or GMG-11 polypeptide, the method comprising providing a transgenic, non-human mammal whose milk contains said recombinant GMG-7A, GMG-7B, GMG-8, GMG-9, GMG-10, or GMG-11 polypeptide fragment or full length protein, and purifying said recombinant GMG-7A, GMG-7B, GMG-8, GMG-9, GMG-10, or GMG-11 polypeptide fragment or said full-length GMG-7A, GMG-7B, GMG-8, GMG-9, GMG-10, or GMG-11 polypeptide from the milk of said non-human mammal. In one embodiment, said non-human mammal is a cow, goat, sheep, rabbit, or mouse. In another embodiment, the method comprises purifying a recombinant full-length GMG-7A, GMG-7B, GMG-8, GMG-9, GMG-10, or GMG-11 polypeptide from said milk, and further comprises cleaving said protein in vitro to obtain a desired GMG-7A, GMG-7B, GMG-8, GMG-9, GMG-10, or GMG-11 polypeptide fragment.

In a tenth aspect, the invention features a purified or isolated antibody capable of specifically binding to a polypeptide of the present invention. In one aspect of this embodiment, the antibody is capable of binding to a polypeptide comprising at least 6 consecutive amino acids, at least 8 consecutive amino acids, or at least 10 consecutive amino acids of the sequence of one of the polypeptide sequences described in SEQ ID NO: 2, 4, 6, 8, 10, or 12.

In an eleventh aspect, the invention features a use of the polypeptide described in the first aspect for treatment of metabolic-related diseases and disorders and/or reducing or increasing body mass. Preferably, said metabolic-related diseases and disorders are selected from the group consisting of obesity, insulin resistance, atherosclerosis, atheromatous disease, heart disease, hypertension, stroke, Syndrome X, non-insulin-dependent diabetes and Type II diabetes. Type II diabetes-related complications to be treated by the methods of the invention include microangiopathic lesions, ocular lesions, and renal lesions. Heart disease includes, but is not limited to, cardiac insufficiency, coronary insufficiency, and high blood pressure. Other metabolic-related disorders to be treated by compounds of the invention include hyperlipidemia and hyperuricemia. Yet other metabolic-related diseases or disorders of the invention include cachexia, wasting, AIDS-related weight loss, anorexia, and bulimia. In preferred embodiments, said individual is a mammal, preferably a human.

In a twelfth aspect, the invention provides a polypeptide of the first aspect of the invention, or a composition of the fifth aspect of the invention, for use in a method of treatment of the human or animal body.

In a thirteenth aspect, the invention features methods of reducing body weight for cosmetic purposes comprising providing to an individual said pharmaceutical or physiologically acceptable composition described in the fifth aspect, or a polypeptide described in the first aspect. Preferably, for said reducing body weight said individual has a BMI of at least 20 and no more than 25. Alternatively, for said increasing body weight said individual preferably has a BMI of at least 15 and no more than 20.

In a fourteenth aspect, the invention features the pharmaceutical or physiologically acceptable composition described in the fifth aspect for reducing body mass and/or for treatment or prevention of metabolic-related diseases or disorders. Preferably, said metabolic-related disease or disorder is selected from the group consisting of obesity, impaired glucose tolerance, insulin resistance, atherosclerosis, atheromatous disease, heart disease, hypertension, stroke, Syndrome X, non-insulin-dependent diabetes and Type II diabetes. Type II diabetes-related complications to be treated by the methods of the invention include microangiopathic lesions, ocular lesions, and renal lesions. Heart disease includes, but is not limited to, cardiac insufficiency, coronary insufficiency, and high blood pressure. Other metabolic-related disorders to be treated by compounds of the invention include hyperlipidemia and hyperuricemia. Yet other metabolic-related diseases or disorders of the invention include cachexia, wasting, AIDS-related weight loss, cancer-related weight loss, anorexia, and bulimia. In preferred embodiments, said individual is a mammal, preferably a human. In preferred embodiments, the identification of said individuals to be treated with said pharmaceutical or physiologically acceptable composition comprises genotyping GMG-7A, GMG-7B, GMG-8, GMG-9, GMG-10, or GMG-11 single nucleotide polymorphisms (SNPs) or measuring GMG-7A, GMG-7B, GMG-8, GMG-9, GMG-10, or GMG-11 polypeptides or mRNA levels in clinical samples from said individuals. Preferably, said clinical samples are selected from the group consisting of blood, serum, plasma, urine, and saliva.

In a fifteenth aspect, the invention features the pharmaceutical or physiologically acceptable composition described in the fifth aspect for reducing body weight for cosmetic reasons.

In a sixteenth aspect, the invention features methods of treating insulin resistance comprising providing to an individual said pharmaceutical or physiologically acceptable composition described in the fifth aspect, or a polypeptide described in the first aspect.

In a seventeenth aspect, the invention features the pharmaceutical or physiologically acceptable composition described in the fifth aspect in a method of treating individuals with normal glucose tolerance (NGT) who are obese or who have fasting hyperinsulinemia, or who have both.

In further preferred embodiments, the invention features the pharmaceutical or physiologically acceptable composition described in the fifth aspect in a method of treating individuals with gestational diabetes. Gestational diabetes refers to the development of diabetes in an individual during pregnancy, usually during the second or third trimester of pregnancy.

In further preferred embodiments, the invention features the pharmaceutical or physiologically acceptable composition described in the fifth aspect in a method of treating individuals with impaired fasting glucose (IFG). Impaired fasting glucose (IFG) is that condition in which fasting plasma glucose levels in an individual are elevated but not diagnostic of overt diabetes, i.e. plasma glucose levels of less than 126 mg/dl and less than or equal to 110 mg/dl.

In further preferred embodiments, the invention features the pharmaceutical or physiologically acceptable composition described in the fifth aspect in a method of treating and preventing impaired glucose tolerance (IGT) in an individual. By providing therapeutics and methods for reducing or preventing IGT, i.e., for normalizing insulin resistance, the progression to NIDDM can be delayed or prevented. Furthermore, by providing therapeutics and methods for reducing or preventing insulin resistance, the invention provides methods for reducing and/or preventing the appearance of Insulin-Resistance Syndrome.

In further preferred embodiments, the invention features the pharmaceutical or physiologically acceptable composition described in the fifth aspect in a method of treating a subject having polycystic ovary syndrome (PCOS). PCOS is among the most common disorders of premenopausal women, affecting 5-10% of this population. Insulin-sensitizing agents, e.g., troglitazone, have been shown to be effective in PCOS and that, in particular, the defects in insulin action, insulin secretion, ovarian steroidogenosis and fibrinolysis are improved (Ehrman et al. (1997) J Clin Invest 100:1230), such as in insulin-resistant humans. Accordingly, the invention provides methods for reducing insulin resistance, normalizing blood glucose thus treating and/or preventing PCOS.

In further preferred embodiments, the invention features the pharmaceutical or physiologically acceptable composition described in the fifth aspect in a method of treating a subject having insulin resistance.

In further preferred embodiments, a subject having insulin resistance is treated according to the methods of the invention to reduce or cure the insulin-resistance. As insulin resistance is also often associated with infections and cancer, prevention or reducing insulin resistance according to the methods of the invention may prevent or reduce infections and cancer.

In further preferred embodiment, the methods of the invention are used to prevent the development of insulin resistance in a subject, e.g., those known to have an increased risk of developing insulin-resistance.

Thus, any of the above-described tests or other tests known in the art can be used to determine that a subject is insulin-resistant, which patient can then be treated according to the methods of the invention to reduce or cure the insulin-resistance. Alternatively, the methods of the invention can also be used to prevent the development of insulin resistance in a subject, e.g., those known to have an increased risk of developing insulin-resistance.

In an eighteenth aspect, the invention features a method of preventing or treating an metabolic-related disease or disorder comprising providing or administering to an individual in need of such treatment said pharmaceutical or physiologically acceptable composition described in the fifth aspect. In preferred embodiments, the identification of said individuals in need of such treatment to be treated with said pharmaceutical or physiologically acceptable composition comprises genotyping GMG-7A, GMG-7B, GMG-8, GMG-9, GMG-10, or GMG-11 single nucleotide polymorphisms (SNPs) or measuring GMG-7A, GMG-7B, GMG-8, GMG-9, GMG-10, or GMG-11 polypeptide or mRNA levels in clinical samples from said individuals. Preferably, said clinical samples are selected from the group consisting of blood, serum, plasma, urine, and saliva. Preferably, said metabolic-related disease or disorder is selected from the group consisting of obesity, impaired glucose tolerance, insulin resistance, atherosclerosis, atheromatous disease, heart disease, hypertension, stroke, Syndrome X, non-insulin-dependent diabetes and Type II diabetes. Type II diabetes-related complications to be treated by the methods of the invention include microangiopathic lesions, ocular lesions, and renal lesions. Heart disease includes, but is not limited to, cardiac insufficiency, coronary insufficiency, and high blood pressure. Other metabolic-related disorders to be treated by compounds of the invention include hyperlipidemia and hyperuricemia. Yet other metabolic-related diseases or disorders of the invention include cachexia, wasting, FIV-related weight loss, cancer-related weight loss, anorexia, and bulimia. In preferred embodiments, said individual is a mammal, preferably non-human, preferably a cat or a dog.

In a nineteenth aspect, the invention features a method of using a GMG-7A, GMG-7B, GMG-8, GMG-9, GMG-10, or GMG-11 polypeptide or polypeptide fragment to screen compounds for one or more antagonists of GMG-7A, GMG-7B, GMG-8, GMG-9, GMG-10, or GMG-11 polypeptide or polypeptide fragment activity, wherein said activity is selected from but not restricted to lipid partitioning, lipid metabolism, and insulin-like activity.

In preferred embodiment, said compound is selected from but is not restricted to small molecular weight organic or inorganic compound, protein, peptide, carbohydrate, or lipid.

In a preferred aspect of the methods above and disclosed herein, the amount of GMG-7A, GMG-7B, GMG-8, GMG-9, GMG-10, or GMG-11 polypeptide or polynucleotide administered to an individual is sufficient to bring circulating (blood, serum, or plasma) levels (concentration) of GMG-7A, GMG-7B, GMG-8, GMG-9, GMG-10, or GMG-11 polypeptides to their normal levels (levels in non-obese individuals). "Normal levels" may be specified as the total concentration of all circulating GMG-7A, GMG-7B, GMG-8, GMG-9, GMG-10, or GMG-11 polypeptides (full-length GMG-7A, GMG-7B, GMG-8, GMG-9, GMG-10, or GMG-11 proteins and fragments thereof) or the concentration of all circulating proteolytically cleaved GMG-7A, GMG-7B, GMG-8, GMG-9, GMG-10, or GMG-11 polypeptides only.

In a further preferred aspect of the methods above and disclosed herein, weight loss is due in part or in whole to a decrease in mass of either a) subcutaneous adipose tissue and/or b) visceral (omental) adipose tissue.

Full-length GMG-7A, GMG-7B, GMG-8, GMG-9, GMG-10, or GMG-11 polypeptides and polynucleotides encoding the same may be specifically substituted for a GMG-7A, GMG-7B, GMG-8, GMG-9, GMG-10, or GMG-11 polypeptide fragment or polynucleotide encoding the same in any embodiment of the present invention.

DETAILED DESCRIPTION OF THE SEQUENCE LISTING

SEQ ID NO:1 represents the cDNA sequence of GMG-7A.

SEQ ID NO:2 represents the amino acid sequence encoded by the cDNA of SEQ ID NO:1.

SEQ ID NO:3 represents the cDNA sequence of GMG-7B.

SEQ ID NO:4 represents the amino acid sequence encoded by the cDNA of SEQ ID NO:3.

SEQ ID NO:5 represents the polynucleotide sequence of GMG-8.

SEQ ID NO:6 represents the amino acid sequence encoded by the polynucleotide sequence of SEQ ID NO:5.

SEQ ID NO:7 represents the cDNA sequence of GMG-9.

SEQ ID NO:8 represents the amino acid sequence encoded by the cDNA of SEQ ID NO:7.

SEQ ID NO:9 represents the cDNA sequence of GMG-10.

SEQ ID NO:10 represents the amino acid sequence encoded by the cDNA of SEQ ID NO:9.

SEQ ID NO:11 represents the cDNA sequence of GMG-11.

SEQ ID NO:12 represents the amino acid sequence encoded by the cDNA of SEQ ID NO:11.

DETAILED DESCRIPTION OF THE INVENTION

Before describing the invention in greater detail, the following definitions are set forth to illustrate and define the meaning and scope of the terms used to describe the invention herein.

As used interchangeably herein, the terms "oligonucleotides", and "polynucleotides" and nucleic acid include RNA, DNA, or RNA/DNA hybrid sequences of more than one nucleotide in either single chain or duplex form. The terms encompass "modified nucleotides" which comprise at least one modification, including by way of example and not limitation: (a) an alternative linking group, (b) an analogous form of purine, (c) an analogous form of pyrimidine, or (d) an analogous sugar. For examples of analogous linking groups, purines, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

The terms polynucleotide construct, recombinant polynucleotide and recombinant polypeptide are used herein consistently with their use in the art. The terms "upstream" and "downstream" are also used herein consistently with their use in the art. The terms "base paired" and "Watson & Crick base paired" are used interchangeably herein and consistently with their use in the art. Similarly, the terms "complementary", "complement thereof", "complement", "complementary polynucleotide", "complementary nucleic acid" and "complementary nucleotide sequence" are used interchangeably herein and consistently with their use in the art.

The term "purified" is used herein to describe a polynucleotide or polynucleotide vector of the invention that has been separated from other compounds including, but not limited to, other nucleic acids, carbohydrates, lipids and proteins (such as the enzymes used in the synthesis of the polynucleotide). Purified can also refer to the separation of covalently closed polynucleotides from linear polynucleotides, or vice versa, for example. A polynucleotide is substantially pure when at least about 50%, 60%, 75%, or 90% of a sample contains a single polynucleotide sequence. In some cases this involves a determination between conformations (linear versus covalently closed). A substantially pure polynucleotide typically comprises about 50, 60, 70, 80, 90, 95, 99% weight/weight of a nucleic acid sample. Polynucleotide purity or homogeneity may be indicated by a number of means well known in the art, such as agarose or polyacrylamide gel electrophoresis of a sample, followed by visualizing a single polynucleotide band upon staining the gel. For certain purposes, higher resolution can be achieved by using HPLC or other means well known in the art.

Similarly, the term "purified" is used herein to describe a polypeptide of the invention that has been separated from other compounds including, but not limited to, nucleic acids, lipids, carbohydrates and other proteins. In some preferred embodiments, a polypeptide is substantially pure when at least about 50%, 60%, 75%, 85%, 90%, 95%, 96%, 97%, 98%, 99%, or 99.5% of the polypeptide molecules of a sample have a single amino acid sequence. In some preferred embodiments, a substantially pure polypeptide typically comprises about 50%, 60%, 70%, 80%, 90% 95%, 96%, 97%, 98%, 99% or 99.5% weight/weight of a protein sample. Polypeptide purity or homogeneity is indicated by a number of methods well known in the art, such as agarose or polyacrylamide gel electrophoresis of a sample, followed by visualizing a single polypeptide band upon staining the gel. For certain purposes, higher resolution can be achieved by using HPLC or other methods well known in the art.

Further, as used herein, the term "purified" does not require absolute purity; rather, it is intended as a relative definition. Purification of starting material or natural material to at least one order of magnitude, preferably two or three orders, and more preferably four or five orders of magnitude is expressly contemplated. Alternatively, purification may be expressed as "at least" a percent purity relative to heterologous polynucleotides (DNA, RNA or both) or polypeptides. As a preferred embodiment, the polynucleotides or polypeptides of the present invention are at least; 10%, 20%, 30%, 40%, 50%, 60%, 70%, 80%, 90%, 95%, 96%, 96%, 98%, 99%, 99.5% or 100% pure relative to heterologous polynucleotides or polypeptides. As a further preferred embodiment the polynucleotides or polypeptides have an "at least" purity ranging from any number, to the thousandth position, between 90% and 100% (e.g., at least 99.995% pure) relative to heterologous polynucleotides or polypeptides. Additionally, purity of the polynucleotides or polypeptides may be expressed as a percentage (as described above) relative to all materials and compounds other than the carrier solution. Each number, to the thousandth position, may be claimed as individual species of purity.

The term "isolated" requires that the material be removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

Specifically excluded from the definition of "isolated" are: naturally occurring chromosomes (e.g., chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a 5' EST makes up less than 5% (or alternatively 1%, 2%, 3%, 4%, 10%, 25%, 50%, 75%, or 90%, 95%, or 99%) of the number of nucleic acid inserts in the vector molecules. Further specifically excluded are whole cell genomic DNA or whole cell RNA preparations (including said whole cell preparations which are mechanically sheared or enzymatically digested). Further specifically excluded are the above whole cell preparations as either an in vitro preparation or as a heterogeneous mixture separated by electrophoresis (including blot transfers of the same) wherein the polynucleotide of the invention have not been further separated from the heterologous polynucleotides in the electrophoresis medium (e.g., further separating by excising a single band from a heterogeneous band population in an agarose gel or nylon blot).

The term "primer" denotes a specific oligonucleotide sequence which is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "probe" denotes a defined nucleic acid segment that can be used to identify a specific polynucleotide sequence present in a sample, said nucleic acid segment comprising a nucleotide sequence complementary to the specific polynucleotide sequence to be identified.

The term "polypeptide" refers to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

Without being limited by theory, the compounds/polypeptides of the invention are capable of modulating the partitioning of dietary lipids between the liver and peripheral tissues, and thus of treating "diseases involving the partitioning of dietary lipids between the liver and peripheral tissues." The term "peripheral tissues" is meant to include muscle and adipose tissue. In preferred embodiments, the compounds/polypeptides of the invention partition the dietary lipids toward the muscle. In alternative preferred embodiments, the dietary lipids are partitioned toward the adipose tissue. In other preferred embodiments, the dietary lipids are partitioned toward the liver. In yet other preferred embodiments, the compounds/polypeptides of the invention increase or decrease the oxidation of dietary lipids, preferably free fatty acids (FFA) by the muscle. Dietary lipids include, but are not limited to triglycerides and free fatty acids.

Preferred diseases believed to involve the partitioning of dietary lipids include obesity and obesity-related diseases and disorders such as obesity, impaired glucose tolerance, insulin resistance, atherosclerosis, atheromatous disease, heart disease, hypertension, stroke, Syndrome X, Non-Insulin Dependent Diabetes Mellitus (NIDDM, or Type II diabetes) and Insulin Dependent Diabetes Mellitus (IDDM, or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, cancer-related weight loss, anorexia, and bulimia.

The term "heterologous", when used herein, is intended to designate any polypeptide or polynucleotide other than a GMG-7A, GMG-7B, GMG-8, GMG-9, GMG-10, or GMG-11 polypeptide or a polynucleotide encoding a GMG-7A, GMG-7B, GMG-8, GMG-9, GMG-10, or GMG-11 polypeptide of the present invention.

The terms "comprising", "consisting of" and "consisting essentially of" are defined according to their standard meaning. A defined meaning set forth in the M.P.E.P. controls over a defined meaning in the art and a defined meaning set forth in controlling Federal Circuit case law controls over a meaning set forth in the M.P.E.P. With this in mind, the terms may be substituted for one another throughout the instant application in order to attach the specific meaning associated with each term.

The term "host cell recombinant for" a particular polynucleotide of the present invention, means a host cell that has been altered by the hands of man to contain said polynucleotide in a way not naturally found in said cell. For example, said host cell may be transiently or stably transfected or transduced with said polynucleotide of the present invention.

The term "obesity" as used herein is defined in the WHO classifications of weight (Kopelman (2000) Nature 404: 635643). Underweight is less than 18.5 (thin); Healthy is 18.5-24.9 (normal); grade 1 overweight is 25.0-29.9 (overweight); grade 2 overweight is 30.0-39.0 (obesity); grade 3 overweight is greater than or equal to 40.0 BMI. BMI is body mass index (morbid obesity) and is $kg/m^2$. Waist circumference can also be used to indicate a risk of metabolic complications where in men a circumference of greater than or equal to 94 cm indicates an increased risk and greater than or equal to 102 cm indicates a substantially increased risk. Similarly for women, greater than or equal to 88 cm indicates an increased risk, and greater than or equal to 88 cm indicates a substantially increased risk. The waist circumference is measured in cm at midpoint between lower border of ribs and upper border of the pelvis. Other measures of obesity include, but are not limited to, skinfold thickness which is a measurement in cm of skinfold thickness using calipers, and bioimpedance, which is based on the principle that lean mass conducts current better than fat mass because it is primarily an electrolyte solution; measurement of resistance to a weak current (impedance) applied across extremities provides an estimate of body fat using an empirically derived equation.

The term "diabetes" as used herein is intended to encompass the usual diagnosis of diabetes made from any of the methods included, but not limited to, the following list: symptoms of diabetes (eg. polyuria, polydipsia, polyphagia) plus casual plasma glucose levels of greater than or equal to 200 mg/dl, wherein casual plasma glucose is defined any time of the day regardless of the timing of meal or drink consumption; 8 hour fasting plasma glucose levels of less than or equal to 126 mg/dl; and plasma glucose levels of greater than or equal to 200 mg/dl 2 hours following oral administration of 75 g anhydrous glucose dissolved in water.

The term "impaired glucose tolerance (IGT)" as used herein is intended to indicate that condition associated with insulin-resistance that is intermediate between frank, NIDDM and normal glucose tolerance (NGT). A high percentage of the IGT population is known to progress to NIDDM relative to persons with normal glucose tolerance (Sad et al., New Engl J Med 1988; 319:1500-6). Thus, by providing therapeutics and methods for reducing or preventing IGT, i.e., for normalizing insulin resistance, the progression to NIDDM can be delayed or prevented. IGT is diagnosed by a procedure wherein an affected person's postprandial glucose response is determined to be abnormal as assessed by 2-hour postprandial plasma glucose levels. In this test, a measured amount of glucose is given to the patient and blood glucose levels measured regular intervals, usually every half hour for the first two hours and every hour thereafter. In a "normal" or non-IGT individual, glucose levels rise during the first two hours to a level less than 140 mg/dl and then drop rapidly. In an IGT individual, the blood glucose levels are higher and the drop-off level is at a slower rate.

The term "Insulin-Resistance Syndrome" as used herein is intended to encompass the cluster of abnormalities resulting from an attempt to compensate for insulin resistance that sets in motion a series of events that play an important role in the development of both hypertension and coronary artery disease (CAD), such as premature atherosclerotic vascular disease. Increased plasma triglyceride and decreased HDL-cholesterol concentrations, conditions that are known to be associated with CAD, have also been reported to be associated with insulin resistance. Thus, by providing therapeutics and methods for reducing or preventing insulin resistance, the invention provides methods for reducing and/or preventing the appearance of insulin-resistance syndrome.

The term "polycystic ovary syndrome (PCOS)" as used herein is intended to designate that etiologically unassigned disorder of premenopausal women, affecting 5-10% of this population, characterized by hyperandrogenism, chronic anovulation, defects in insulin action, insulin secretion, ovarian steroidogenesis and fibrinolysis. Women with PCOS frequently are insulin resistant and at increased risk to develop glucose intolerance or NIDDM in the third and fourth decades of life (Dunaif et al. (1996) J Clin Endocrinol Metab 81:3299). Hyperandrogenism also is a feature of a variety of diverse insulin-resistant states, from the type A syndrome, through leprechaunism and lipoatrophic diabetes, to the type B syndrome, when these conditions occur in premenopausal women. It has been suggested that hyperinsulinemia per se causes hyperandrogenism. Insulin-sensitizing agents, e.g., troglitazone, have been shown to be effective in PCOS and that, in particular, the defects in insulin action, insulin secretion, ovarian steroidogenesis and fibrinolysis are improved (Ehrman et al. (1997) J Clin Invest 100:1230), such as in insulin-resistant humans.

The term "insulin resistance" as used herein is intended to encompass the usual diagnosis of insulin resistance made by any of a number of methods, including but not restricted to: the intravenous glucose tolerance test or measurement of the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. Another way to do this is to follow the approach as disclosed in The New England Journal of Medicine, No. 3, pp. 1188 (1995), i.e. to select obesity as an initial criterion for entry into the treatment group. Some obese subjects have impaired glucose tolerance (IGT) while others have normal glucose tolerance (NGT). Since essentially all obese subjects are insulin resistant, i.e. even the NGT obese subjects are insulin resistant and have fasting hyperinsulinemia. Therefore, the target of the treatment according to the present invention can be defined as NGT individuals who are obese or who have fasting hyperinsulinemia, or who have both.

A diagnosis of insulin resistance can also be made using the euglycemic glucose clamp test. This test involves the simultaneous administration of a constant insulin infusion and a variable rate glucose infusion. During the test, which lasts 3-4 hours, the plasma glucose concentration is kept constant at euglycemic levels by measuring the glucose level every 5-10 minutes and then adjusting the variable rate glucose infusion to keep the plasma glucose level unchanged. Under these circumstances, the rate of glucose entry into the bloodstream is equal to the overall rate of glucose disposal in the body. The difference between the rate of glucose disposal in the basal state (no insulin infusion)

and the insulin infused state, represents insulin mediated glucose uptake. In normal individuals, insulin causes brisk and large increase in overall body glucose disposal, whereas in NIDDM subjects, this effect of insulin is greatly blunted, and is only 20-30% of normal. In insulin resistant subjects with either IGT or NGT, the rate of insulin stimulated glucose disposal is about half way between normal and NIDDM. For example, at a steady state plasma insulin concentration of about 100 uU/ml (a physiologic level) the glucose disposal rate in normal subjects is about 7 mg/kg/min. In NIDDM subjects, it is about 2.5 mg/.kg/min., and in patients with IGT (or insulin resistant subjects with NGT) it is about 4-5 mg/kg/min. This is a highly reproducible and precise test, and can distinguish patients within these categories. It is also known that as subjects become more insulin resistant, the fasting insulin level rises. There is an excellent positive correlation between the height of the fasting insulin level and the magnitude of the insulin resistance as measured by euglycemic glucose clamp tests and, therefore, this provides the rationale for using fasting insulin levels as a surrogate measure of insulin resistance.

The term "agent acting on the partitioning of dietary lipids between the liver and peripheral tissues" refers to a compound or polypeptide of the invention that modulates the partitioning of dietary lipids between the liver and the peripheral tissues as previously described. Preferably, the agent increases or decreases the oxidation of dietary lipids, preferably free fatty acids (FFA) by the muscle. Preferably the agent decreases or increases the body weight of individuals or is used to treat or prevent an obesity-related disease or disorder such as obesity, impaired glucose tolerance, insulin resistance, atherosclerosis, atheromatous disease, heart disease, hypertension, stroke, Syndrome X, Non-Insulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, cancer-related weight loss, anorexia, and bulimia.

The terms "response to an agent acting on the partitioning of dietary lipids between the liver and peripheral tissues" refer to drug efficacy, including but not limited to, ability to metabolize a compound, ability to convert a pro-drug to an active drug, and the pharmacokinetics (absorption, distribution, elimination) and the pharmacodynamics (receptor-related) of a drug in an individual.

The terms "side effects to an agent acting on the partitioning of dietary lipids between the liver and peripheral tissues" refer to adverse effects of therapy resulting from extensions of the principal pharmacological action of the drug or to idiosyncratic adverse reactions resulting from an interaction of the drug with unique host factors. "Side effects to an agent acting on the partitioning of dietary lipids between the liver and peripheral tissues" can include, but are not limited to, adverse reactions such as dermatologic, hematologic or hepatologic toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, and shock.

The term "GMG-7A-, GMG-7B-, GMG-8-, GMG-9-, GMG-10-, or GMG-11-related diseases and disorders" as used herein refers to any disease or disorder comprising an aberrant functioning of GMG-7A, GMG-7B, GMG-8, GMG-9, GMG-10, or GMG-11, or which could be treated or prevented by modulating GMG-7A, GMG-7B, GMG-8, GMG-9, GMG-10, or GMG-11 levels or activity. "Aberrant functioning of GMG-7A, GMG-7B, GMG-8, GMG-9, GMG-10, or GMG-11" includes, but is not limited to, aberrant levels of expression of GMG-7A, GMG-7B, GMG-8, GMG-9, GMG-10, or GMG-11 (either increased or decreased, but preferably decreased), aberrant activity of GMG-7A, GMG-7B, GMG-8, GMG-9, GMG-10, or GMG-11 (either increased or decreased), and aberrant interactions with ligands or binding partners (either increased or decreased). By "aberrant" is meant a change from the type, or level of activity seen in normal cells, tissues, or patients, or seen previously in the cell, tissue, or patient prior to the onset of the illness. In preferred embodiments, these GMG-7A-, GMG-7B-, GMG-8-, GMG-9-, GMG-10-, or GMG-11-related diseases and disorders include obesity and the metabolic-related diseases and disorders described previously.

The term "cosmetic treatments" is meant to include treatments with compounds or polypeptides of the invention that increase or decrease the body mass of an individual where the individual is not clinically obese or clinically thin. Thus, these individuals have a body mass index (BMI) below the cut-off for clinical obesity (e.g. below 25 kg/m$^2$) and above the cut-off for clinical thinness (e.g. above 18.5 kg/m$^2$). In addition, these individuals are preferably healthy (e.g. do not have an metabolic-related disease or disorder of the invention). "Cosmetic treatments" are also meant to encompass, in some circumstances, more localized increases in adipose tissue, for example, gains or losses specifically around the waist or hips, or around the hips and thighs, for example. These localized gains or losses of adipose tissue can be identified by increases or decreases in waist or hip size, for example.

The term "preventing" as used herein refers to administering a compound prior to the onset of clinical symptoms of a disease or condition so as to prevent a physical manifestation of aberrations associated with obesity or GMG-7A, GMG-7B, GMG-8, GMG-9, GMG-10, or GMG-11.

The term "treating" as used herein refers to administering a compound after the onset of clinical symptoms.

The term "in need of treatment" as used herein refers to a judgment made by a caregiver (e.g. physician, nurse, nurse practitioner, etc in the case of humans; veterinarian in the case of animals, including non-human mammals) that an individual or animal requires or will benefit from treatment. This judgment is made based on a variety of factors that are in the realm of a caregiver's expertise, but that include the knowledge that the individual or animal is ill, or will be ill, as the result of a condition that is treatable by the compounds of the invention.

The term "perceives a need for treatment" refers to a sub-clinical determination that an individual desires to reduce weight for cosmetic reasons as discussed under "cosmetic treatment" above. The term "perceives a need for treatment" in other embodiments can refer to the decision that an owner of an animal makes for cosmetic treatment of the animal.

The term "individual" or "patient" as used herein refers to any animal, including mammals, preferably mice, rats, other rodents, rabbits, dogs, cats, swine, cattle, sheep, horses, or primates, and most preferably humans. The term may specify male or female or both, or exclude male or female.

The term "non-human animal" refers to any non-human vertebrate, including birds and more usually mammals, preferably primates, animals such as swine, goats, sheep, donkeys, horses, cats, dogs, rabbits or rodents, more preferably rats or mice. Both the terms "animal" and "mammal" expressly embrace human subjects unless preceded with the term "non-human".

GMG-7A, GMG-7B, GMG-8, GMG-9, GM 10, or GMG-11 polypeptides are able to significantly reduce the postprandial response of plasma free fatty acids, glucose, and triglycerides in mammals fed a high fat/sucrose meal, while not affecting levels of leptin, insulin or glucagon. In addition, GMG-7A, GMG-7B, GMG-8, GMG-9, GMG-10, or GMG-11 polypeptides modulate muscle free fatty acid oxidation in vitro and ex vivo, preferably increase oxidation. Further, GMG-7A, GMG-7B, GMG-8, GMG-9, GMG-O, or GMG-11 polypeptides of the invention modulate weight gain in mammals that are fed a high fat/sucrose diet.

The instant invention encompasses the use of GMG-7A, GMG-7B, GMG-8, GMG-9, GMG-10, or GMG-11 polypeptides in the partitioning of free fatty acid (FFA) and as an important new tool to control energy homeostasis. Of the tissues that can significantly remove lipids from circulation and cause FFA oxidation, muscle is believed to be quantitatively the most important.

PREFERRED EMBODIMENTS OF THE INVENTION

I. GMG-7A, GMG-7B, GMG-8, GMG-9, GMG-10, or GMG-11 Polypeptides of the Invention GMG-7A, GMG-7B, GMG-8, GMG-9, GMG-10, or GMG-11 polypeptides have been identified that have measurable activity in vitro and in vivo. These activities include, but are not limited to, modulation, preferably reduction, of the postprandial response of plasma free fatty acids, glucose, and triglycerides in mammals fed a high fat/sucrose meal (Example 6), change, preferably an increase, in muscle free fatty acid oxidation in vitro and ex vivo (Example 10), and sustained weight loss in mammals on a high fat/sucrose diet. Other assays for GMG-7A, GMG-7B, GMG-8, GMG-9, GMG-10, or GMG-11 polypeptide activity in vitro and in vivo are also provided (Examples 2, 5, 7, 9, 11, for example), and equivalent assays can be designed by those with ordinary skill in the art.

The term "GMG-7A, GMG-7B, GMG-8, GMG-9, GMG-10, or GMG-11 polypeptides" includes both the "full-length" polypeptide and fragments of the "full-length" GMG-7A, GMG-7B, GMG-8, GMG-9, GMG-10, or GMG-11 polypeptides (although each of the above species may be particularly specified).

By "intact" or "full-length" GMG-7A, GMG-7B, GMG-8, GMG-9, GMG-10, or GMG-11 polypeptides as used herein is meant the full-length polypeptide sequence of any GMG-7A, GMG-7B, GMG-8, GMG-9, GMG-10, or GMG-11 polypeptide, from the N-terminal methionine to the C-terminal stop codon. Examples of intact or full-length GMG-7A, GMG-7B, GMG-8, GMG-9, GMG-10, or GMG-11 polypeptides are found in the sequence listing.

The term "metabolic-related activity" as used herein refers to at least one, and preferably all, of the activities described herein for GMG-7A, GMG-7B, GMG-8, GMG-9, GMG-10, or GMG-11 polypeptides. Assays for the determination of these activities are provided herein (e.g. Examples 2, 5-7, 9-11), and equivalent assays can be designed by those with ordinary skill in the art. Optionally, "metabolic-related activity" can be selected from the group consisting of lipid partitioning, lipid metabolism, and insulin-like activity, or an activity within one of these categories. By "lipid partitioning" activity is meant the ability to effect the location of dietary lipids among the major tissue groups including, adipose tissue, liver, and muscle. GMG-7A, GMG-7B, GMG-8, GMG-9, GMG-10, or GMG-11 polypeptides of the invention play a role in the partitioning of lipids to the muscle, liver or adipose tissue. By "lipid metabolism" activity is meant the ability to influence the metabolism of lipids. GMG-7A, GMG-7B, GMG-8, GMG-9, GMG-10, or GMG-11 polypeptides of the invention have the ability to affect the level of free fatty acids in the plasma as well as to modulate, preferably increase, the metabolism of lipids in the muscle through free fatty acid oxidation experiments (Examples 2, 6, 8, 9, 10) and to transiently affect the levels of triglycerides in the plasma and the muscle (Examples 6, 8, 11). By "insulin-like" activity is meant the ability of GMG-7A, GMG-7B, GMG-8, GMG-9, GMG-10, or GMG-11 polypeptides to modulate the levels of glucose in the plasma. GMG-7A, GMG-7B, GMG-8, GMG-9, GMG-10, or GMG-11 polypeptides do not significantly impact insulin levels but do impact glucose levels similarly to the effects of insulin (Examples 7 & 8). These effects may vary in the presence of the intact (full-length) GMG-7A, GMG-7B, GMG-8, GMG-9, GMG-10, or GMG-11 polypeptides or may be significantly greater in the presence of the GMG-7A, GMG-7B, GMG-8, GMG-9, GMG-10, or GMG-11 polypeptide fragments compared with the full-length GMG-7A, GMG-7B, GMG-8, GMG-9, GMG-10, or GMG-11 polypeptides.

The term "significantly greater" as used herein refers to a comparison of the activity of a GMG-7A, GMG-7B, GMG-8, GMG-9, GMG-10, or GMG-11 polypeptide in a metabolic-related assay compared with untreated cells in the same assay. By "significantly" as used herein is meant statistically significant as it is typically determined by those with ordinary skill in the art. For example, data are typically calculated as a mean±SEM, and a p-value $\leq 0.05$ is considered statistically significant. Statistical analysis is typically done using either the unpaired Student's t test or the paired Student's t test, as appropriate in each study. Examples of a significant change in activity as a result of the presence of a GMG-7A, GMG-7B, GMG-8, GMG-9, GMG-10, or GMG-11 polypeptide of the invention compared to untreated cells include an increase or a decrease in a given parameter of at least 5%, 10%, 15%, 20%, 25%, 30%, 35%, 40%, 45%, 50%, 55%, 60%, 65%, 70%, or 75%. One or more, but not necessarily all, of the measurable parameters will change significantly in the presence of GMG-7A, GMG-7B, GMG-8, GMG-9, GMG-10, or GMG-11 polypeptide as compared to untreated cells.

Representative "metabolic-related assays" are provided in the Examples. These assays include, but are not limited to, methods of measuring the postprandial response, methods of measuring free fatty acid oxidation, and methods of measuring weight modulation. In preferred embodiments, the post-prandial response is measured in non-human animals, preferably mice. In preferred embodiments changes in dietary lipids are measured, preferably free fatty acids and/or triglycerides. In other embodiments, other physiologic parameters are measured including, but not limited to, levels of glucose, insulin, and leptin. In other preferred embodiments, free fatty acid oxidation is measured in cells in vitro or ex vivo, preferably in muscle cells or tissue of non-human animals, preferably mice. In yet other preferred embodiments weight modulation is measured in human or non-human animals, preferably rodents (rats or mice), primates, canines, felines or procines. on a high fat/sucrose diet. Optionally, "metabolic-related activity" includes other activities not specifically identified herein. In general, "measurable parameters" relating to obesity and the field of metabolic research can be selected from the group consisting of free fatty acid levels, free fatty acid oxidation, triglyceride levels, glucose levels, insulin levels, leptin levels, food intake, weight, leptin and lipoprotein binding, uptake and degradation and lipolysis stimulated receptor (LSR) expression.

In these metabolic-related assays, preferred GMG-7A, GMG-7B, GM 8, GMG-9, GMG-10, or GMG-11 polypeptides would cause a significant change in at least one of the measurable parameters selected from the group consisting of post-prandial lipemia, free fatty acid levels, triglyceride levels, glucose levels, free fatty acid oxidation, and weight. Alternatively, preferred GMG-7A, GMG-7B, GMG-8, GMG-9, GMG-10, or GMG-11 polypeptides would have a significant change in at least one of the measurable parameters selected from the group consisting of an increase in LSR activity, an increase in leptin activity and an increase in lipoprotein activity. By "LSR" activity is meant expression of LSR on the surface of the cell, or in a particular conformation, as well as its ability to bind, uptake, and degrade leptin and lipoprotein. By "leptin" activity is meant its binding, uptake and degradation by LSR, as well as its transport across a blood brain barrier, and potentially these occurrences where LSR is not necessarily the mediating factor or the only mediating factor. Similarly, by "lipoprotein" activity is meant its binding, uptake and degradation by LSR, as well as these occurrences where LSR is not necessarily the mediating factor or the only mediating factor.

The invention is drawn, inter alia, to isolated, purified or recombinant GMG-7A, GMG-7B, GMG-8, GMG-9, GMG-10, or GMG-11 polypeptides. GMG-7A, GMG-7B, GMG-8, GMG-9, GMG-10, or GMG-11 polypeptides of the invention are useful for reducing or, using antagonists of GMG-7A, GMG-7B, GMG-8, GMG-9, GMG-10, or GMG-11 polypeptides, increasing body weight either as a cosmetic treatment or for treatment or prevention of metabolic-related diseases and disorders. GMG-7A, GMG-7B, GMG-8, GM 9, GMG-10, or GMG-11 polypeptides are also useful inter alia in screening assays for agonists or antagonists of GMG-7A, GMG-7B, GMG-8, GMG-9, GMG-10, or GMG-11 polypeptide activity; for raising GMG-7A, GMG-7B, GMG-8, GMG-9, GMG-10, or GMG-11 polypeptide-specific antibodies; and in diagnostic assays. When used for cosmetic treatments, or for the treatment or prevention of metabolic-related diseases, disorders or conditions, one or more GMG-7A, GMG-7B, GMG-8, GMG-9, GMG-10, or GMG-11 or GMG-7A, GMG-7B, GMG-8, GMG-9, GMG-10, or GMG-11 polypeptide fragments can be provided to a subject. Thus, various fragments of the full-length protein can be combined into a "cocktail" for use in the various treatment regimens.

The full-length GMG-7A, GMG-7B, GMG-8, GMG-9, GMG-10, or GMG-11 polypeptide is comprised of distinct regions including:

1. an N-terminal putative signal peptide sequence about from amino acids 1-27 of SEQ ID NO: 6, about from amino acids 1-24 of SEQ ID NO: 8, about from amino acids 1-23 of SEQ ID NO: 10, or about from amino acids 1-32 of SEQ ID NO: 12;

2. a collagen-like region about from amino acids 45-146 of SEQ ID NO: 10;

3. a C-terminal globular C1q homology domain about from amino acids 579-710 of SEQ ID NO: 2, about from amino acids 69-201 of SEQ ID NO: 6, about from amino acids 149-285 of SEQ ID NO: 10, or about from amino acids 70-205 of SEQ ID NO: 12; and 4. an N-terminally disposed truncated globular C1q homology domain about from amino acids 45-110 of SEQ ID NO: 8.

GMG-7A, GMG-7B, GMG-8, GMG-9, GMG-10, or GMG-11 polypeptides of the invention include variants, fragments, analogs and derivatives of the GMG-7A, GMG-7B, GMG-8, GMG-9, GMG-10, or GMG-11 polypeptides described above, including modified GMG-7A, GMG-7B, GMG-8, GMG-9, GMG-10, or GMG-11 polypeptides.

The GMG-7A, GMG-7B, GMG-8, GMG-9, GMG-10, or GMG-11 polypeptides of the present invention are preferably provided in an isolated form, and may be partially or substantially purified. A recombinantly produced version of any one of the GMG-7A, GMG-7B, GMG-8, GMG-9, GMG-10, or GMG-11 polypeptides can be substantially purified by the one-step method described by Smith et al. ((1988) Gene 67:31-40) or by the methods described herein or known in the art. Polypeptides of the invention also can be purified from natural or recombinant sources using antibodies directed against the polypeptides of the invention by methods known in the art of protein purification.

Preparations of GMG-7A, GMG-7B, GMG-8, GMG-9, GMG-10, or GMG-11 polypeptides of the invention involving a partial purification of or selection for the GMG-7A, GMG-7B, GMG-8, GMG-9, GMG-10, or GMG-11 polypeptides are also specifically contemplated. These crude preparations are envisioned to be the result of the concentration of cells expressing GMG-7A, GMG-7B, GMG-8, GMG-9, GMG-10, or GMG-11 polypeptides with perhaps a few additional purification steps, but prior to complete purification of the fragment. The cells expressing GMG-7A, GMG-7B, GMG-8, GMG-9, GMG-10, or GMG-11 polypeptides are present in a pellet, they are lysed, or the crude polypeptide is lyophilized, for example.

GMG-7A, GMG-7B, GMG-8, GMG-9, GMG-10, or GMG-11 polypeptide fragments can be any integer in length from at least 6 consecutive amino acids to one amino acid less than a full-length GMG-7A, GMG-7B, GMG-8, GMG-9, GMG-10, or GMG-11 polypeptide. Thus, for the polypeptide of SEQ ED NO: 10, a GMG-10 polypeptide fragment can be any integer of consecutive amino acids from 6 to 295, for example. The term "integer" is used herein in its mathematical sense and thus representative integers include, but are not limited to: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294 and 295.

Each GMG-7A, GMG-7B, GMG-8, GMG-9, GMG-10, or GMG-11 polypeptide fragment as described above can be further specified in terms of its N-terminal and C-terminal positions. For example, every combination of a N-terminal and C-terminal position that fragments of from 6 contiguous amino acids to one amino acid less than the full-length polypeptide of SEQ ID NO: 10 could occupy, on any given intact and contiguous full-length polypeptide sequence of SEQ ID NO: 10 are included in the present invention. Thus, a 6 consecutive amino acid fragment could occupy positions selected from the group consisting of 1-6, 2-7, 3-8, 4-9, 5-10, 6-11, 7-12, 8-13, 9-14, 10-15, 11-16, 12-17, 13-18, 14-19, 15-20, 16-21, 17-22, 18-23, 19-24, 20-25, 21-26, 22-27, 23-28, 24-29, 25-30, 26-31, 27-32, 28-33, 29-34, 30-35, 31-36, 32-37, 33-38, 34-39, 35-40, 36-41, 37-42, 38-43, 39-44, 40-45, 41-46, 42-47, 43-48, 44-49, 45-50, 46-51, 47-52, 48-53, 49-54, 50-55, 51-56, 52-57, 53-58, 54-59, 55-60, 56-61, 57-62, 58-63, 59-64, 60-65, 61-66, 62-67, 63-68, 64-69, 65-70, 66-71, 67-72, 68-73, 69-74, 70-75, 71-76, 72-77, 73-78, 74-79, 75-80, 76-81, 77-82, 78-83, 79-84, 80-85, 81-86, 82-87, 83-88, 84-89, 85-90, 86-91, 87-92, 88-93, 89-94, 90-95, 91-96, 92-97, 93-98, 94-99, 95-100, 96-101, 97-102, 98-103, 99-104, 100-105, 101-106, 102-107, 103-108, 104-109, 105-110, 106-111, 107-112, 108-113, 109-114, 110-115, 111-116, 112-117, 113-118, 114-119, 115-120, 116-121, 117-122, 118-123, 119-124, 120-125, 121-126, 122-127, 123-128, 124-129, 125-130, 126-131, 127-132, 128-133, 129-134, 130-135, 131-136, 132-137, 133-138, 134-139, 135-140, 136-141, 137-142, 138-143, 139-144, 140-145, 141-146, 142-147, 143-148, 144-149, 145-150, 146-151, 147-152, 148-153, 149-154, 150-155, 151-156, 152-157, 153-158, 154-159, 155-160, 156-161, 157-162, 158-163, 159-164, 160-165, 161-166, 162-167, 163-168, 164-169, 165-170, 166-171, 167-172, 168-173, 169-174, 170-175, 171-176, 172-177, 173-178, 174-179, 175-180, 176-181, 177-182, 178-183, 179-184, 180-185, 181-186, 182-187, 183-188, 184-189, 185-190, 186-191, 187-192, 188-193, 189-194, 190-195, 191-196, 192-197, 193-198, 194-199, 195-200, 196-201, 197-202, 198-203, 199-204, 200-205, 201-206, 202-207, 203-208, 204-209, 205-210, 206-211, 207-212, 208-213, 209-214, 210-215, 211-216, 212-217, 213-218, 214-219, 215-220, 216-221, 217-222, 218-223, 219-224, 220-225, 221-226, 222-227, 223-228, 224-229, 225-230, 226-231, 227-232, 228-233, 229-234, 230-235, 231-236, 232-237, 233-238, 234-239, 235-240, 236-241, 237-242, 238-243, 240-245, 241-246, 242-247, 243-248, 244-249, 245-250, 246-251, 247-252, 248-253, 249-254, 250-255, 251-256, 252-257, 253-258, 254-259, 255-260, 256-261, 257-262, 258-263, 259-264, 260-265, 261-266, 262-267, 263-268, 264-269, 265-270, 266-271, 267-272, 268-273, 269-274, 270-275, 271-276, 272-277, 273-278, 274-279, 275-280, 276-281, 277-282, 278-283, 279-284 280-285, 281-286, 282-287, 283-288, 284-289, 285-290, 286-291, 287-292, 288-293, 289-294, 290-295 and 291-296 of a 296 consecutive amino acid fragment. A 290 consecutive amino acid fragment could occupy positions selected from the group consisting of 1-290, 2-291, 3-292, 4-293, 5-294, 6-295 and 7-296. Similarly, the positions occupied by all the other fragments of sizes between 6 amino acids and 295 amino acids in SEQ ID NO: 10, by all the other fragments of sizes between 6 amino acids and 709 amino acids in SEQ ID NO: 2, by all the other fragments of sizes between 6 amino acids and 470 amino acids in SEQ ID NO: 4, by all the other fragments of sizes between 6 amino acids and 200 amino acids in SEQ ID NO: 6, by all the other fragments of sizes between 6 amino acids and 445 amino acids in SEQ ID NO: 8, and by all the other fragments of sizes between 6 amino acids and 204 amino acids in SEQ ID NO: 12 are included in the present invention and can also be immediately envisaged based on these two examples and therefore, are not individually listed solely for the purpose of not unnecessarily lengthening the specification. Furthermore, the positions occupied by fragments of 6 to 295 consecutive amino acids in SEQ ID NO: 10, by fragments of 6 to 709 consecutive amino acids in SEQ ID NO: 2, by fragments of 6 to 470 amino acids in SEQ ID NO: 4, by fragments of 6 to 200 amino acids in SEQ ID NO: 6, by fragments of 6 to 445 amino acids in SEQ ID NO: 8, and by fragments of 6 to 204 amino acids in SEQ ID NO: 12 are included in the present invention and can also be immediately envisaged based on these two examples and therefore are not individually listed solely for the purpose of not unnecessarily lengthening the specification. In addition, the positions occupied by fragments of 6 consecutive amino acids to 1 amino acid less than any other full-length GMG-7A, GMG-7B, GMG-8, GMG-9, GMG-10, or GMG-11 polypeptide can also be envisaged based on these two examples and therefore are not individually listed solely for the purpose of not unnecessarily lengthening the specification.

The GMG-7A, GMG-7B, GMG-8, GMG-9, GMG-10, or GMG-11 polypeptides of the present invention may alternatively be described by the formula "n to c" (inclusive); where "n" equals the N-terminal most amino acid position (as defined by the sequence listing) and "c" equals the C-terminal most amino acid position (as defined by the sequence listing) of the polypeptide; and further where "n" equals an integer between 1 and the number of amino acids of the full-length polypeptide sequence of the present invention minus 6; and where "c" equals an integer between 7 and the number of amino acids of the full-length polypeptide sequence; and where "n" is an integer smaller then "c" by at least 6. Therefore, for the sequences provided in SEQ ID NO: 10, "n" is any integer selected from the list consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289 or 290 and "c" is any integer selected from the group consisting of: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 291, 293, 294, 295 or 296. Every combination of "n" and "c" positions are included as specific embodiments of the invention. Moreover, the formula "n" to "c" may be modified as "'n1-n2" to "c1-c2'", wherein "n1-n2" and "c1-c2" represent positional ranges selected from any two integers above which represent amino acid positions of the sequence listing. Alternative formulas include "'n1-n2" to "c'" and "'n" to "c1-c2'". In a preferred embodiment, GMG-10 polypeptide fragments of the invention may be described by the n1=24, n2=155, and c=296 of SEQ ID NO: 10; GMG-8 polypeptide fragments of the invention by the formula n1=28, n2=71, and c=201 of SEQ ID NO: 6; and GMG-11 polypeptide fragments of the invention by the formula n1=33, n2=72, and c=205 of SEQ ID NO: 12.

Furthermore, the positions occupied by polypeptides of 6 to 710 consecutive amino acids on SEQ ID NO: 2, by polypeptides of 6 to 471 consecutive amino acids on SEQ ID NO: 4, by polypeptides of 6 to 201 consecutive amino acids on SEQ ID NO: 6, by polypeptides of 6 to 446 consecutive amino acids on SEQ ID NO: 8, or by polypeptides of 6 to 205 consecutive amino acids on SEQ ID NO: 12, are included in the present invention and can also be immediately envisaged based on these two examples and therefore are not individually listed solely for the purpose of not unnecessarily lengthening the specification. In addition, the positions occupied by fragments of 6 consecutive amino acids to 1 amino acid less than full-length GMG-7A, GMG-7B, GMG-8, GMG-9, or GMG-11 polypeptide can also be envisaged based on these two examples and therefore are not individually listed solely for the purpose of not unnecessarily lengthening the specification.

These specific embodiments, and other polypeptide and polynucleotide fragment embodiments described herein may be modified as being "at least", "equal to", "equal to or less than", "less than", "at least _____ but not greater than _____" or "from _____ to _____" a specified size or specified N-terminal and/or C-terminal positions. It is noted that all ranges used to describe any embodiment of the present invention are inclusive unless specifically set forth otherwise.

The present invention also provides for the exclusion of any individual fragment specified by N-terminal and C-terminal positions or of any fragment specified by size in amino acid residues as described above. In addition, any number of fragments specified by N-terminal and C-terminal positions or by size in amino acid residues as described above may be excluded as individual species. Further, any number of fragments specified by N-terminal and C-terminal positions or by size in amino acid residues as described above may make up a polypeptide fragment in any combination and may optionally include non-GMG-7A, -GMG-7B, -GMG-8, -GMG-9, -GMG-10, or -GMG-11 polypeptide sequences as well.

In preferred embodiments, said GMG-7A polypeptide fragments having activity are selected from amino acids 2-710, 1-262, 263-710, 1-263, 264-710 1-552, 553-710, 554-710, 561-710, 568-710, 575-710, 580-710, 581-710, 1-275 or 276-710 of SEQ ID NO: 2. In other preferred embodiments, said GMG-7B polypeptide fragments having activity are selected from amino acids 2-471, 1-442, 443-471, 1-443, 444-471, 1-262, 263-471, 1-263, 264-471, 1-275 or 276-471 of SEQ ID NO: 4. In other preferred embodiments, said GMG-8 polypeptide fragments having activity are selected from amino acids 28-201, 40-201, 54-201, 66-201, 70-201, or 71-201 of SEQ ID NO: 6. In other preferred embodiments, said GMG-9 polypeptide fragments having activity are selected from amino acids 25-446, 228-356, 228-360, 228-431, 228-446, 231-356, 231-360, 231-431, 231-446, 233-356, 233-360, 233-431, 233-446, 236-356, 236-360, 236-431, 236-446, 240-356, 240-360, 240-431, 240-446, 241-356, 241-360, 241-431, 241-446, 242-356, 242-360, 242-431, or 242-446 of SEQ ID NO: 8. In other preferred embodiments, GMG-10 polypeptide fragments having activity are selected from amino acids 8-296, 9-296, 24-296, 32-296, 39-296, 52-296, 65-296, 71-296, 74-296, 77-296, 78-296, 81-296, 84-296, 90-296, 92-296, 102-296, 110-296, 111-296, 120-296, 132-296, 135-296, 148-296, 154-296 or 155-296 of SEQ ID NO: 10. In other preferred embodiments, GMG-11 polypeptide fragments having activity are selected from amino acids 33-205, 53-205, 54-205, 59-205, 71-205 or 72-205 of SEQ ID NO: 12.

In more preferred embodiments, said GMG-7A polypeptide fragments having activity are selected from amino acids 2-710, 1-262, 1-263, 553-710, 554-710, 568-710, 575-710 or 1-275 of SEQ ID NO: 2. In other more preferred embodiments, said GMG-7B polypeptide fragments having activity are selected from amino acids 2-471, 1-442, 1-443, 1-262, 1-263, or 1-275 of SEQ ID NO: 4. In other more preferred embodiments, said GMG-8 polypeptide fragments having activity are selected from amino acids 28-201, 54-201 or 66-201 of SEQ ID NO: 6. In other more preferred embodiments, said GMG-9 polypeptide fragments having activity are selected from amino acids 25-446, 228-356, 228-360, 228-431, 228-446, 231-356, 231-360, 231-431, 231-446, 241-356, 241-360, 241-431 or 241-446 of SEQ ID NO: 8. In other more preferred embodiments, GMG-10 polypeptide fragments having activity are selected from amino acids 8-296, 9-296, 24-296, 52-296, 71-296, 74-296, 81-296, 84-296, 110-296, 111-296, 120-296, 132-296, 135-296, 148-296, 154-296 or 155-296 of SEQ ID NO: 10. In other more preferred embodiments, GMG-11 polypeptide fragments having activity are selected from amino acids 33-205, 53-205, 54-205 or 59-205 of SEQ ID NO: 12.

In yet other preferred embodiment, the invention features a GMG-10 polypeptide fragment comprising at least 115, but not more than 175 contiguous amino acids of the SEQ ID NO: 10, wherein no more than 24 of said at least 115 and no more than 175 contiguous amino acids are present in the collagen-like region of GMG-10. Preferably, the GMG-10 polypeptide fragment comprises at least 125, but not more than 165, or at least 140, but not more than 165 amino acids, and no more than 24 amino acids are in the collagen-like region; more preferably at least 125 but not more than 165, or at least 140 but not more than 165 amino acids, and no more than 12 amino acids are in the collagen-like region; or at least 140 and not more than 150 amino acids, and no more than 8 amino acids are present in the collagen-like region. Preferably, the GMG-7A, GMG-7B, GMG-8, GMG-9, GMG-10, or GMG-11 polypeptide fragment is mammalian, preferably human or mouse, but most preferably human.

GMG-7A, GMG-7B, GMG-8, GMG-9, GMG-10, or GMG-11 polypeptide fragments of the invention include variants, fragments, analogs and derivatives of the GMG-7A, GMG-7B, GMG-8, GMG-9, GMG-10, or GMG-11 polypeptide fragments described above, including modified GMG-7A, GMG-7B, GMG-8, GMG-9, GMG-10, or GMG-11 polypeptide fragments.

GMG-7A, GMG-7B, GMG-8, GMG-9, GMG-10, or GMG-11 polypeptides of the invention include variants, fragments, analogs and derivatives of the GMG-7A, GMG-7B, GMG-8, GMG-9, GMG-10, or GMG-11 polypeptides described above, including modified GMG-7A, GMG-7B, GMG-8, GMG-9, GMG-10, or GMG-11 polypeptides.

Variants

It will be recognized by one of ordinary skill in the art that some amino acids of the GMG-7A, GMG-7B, GMG-8, GMG-9, GMG-10, or GMG-11 polypeptide sequences of the present invention can be varied without significant effect on the structure or function of the proteins; there will be critical amino acids in the sequence that determine activity. Thus, the invention further includes variants of GMG-7A, GMG-7B, GMG-8, GMG-9, GMG-10, or GMG-11 polypeptides that have metabolic-related activity as described above. Such variants include GMG-7A, GMG-7B, GMG-8, GMG-9, GMG-10, or GMG-11 polypeptide sequences with one or more amino acid deletions, insertions, inversions, repeats, and substitutions either from natural mutations or human manipulation selected according to general rules known in the art so as to have little effect on activity. Guidance concerning how to make phenotypically silent amino acid substitutions is provided below.

There are two main approaches for studying the tolerance of an amino acid sequence to change (see, Bowie, et al. (1990) Science, 247, 1306-10). The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions and indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein.

In the case of an amino acid substitution in the amino acid sequence of a polypeptide according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged.

In particular embodiments, conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the GMG-7A, GMG-7B, GMG-8, GMG-9, GMG-10, or GMG-11 polypeptides are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl Acids Res, 13:4331 (1986); Zoller et al., Nucl Acids Res, 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the GMG-7A, GMG-7B, GMG-8, GMG-9, GMG-10, or GMG-11 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main chain conformation of the variant [Cunningham and Wells, Science, 244: 1081-1085 (1989)]. Alanine is also typically preferred because it is the most common amino acid. Further, it is frequently found in both buried and exposed positions [Creighton, The Proteins, (W.H. Freeman & Co., N.Y.); Chothia, J Mol Biol, 150:1 (1976)]. If alanine substitution does not yield adequate amounts of variant, an isoteric amino acid can be used.

Amino acids in the GMG-7A, GMG-7B, GMG-8, GMG-9, GMG-10, or GMG-11 polypeptide sequences of the invention that are essential for function can also be identified by methods known in the art, such as site-directed mutagenesis or alanine-scanning mutagenesis (see, e.g., Cunningham, et al. (1989) Science 244:1081-5). The latter procedure introduces single alanine mutations at every residue in the molecule. The resulting mutant molecules are then tested for metabolic-related activity using assays as described above. Of special interest are substitutions of charged amino acids with other charged or neutral amino acids that may produce proteins with highly desirable improved characteristics, such as less aggregation. Aggregation may not only reduce activity but also be problematic when preparing pharmaceutical or physiologically acceptable formulations, because aggregates can be immunogenic (see, e.g., Pinckard, et al., (1967) Clin Exp Immunol 2:331-340; Robbins, et al., (1987) Diabetes 36:838-41; and Cleland, et al., (1993) Crit Rev Ther Drug Carrier Syst 10:307-77).

Thus, the fragment, derivative, analog, or homolog of the GMG-7A, GMG-7B, GMG-8, GMG-9, GMG-10, or GMG-11 polypeptides of the present invention may be, for example: (i) one in which one or more of the amino acid residues are substituted with a conserved or non-conserved amino acid residue (preferably a conserved amino acid residue) and such substituted amino acid residue may or may not be one encoded by the genetic code (i.e. may be a non-naturally occurring amino acid); or (ii) one in which one or more of the amino acid residues includes a substituent group; or (iii) one in which the GMG-7A, GMG-7B, GMG-8, GMG-9, GMG-10, or GMG-11 polypeptides are fused with another compound, such as a compound to increase the half-life of the fragment (for example, polyethylene glycol); or (iv) one in which the additional amino acids are fused to the above form of the fragment, such as an IgG Fc fusion region peptide or leader or secretory sequence or a sequence which is employed for purification of the above form of the fragment or a pro-protein sequence. Such fragments, derivatives and analogs are deemed to be within the scope of those skilled in the art from the teachings herein.

A further embodiment of the invention relates to a polypeptide which comprises the amino acid sequence of GMG-7A, GMG-7B, GMG-8, GMG-9, GMG-10, or GMG-11 polypeptides having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a GMG-7A, GMG-7B, GMG-8, GMG-9, GMG-10, or GMG-11 fragment, having at least one, but not more than 10, 9, 8, 7, 6, 5, 4, 3, 2 or 1 conservative amino acid substitutions.

In addition, amino acids have chirality within the body of either L or D. In some embodiments it is preferable to alter the chirality of the amino acids in the GMG-7A, GMG-7B, GMG-8, GMG-9, GMG-10, or GMG-11 polypeptide fragments of the invention in order to extend half-life within the body. Thus, in some embodiments, one or more of the amino acids are preferably in the L configuration. In other embodiments, one or more of the amino acids are preferably in the D configuration.

Percent Identity

The polypeptides of the present invention also include polypeptides having an amino acid sequence at least 50% identical, at least 60% identical, or 70%, 80%, 85%, 90%, 91%, 92%, 93%, 94%, 95%, 96%, 97%, 98% or 99% identical to a GMG-7A, GMG-7B, GMG-8, GMG-9, GMG-10, or GMG-11 polypeptide as described above. By a polypeptide having an amino acid sequence at least, for example, 95% "identical" to a GMG-7A, GMG-7B, GMG-8, GMG-9, GMG-10, or GMG-11 polypeptide amino acid sequence is meant that the amino acid sequence is identical to the GMG-7A, GMG-7B, GMG-8, GMG-9, GMG-10, or GMG-11 polypeptide sequence except that it may include up to five amino acid alterations per each 100 amino acids of the GMG-7A, GMG-7B, GMG-8, GMG-9, GMG-10, or GMG-11 polypeptide amino acid sequence. The reference sequence is the GMG-7A, GMG-7B, GMG-8, GMG-9, GMG-10, or GMG-11 polypeptide with a sequence corresponding to the sequences provided in SEQ ED NOs: 2, 4, 6, 8, 10, or 12. Thus, to obtain a polypeptide having an amino acid sequence at least 95% identical to a GMG-7A, GMG-713, GMG-8, GMG-9, GMG-10, or GMG-11 polypeptide amino acid sequence, up to 5% (5 of 100) of the amino acid residues in the sequence may be inserted, deleted, or substituted with another amino acid compared with the GMG-7A, GMG-7B, GMG-8, GMG-9, GMG-10, or GMG-11 polypeptide sequence. These alterations may occur at the amino or carboxy termini or anywhere between those terminal positions, interspersed either individually among residues in the sequence or in one or more contiguous groups within the sequence.

As a practical matter, whether any particular polypeptide is a percentage identical to a GMG-7A, GMG-7B, GMG-8, GMG-9, GMG-10, or GMG-11 polypeptide can be determined conventionally using known computer programs. Such algorithms and programs include, but are by no means limited to, TBLASTN, BLASTP, FASTA, TFASTA, and CLUSTALW (Pearson and Lipman, (1988) Proc Natl Acad Sci USA 85:2444-8; Altschul et al., (1990) J Mol Biol 215:403-410; Thompson et al., (1994) Nucleic Acids Res 22(2):4673-4680; Higgins et al, (1996) Meth Enzymol 266: 383-402; Altschul et al, (1997) Nucleic Acids Res 25:3389-3402; Altschul et al., (1993) Nature Genetics 3:266-272). In a particularly preferred embodiment, protein and nucleic acid sequence homologies are evaluated using the Basic Local Alignment Search Tool ("BLAST"), which is well known in the art (See, e.g., Karlin and Altschul (1990) Proc Natl Acad Sci USA 87:2264-8; Altschul et al., 1990, 1993, 1997, all supra). In particular, five specific BLAST programs are used to perform the following tasks:

(1) BLASTP and BLAST3 compare an ammo acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (see, Gonnet et al., (1992) Science 256:1443-5; Henikoff and Henikoff (1993) Proteins 17:49-61). Less preferably, the PAM or PAM250 matrices may also be used (See, e.g., Schwartz and Dayhoff, eds, (1978) Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (See, e.g., Karlin and Altschul, (1990) Proc Natl Acad Sci USA 87:2264-8). The BLAST programs may be used with the default parameters or with modified parameters provided by the user. Preferably, the parameters are default parameters.

A preferred method for determining the best overall match between a query sequence (a sequence of the present invention) and a subject sequence, also referred to as a global sequence alignment, can be determined using the FASTDB computer program based on the algorithm of Brutlag et al. (1990) Comp App Biosci 6:237-245. In a sequence alignment the query and subject sequences are both amino acid sequences. The result of said global sequence alignment is in percent identity. Preferred parameters used in a FASTDB amino acid alignment are: Matrx=PAM 0, k-tuple=2, Mismatch Penalty=1, Joining Penalty=20, Randomization Group=25 Length=0, Cutoff Score=1, Window Size=sequence length, Gap Penalty=5, Gap Size Penalty=0.05, Window Size=247 or the length of the subject amino acid sequence, whichever is shorter.

If the subject sequence is shorter than the query sequence due to N- or C-terminal deletions, not because of internal deletions, the results, in percent identity, must be manually corrected because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, that are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%.

In another example, a 90-residue subject sequence is compared with a 100-residue query sequence. This time the deletions are internal so there are no residues at the N- or C-termini of the subject sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are made for the purposes of the present invention.

Production

Note, throughout the disclosure, wherever GMG-7A, GMG-7B, GMG-8, GMG-9, GMG-10, or GMG-11 polypeptides are discussed, GMG-7A, GMG-7B, GMG-8, GMG-9, GMG-10, or GMG-11 fragments, variants and derivatives are specifically intended to be included as a preferred subset of GMG-7A, GMG-7B, GMG-8, GMG-9, GMG-10, or GMG-11 polypeptides.

GMG-7A, GMG-7B, GMG-8, GMG-9, GMG-10, or GMG-11 polypeptides are preferably isolated from human or mammalian tissue samples or expressed from human or mammalian genes in human or mammalian cells. The GMG-7A, GMG-7B, GMG-8, GMG-9, GMG-10, or GMG-11 polypeptides of the invention can be made using routine expression methods known in the art. The polynucleotide encoding the desired polypeptide is ligated into an expression vector suitable for any convenient host. Both eukaryotic and prokaryotic host systems are used in forming recombinant polypeptides. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In an alternative embodiment, the polypeptides of the invention are isolated from milk. The polypeptides can be purified as full length GMG-7A, GMG-7B, GMG-8, GMG-9, GMG-10, or GMG-11 polypeptides, which can then be cleaved, if appropriate, in vitro to generate a GMG-7A, GMG-7B, GMG-8, GMG-9, GMG-10, or GMG-11 fragment, or, alternatively, GMG-7A, GMG-7B, GMG-8, GMG-9, GMG-10, or GMG-11 fragments themselves can be purified from the milk. Any of a large number of methods can be used to purify the present polypeptides from milk, including those taught in Protein Purification Applications, A Practical Approach (New Edition), Edited by Simon Roe, ABA Technology Products and Systems, Biosciences, Harwell; Clark (1998) J Mammary Gland Biol Neoplasia 3:337-50; Wilkins and Velander (1992) 49:333-8; U.S. Pat. Nos. 6,140,552; 6,025,540; Hennighausen, Protein Expression and Purification, vol. 1, pp. 3-8 (1990); Harris et al. (1997) Bioseparation 7:31-7; Degener et al. (1998) J Chromatog 799:125-37; Wilkins (1993) J Cell Biochem. Suppl. 0 (17 part A):39; the entire disclosures of each of which are herein incorporated by reference. In a typical embodiment, milk is centrifuged, e.g. at a relatively low speed, to separate the lipid fraction, and the aqueous supernatant is then centrifuged at a higher speed to separate the casein in the milk from the remaining, "whey" fraction. Often, biomedical proteins are found in this whey fraction, and can be isolated from this fraction using standard chromatographic or other procedures commonly used for protein purification, e.g. as described elsewhere in the present application. In one preferred embodiment, GMG-7A, GMG-7B, GMG-8, GMG-9, GMG-10, or GMG-11 polypeptides are purified using antibodies specific to GMG-7A, GMG-7B, GMG-8, GMG-9, GMG-10, or GMG-11 polypeptides, e.g. using affinity chromatography. In addition, methods can be used to isolate particular GMG-7A, GMG-7B, GMG-8, GMG-9, GMG-10, or GMG-11 fragments, e.g. electrophoretic or other methods for isolating proteins of a particular size. The GMG-7A, GMG-7B, GMG-8, GMG-9, GMG-10, or GMG-11 polypeptides isolating using these methods can be naturally occurring, as GMG-7A, GMG-7B, GMG-8, GMG-9, GMG-10, or GMG-11 polypeptides have been discovered to be naturally present in the milk of mammals, or can be the result of the recombinant production of the protein in the mammary glands of a non-human mammal, as described infra. In one such embodiment, the GMG-7A, GMG-7B, GMG-8, GMG-9, GMG-10, or GMG-11 is produced as a fusion protein with a heterologous, antigenic polypeptide sequence, which antigenic sequence can be used to purify the protein, e.g., using standard immuno-affinity methodology.

In addition, shorter protein fragments may be produced by chemical synthesis. Alternatively, the proteins of the invention are extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any GMG-7A, GMG-7B, GMG-8, GMG-9, GMG-10, or GMG-DNA, including those in SEQ ED NO: 1, 3, 5, 7, 9 or 11, can be used to express GMG-7A, GMG-7B, GMG-8, GMG-9, GMG-10, or GMG-11 polypeptides. The nucleic acid encoding the GMG-7A, GMG-7B, GMG-8, GMG-9, GMG-10, or GMG-11 to be expressed is operably linked to a promoter in an expression vector using conventional cloning technology. The GMG-7A, GMG-7B, GMG-8, GMG-9, GMG-10, or GMG-11 cDNA insert in the expression vector may comprise the coding sequence for: the full-length GMG-7A, GMG-7B, GMG-8, GMG-9, GMG-10, or GMG-11 polypeptide (to be later modified); from 6 amino acids to any integer less than the full-length GMG-7A, GMG-7B, GMG-8, GMG-9, GMG-10, or GMG-11 polypeptide; a GMG-7A, GMG-7B, GMG-8, GMG-9, GMG-10, or GMG-11 fragment; or variants and % similar polypeptides.

The expression vector is any of the mammalian, yeast, insect or bacterial expression systems known in the art, some of which are described herein. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism into which the expression vector is introduced, as explained by Hatfield, et al., U.S. Pat. No. 5,082,767, the disclosures of which are incorporated by reference herein in their entirety.

If the nucleic acid encoding any one of the GMG-7A, GMG-7B, GMG-8, GMG-9, GMG 10, or GMG-11 polypeptides lacks a methionine to serve as the initiation site, an initiating methionine can be introduced next to the first codon of the nucleic acid using conventional techniques. Similarly, if the insert from the GMG-7A, GMG-7B, GMG-8, GMG-9, GMG-10, or GMG-11 polypeptide cDNA lacks a poly A signal, this sequence can be added to the construct by, for example, splicing out the Poly A signal from pSG5 (Stratagene) using BglI and SaiI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allows efficient stable transfection. The vector includes the Herpes Simplex Thyridine Kinase promoter and the selectable neomycin gene.

The nucleic acid encoding GMG-7A, GMG-7B, GMG-8, GMG-9, GMG-10, or GMG-11 can be obtained by PCR from a vector containing the GMG-7A, GMG-7B, GMG-8, GMG-9, GMG-10, or GMG-11 nucleotide sequence using oligonucleotide primers complementary to the desired GMG-7A, GMG-7B, GMG-8, GMG-9, GMG-10, or GMG-11 cDNA and containing restriction endonuclease sequences for Pst I incorporated into the 5' primer and BglII at the 5' end of the corresponding cDNA 3' primer, taking care to ensure that the sequence encoding the GMG-7A, GMG-7B, GMG-8, GMG-9, GMG-10, or GMG-11 is positioned properly with respect to the poly A signal. The purified polynucleotide obtained from the resulting PCR reaction is digested with PstI, blunt ended with an exonuclease, digested with BglII, purified and ligated to pXT1, now containing a poly A signal and digested with BglII.

Transfection of a GMG-7A, GMG-7B, GMG-8, GMG-9, GMG-10, or GMG-11 expressing vector into mouse NIH 3T3 cells is one embodiment of introducing polynucleotides into host cells. Introduction of a polynucleotide encoding a polypeptide into a host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al. ((1986) Methods in Molecular Biology, Elsevier Science Publishing Co., Inc., Amsterdam). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

Depending upon the host employed in a recombinant production procedure, the polypeptides of the present invention may be glycosylated or may be non-glycosylated.

Preferably the polypeptides of the invention are non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., (1989) Proc Natl Acad Sci USA 86:8932-5; Koller et al., (1989) Proc Natl Acad Sci USA 86:8927-31; and Zijistra et al. (1989) Nature 342:435-8; the disclosures of each of which are incorporated by reference in their entireties).

Modifications

In addition, polypeptides of the invention can be chemically synthesized using techniques known in the art (See, e.g., Creighton, 1983 Proteins. New York, N.Y.: W.H. Freeman and Company; and Hunkapiller et al., (1984) Nature 310:105-11). For example, a relative short fragment of the invention can be synthesized by use of a peptide synthesizer. Furthermore, if desired, nonclassical amino acids or chemical amino acid analogs can be introduced as a substitution or addition into the fragment sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoroamino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the polypeptide.

Also provided by the invention are chemically modified derivatives of the polypeptides of the invention that may provide additional advantages such as increased solubility, stability and circulating time of the polypeptide, or decreased immunogenicity. See U.S. Pat. No. 4,179,337. The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the polypeptide with consideration of effects on functional or antigenic domains of the polypeptide. There are a number of attachment methods available to those skilled in the art, e.g., EP 0 401 384, herein incorporated by reference (coupling PEG to G-CSF), see also Malik et al. (1992) Exp Hematol (8):1028-35, reporting pegylation of GMG-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Multimers

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, pharmaceutical or physiologically acceptable compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the GMG-7A, GMG-7B, GMG-8, GMG-9, GMG-10, or GMG-11 polypeptides of the invention (including polypeptide fragments, variants, splice variants, and fusion proteins corresponding to these polypeptide fragments as described herein). These homomers may contain polypeptide fragments having identical or different amino acid sequences. In a specific embodiment, a homomer of the invention is a multimer containing only polypeptide fragments having an identical amino acid sequence. In another specific embodiment, a homomer of the invention is a multimer containing polypeptide fragments having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., corresponding to different proteins or polypeptides thereof) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-inking between cysteine residues located within the polypeptide sequences, which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins, and have since been found in a variety of different proteins (Landschulz et al., (1988) Genes Dev 2:786-800). Among the known leucine zippers are naturally occurring peptides and derivatives thereof that dimerize or trimerize. Examples of leucine zipper domains suitable for producing soluble multimeric proteins of the invention are those described in PCr application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. FEBS Letters (1994) 344:191-5 and in U.S. patent application Ser. No. 08/446,922, hereby incorporated by reference. Other peptides derived from naturally occurring trimeric proteins may be employed in preparing trimeric polypeptides of the invention. In another example, proteins of the invention are associated by interactions between Flag® & polypeptide sequence contained in fusion proteins of the invention containing Flag® polypeptide sequence. In a further embodiment, proteins of the invention are associated by interactions between heterologous polypeptide sequence contained in Flag® fusion proteins of the invention and anti Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, at least 30 techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (See, e.g., U.S. Pat. No. 5,478,925, which is herein incorporated by reference in its entirety).

II. GMG-7A, GMG-7B, GMG-8, GMG-9, GMG-10, or GMG-11 Polynucleotides of the Invention Preferred polynucleotides are those that encode GMG-7A, GMG-7B, GMG-8, GMG-9, GMG-10, or GMG-11 polypeptides of the invention. The recombinant polynucleotides encoding GMG-7A, GMG-7B, GMG-8, GMG-9, GMG-10, or GMG-11 polypeptides can be used in a variety of ways, including, but not limited to, expressing the polypeptides in recombinant cells for use in screening assays for antagonists and agonists of its activity as well as to facilitate its purification for use in a variety of ways including, but not limited to screening assays for agonists and antagonists of its activity, diagnostic screens, and raising antibodies, as well as treatment and/or prevention of metabolic-related diseases and disorders and/or to reduce body mass.

The invention relates to the polynucleotides encoding GMG-7A, GMG-7B, GMG-8, GMG-9, GMG-10, or GMG-11 polypeptides and variant polypeptides thereof as described herein. These polynucleotides may be purified, isolated, and/or recombinant. In all cases, the desired GMG-7A, GMG-7B, GMG-8, GMG-9, GMG-10, or GMG-11 polynucleotides of the invention are those that encode GMG-7A, GMG-7B, GMG-8, GMG-9, GMG-10, or GMG-11 polypeptides of the invention having metabolic-related activity as described and discussed herein.

Fragments

A polynucleotide fragment is a polynucleotide having a sequence that entirely is the same as part, but not all, of the full-length GMG-7A, GMG-7B, GMG-8, GMG-9, GMG-10, or GMG-11 polypeptide or a specified GMG-7A, GMG-7B, GMG-8, GMG-9, GMG-10, or GMG-11 polypeptide nucleotide sequence. Such fragments may be "free-standing", i.e. not part of or fused to other polynucleotides, or they may be comprised within another non-GMG-7A, -GMG-7B, -GMG-8, -GMG-9, -GMG-10, or -GMG-11 (heterologous) polynucleotide of which they form a part or region. However, several GMG-7A, GMG-7B, GMG-8, GMG-9, GMG-10, or GMG-11 polynucleotide fragments may be comprised within a single polynucleotide.

The GMG-7A, GMG-7B, GMG-8, GMG-9, GMG-10, or GMG-11 polynucleotides of the invention comprise from 18 consecutive bases to the full-length polynucleotide sequences encoding the intact GMG-7A, GMG-7B, GMG-8, GMG-9, GMG-10, or GMG-11 polypeptides, for example the full-length GMG-7A, GMG-7B, GMG-8, GMG-9, GMG-10, or GMG-11 polypeptide polynucleotide sequences in SEQ ID NO: 1, 3, 5, 7, 9, or 11. In one aspect of this embodiment, the polynucleotide comprises at least 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 611, 615, 620, 625, 630, 635, 640, 645, 650, 655, 660, 665, 670, 675, 680, 685, 690, 695, 700, 705, 710, 715, 720, 725, 740, 770, 800, 850, 900, 950, 1000, 1050, 1100, 1150, 1200, 1242, 1250, 1300, 1338, 1350, 1400, 1450, 1500, 1550, 1600, 1630, 1650, 1700, 1750, 1800, 1850, 1900, 1950, 2000, 2050, 2100, 2150, 2200, 2250 or 2257 consecutive nucleotides of a polynucleotide of the present invention.

In addition to the above preferred nucleic acid sizes, further preferred nucleic acids comprise at least 18 nucleotides, wherein "at least 18" is defined as any integer between 18 and the integer representing the 3' most nucleotide position of the intact GMG-7A, GMG-7B, GMG-8, GMG-9, GMG-10, or GMG-11 polypeptides cDNA as set forth in SEQ ID NOs: 1, 3, 5, 7, 9, or 11 or elsewhere herein.

Further included as preferred polynucleotides of the present invention are nucleic acid fragments at least 18 nucleotides in length, as described above, that are further specified in terms of their 5' and 3' position. The 5' and 3' positions are represented by the position numbers set forth in the sequence listing below. For allelic and degenerate and other variants, position 1 is defined as the 5' most nucleotide of the ORF, i.e., the nucleotide "A" of the start codon (ATG) with the remaining nucleotides numbered consecutively.

Therefore, every combination of a 5' and 3' nucleotide position that a polynucleotide fragment, at least 18 contiguous nucleotides in length, could occupy on an intact GMG-7A, GMG-7B, GMG-8, GMG-9, GMG-10, or GMG-11 polynucleotide encoding a polypeptide of the present invention is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the polynucleotide sequence of the present invention minus 18, and where "y" equals an integer between 19 and the number of nucleotides of the polynucleotide sequence of the present invention minus 18 nucleotides; and where "x" is an integer less than "y" by at least 18.

The present invention also provides for the exclusion of any species of polynucleotide fragments of the present invention specified by 5' and 3' positions or polynucleotides specified by size in nucleotides as described above. Any number of fragments specified by 5' and 3' positions or by size in nucleotides, as described above, may be excluded.

The GMG-7A, GMG-7B, GMG-8, GMG-9, GMG-10, or GMG-11 polynucleotide fragments of the invention comprise from 18 consecutive bases to the full-length polynucleotide sequence encoding the GMG-7A, GMG-7B, GMG-8, GMG-9, GMG-10, or GMG-11 polypeptide fragments described in Section II of the Preferred Embodiments of the Invention. In one aspect of this embodiment, the polynucleotide comprises at least 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 611, 615, 620, 625, 630, 635, 640, 645, 650, 655, 660, 665, 670, 675, 680, 685, 690, 695, 700, 705, 710, 715, 720, 725, 740, 770, 800, 850, 900, 950, 1000, 1050, 1100, 1150, 1200, 1242, 1250, 1300, 1338, 1350, 1400, 1450, 1500, 1550, 1600, 1630, 1650, 1700, 1750, 1800, 1850, 1900, 1950, 2000, 2050, 2100, 2150, 2200, 2250 or 2257 consecutive nucleotides of a polynucleotide of the present invention.

In addition to the above preferred nucleic acid sizes, further preferred nucleic acids comprise at least 18 nucleotides, wherein "at least 18" is defined as any integer between 18 and the integer corresponding to the 3' most nucleotide position of a GMG-7A, GMG-7B, GMG-8, GMG-9, GMG-10, or GMG-11 fragment cDNA herein.

Further included as preferred polynucleotides of the present invention are nucleic acid fragments at least 18 nucleotides in length, as described above, that are further specified in terms of their 5' and 3' position. The 5' and 3' positions are represented by the position numbers set forth in the sequence listing below. For allelic and degenerate and other variants, position 1 is defined as the 5' most nucleotide of the open reading frame (ORF), i.e., the nucleotide "A" of the start codon (ATG) with the remaining nucleotides numbered consecutively. Therefore, every combination of a 5' and 3' nucleotide position that a polynucleotide fragment invention, at least 18 contiguous nucleotides in length, could occupy on a GMG-7A, GMG-7B, GMG-8, GMG-9, GMG-10, or GMG-11 fragment polynucleotide of the present invention is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the GMG-7A, GMG-7B, GMG-8, GMG-9, GMG-10, or GMG-11 polynucleotide sequences of the present invention minus 18, and where "y" equals an integer between 9 and the number of nucleotides of the GMG-7A, GMG-7B, GMG-8, GMG-9, GMG-10, or GMG-11 polynucleotide sequences of the present invention; and where "x" is an integer smaller than "y" by at least 18. Every combination of "x" and 'y' positions are included as specific embodiments of the invention. Moreover, the formula "x" to "y" may be modified as "'x1-x2" to "y1-y2'", wherein "x1-x2" and "y1-y2" represent positional ranges selected from any two nucleotide positions of the sequence listing. Alternative formulas include "'x1-x2" to "y'" and "'x" to "y1-y2'".

These specific embodiments, and other polynucleotide fragment embodiments described herein may be modified as being "at least", "equal to", "equal to or less than", "less than", "at least _____ but not greater than _____" or "from _____ to _____", a specified size or specified 5' and/or 3' positions.

The present invention also provides for the exclusion of any species of polynucleotide fragments of the present invention specified by 5' and 3' positions or polynucleotides specified by size in nucleotides as described above. Any number of fragments specified by 5' and 3' positions or by size in nucleotides, as described above, may be excluded.

Variants

In other preferred embodiments, variants of GMG-7A, GMG-7B, GMG-8, GMG-9, GMG-10, or GMG-11 polynucleotides encoding GMG-7A, GMG-7B, GMG-8, GMG-9, GMG-10, or GMG-11 polypeptides are envisioned. Variants of polynucleotides, as the term is used herein, are polynucleotides whose sequence differs from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Polynucleotide variants that comprise a sequence substantially different from those described above but that, due to the degeneracy of the genetic code, still encode GMG-7A, GMG-7B, GMG-8, GMG-9, GMG-10, or GMG-11 polypeptides of the present invention are also specifically envisioned. It would also be routine for one skilled in the art to generate the degenerate variants described above, for instance, to optimize codon expression for a particular host (e.g., change codons in the human mRNA to those preferred by other mammalian or bacterial host cells).

As stated above, variant polynucleotides may occur naturally, such as a natural allelic variant, or by recombinant methods. By an "allelic variant" is intended one of several alternate forms of a gene occupying a given locus on a chromosome of an organism (See, e.g., B. Lewin, (1990) Genes IV, Oxford University Press, New York). Non-naturally occurring variants may be produced using art-known mutagenesis techniques. Such nucleic acid variants include those produced by nucleotide substitutions, deletions, or additions. The substitutions, deletions, or additions may involve one or more nucleotides. Alterations in the coding regions may produce conservative or non-conservative amino acid substitutions, deletions or additions. Especially preferred among these are silent substitutions, additions and deletions, which do not alter the properties and activities of GMG-7A, GMG-7B, GMG-8, GMG-9, GMG-10, or GMG-11 polypeptides of the invention. Also preferred in this regard are conservative substitutions.

Nucleotide changes present in a variant polynucleotide are preferably silent, which means that they do not alter the amino acids encoded by the polynucleotide. However, nucleotide changes may also result in amino acid substitutions, additions, deletions, fusions and truncations in the polypeptide encoded by the reference sequence.

In cases where the nucleotide substitutions result in one or more amino acid changes, preferred GMG-7A, GMG-7B, GMG-8, GMG-9, GMG-10, or GMG-11 polypeptides include those that retain one or more metabolic-related activity as described in Section I of the Preferred Embodiments of the Invention.

By "retain the same activities" is meant that the activity measured using the polypeptide encoded by the variant GMG-7A, GMG-7B, GMG-8, GMG-9, GMG-10, or GMG-11 polynucleotide in assays is at least 75%, 80%, 85%, 90%, 95%, 96%, 97%, 98%, 99%, or 100%, and not more than 101%, 102%, 103%, 104%, 105%, 110%, 115%, 120% or 125% of the activity measured using a GMG-7A, GMG-7B, GMG-8, GMG-9, GMG-10, or GMG-11 polypeptide described in the Examples Section herein.

By the activity being "increased" is meant that the activity measured using the polypeptide encoded by the variant GMG-7A, GMG-7B, GMG-8, GMG-9, GMG-10, or GMG-11 polynucleotide in assays is at least 125%, 130%, 135%, 140%, 145%, 150%, 155%, 160%, 170%, 180%, 190%, 200%, 225%, 250%, 275%, 300%, 325%, 350%, 375%, 400%, 450%, or 500% of the activity measured using a GMG-7A, GMG-7B, GMG-8, GMG-9, GMG-10, or GMG-11 polypeptide described in the Examples Section herein.

By the activity being "decreased" is meant that the activity measured using the polypeptide encoded by the variant GMG-7A, GMG-7B, GMG-8, GMG-9, GMG-10, or GMG-11 polynucleotide in assays is decreased by at least 25%, 30%, 35%, 40%, 45%, 50%, 75%, 80%, 90% or 95% of the activity measured using a GMG-7A, GMG-7B, GMG-8, GMG-9, GMG-10, or GMG-11 polypeptide described in the Examples Section herein Percent Identity The present invention is further directed to nucleic acid molecules having sequences at least 50%, 60%, 70%, 80%, 90%, 95%, 96%, 97%, 98% or 99% identical to the polynucleotide sequences of SEQ ID NOs: 1, 3, 5, 7, 9, or 11 or fragments thereof that encode a polypeptide having metabolic-related activity as described in Section I of the Preferred Embodiments of the Invention. Of course, due to the degeneracy of the genetic code, one of ordinary skill in the art will immediately recognize that a large number of the nucleic acid molecules at least 50%, 60%, 70%, 80%, 90%, 95%, 96%, 97%, 98%, or 99% identical to the nucleic acid sequences shown in SEQ ID NOs: 1, 3, 5, 7, 9, or 11 or fragments thereof will encode a polypeptide having biological activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having biological activity. This is because the skilled artisan is fully aware of amino acid substitutions that are either less likely or not likely to significantly affect protein function (e.g., replacing one aliphatic amino acid with a second aliphatic amino acid), as further described previously in Section I of the Preferred Embodiments of the Invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the GMG-7A, GMG-7B, GMG-8, GMG-9, GMG-10, or GMG-11 polypeptide. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be an entire sequence or any fragment specified as described herein.

The methods of determining and defining whether any particular nucleic acid molecule or polypeptide is at least 50%, 60%, 70%, 80%, 90%, 95%, 96%, 97%, 98% or 99% identical to a nucleotide sequence of the present invention can be done by using known computer programs. A preferred method for determining the best overall match between a query sequence (a sequence of the present invention) and a subject sequence, also referred to as a global sequence alignment, can be determined using the FASTDB computer program based on the algorithm of Brutlag et al., ((1990) Comput Appl Biosci. July; 6(3):23745). In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrx=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score.

This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score.

For example, a 90-nucleotide subject sequence is aligned to a 100-nucleotide query sequence to determine percent identity. The deletions occur at the 5' end of the subject sequence and therefore, the FASTDB alignment does not show a matched/alignment of the first 10 nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%.

In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are made for the purposes of the present invention.

Fusions

Further included in the present invention are polynucleotides encoding the polypeptides of the present invention that are fused in frame to the coding sequences for additional heterologous amino acid sequences. Also included in the present invention are nucleic acids encoding polypeptides of the present invention together with additional, non-coding sequences, including for example, but not limited to non-coding 5' and 3' sequences, vector sequence, sequences used for purification, probing, or priming. For example, heterologous sequences include transcribed, non-translated sequences that may play a role in transcription, and mRNA processing, for example, ribosome binding and stability of mRNA. The heterologous sequences may alternatively comprise additional coding sequences that provide additional functionalities. Thus, a nucleotide sequence encoding a polypeptide may be fused to a tag sequence, such as a sequence encoding a peptide that facilitates purification of the fused polypeptide. In certain preferred embodiments of this aspect of the invention, the tag amino acid sequence is a hexa-histidine peptide, such as the tag provided in a pQE vector (QIAGEN, Chatsworth, Calif.), among others, many of which are commercially available. For instance, hexa-histidine provides for convenient purification of the fusion protein (See, Gentz et al., (1989) Proc Natl Acad Sci USA 86:821-4). The "HA" tag is another peptide useful for purification which corresponds to an epitope derived from the influenza hemagglutinin protein (See, Wilson et al., (1984) Cell 37:767-78). As discussed above, other such fusion proteins include GMG-7A, GMG-7B, GMG-8, GMG-9, GMG-O, or GMG-11 cDNA fused to Fc at the N- or C-terminus.

III. Recombinant Vectors of the Invention

The term "vector" is used herein to designate either a circular or a linear DNA or RNA molecule, that is either double-stranded or single-stranded, and that comprises at least one polynucleotide of interest that is sought to be transferred in a cell host or in a unicellular or multicellular host organism.

The present invention relates to recombinant vectors comprising any one of the polynucleotides described herein.

The present invention encompasses a family of recombinant vectors that comprise polynucleotides encoding GMG-7A, GMG-7B, GMG-8, GMG-9, GMG-10, or GMG-11 polypeptides of the invention.

In a first preferred embodiment, a recombinant vector of the invention is used to amplify the inserted polynucleotide in a suitable cell host, this polynucleotide being amplified every time that the recombinant vector replicates. The inserted polynucleotide can be one that encodes GMG-7A, GMG-7B, GMG-8, GMG-9, GMG-10, or GMG-11 polypeptides of the invention.

A second preferred embodiment of the recombinant vectors according to the invention consists of expression vectors comprising polynucleotides encoding GMG-7A, GMG-7B, GMG-8, GMG-9, GMG-O, or GMG-11 polypeptides of the invention. Within certain embodiments, expression vectors are employed to express a GMG-7A, GMG-7B, GMG-8, GMG-9, GMG-10, or GMG-11 polypeptide of the invention, preferably a modified GMG-7A, GMG-7B, GMG-8, GMG-9, GMG-10, or GMG-11 described in the present invention, which can be then purified and, for example, be used as a treatment for metabolic-related diseases, or simply to reduce body mass of individuals.

Expression requires that appropriate signals are provided in the vectors, said signals including various regulatory elements, such as enhancers/promoters from both viral and mammalian sources, that drive expression of the genes of interest in host cells. Dominant drug selection markers for establishing permanent, stable, cell clones expressing the products are generally included in the expression vectors of the invention, as they are elements that link expression of the drug selection markers to expression of the polypeptide.

More particularly, the present invention relates to expression vectors which include nucleic acids encoding a GMG-7A, GMG-7B, GMG-8, GMG-9, GMG-10, or GMG-11 polypeptide of the invention, or a modified GMG-7A, GMG-7B, GMG-8, GMG-9, GMG-10, or GMG-11 as described herein, or variants or fragments thereof, under the control of a regulatory sequence selected among GMG-7A, GMG-7B, GMG-8, GMG-9, GMG-10, or GMG-11 polypeptides, or alternatively under the control of an exogenous regulatory sequence.

Consequently, preferred expression vectors of the invention are selected from the group consisting of: (a) a regulatory sequence driving the expression of a coding polynucleotide operably linked thereto; and (b) a GMG-7A, GMG-7B, GMG-8, GMG-9, GMG-10, or GMG-11 coding sequence of the invention, operably linked to regulatory sequences allowing its expression in a suitable cell host and/or host organism.

Some of the elements that can be found in the vectors of the present invention are described in further detail in the following sections.

1) General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid, or even a linear DNA molecule which may consist of a chromosomal, nonchromosomal, semi-synthetic or synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription;

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation sites, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

2) Regulatory Elements

Promoters

The suitable promoter regions used in the expression vectors of the present invention are chosen taking into account the cell host in which the heterologous gene is expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors. Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., (1983) Mol Cell Biol 3:2156-65; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. In addition, promoters specific for a particular cell type may be chosen, such as those facilitating expression in adipose tissue, muscle tissue, or liver. Selection of a convenient vector and promoter is well within the level of ordinary skill in the art.

The choice of a promoter is well within the ability of a person skilled in the field of genetic engineering. For example, one may refer to Sambrook et al. (1989) Molecular Cloning: A Laboratory Manual, Cold Spring Harbor Laboratory Press, NY, Vol. 1, 2, 3 (1989), or also to the procedures described by Fuller et al. (1996) Immunology in Current Protocols in Molecular Biology.

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

Vectors containing the appropriate DNA sequence as described above can be utilized to transform an appropriate host to allow the expression of the desired polypeptide or polynucleotide.

3) Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4) Preferred Vectors

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and pGEM1 (Promega Biotec, Madison, Wis., USA).

Large numbers of other suitable vectors are known to those of skill in the art, and are commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Baculovirus Vectors

A suitable vector for the expression of polypeptides of the invention is a baculovirus vector that can be propagated in insect cells and in insect cell lines. A specific suitable host vector system is the pVL1392/1393 baculovirus transfer vector (Pharmingen) that is used to transfect the SF9 cell line (ATCC N°CRL 1711) which is derived from *Spodoptera frugiperda*.

Other suitable vectors for the expression of a GMG-7A, GMG-7B, GMG-8, GMG-9, GMG-10, or GMG-11 polypeptide in a baculovirus expression system include those described by Chai et al. (1993; Biotechnol Appl Biochem 18 (Pt 3):259-73); Vlasak et al. (1983; Eur J Biochem 135:123-6); and Lenhard et al. (1996; Gene 169: 187-90).

Plasmid Vectors

A suitable vector for the expression of polypeptides of the invention is a plasmid vector that contains an SV40-derived origin of replication and that can be used for transient transfection of COS cells (ATCC N°CRL1650; N°CRL1651). Plasmid vectors suitable for transient transfection of COS cells include but are not limited to CDM8 (Invitrogen).

Viral Vectors

In one specific embodiment, the vector is derived from an adenovirus. Preferred adenovirus vectors according to the invention are those described by Feldman and Steg (1996; Semin Interv Cardiol 1:203-8) or Ohno et al. (1994; Science 265:781-4). Another preferred recombinant adenovirus according to this specific embodiment of the present invention is the human adenovirus type 2 or 5 (Ad 2 or Ad 5) or an adenovirus of animal origin (French patent application No. FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide-efficient delivery of genes into cells, and the transferred nucleic acids are stably integrated into the chromosomal DNA of the host.

Particularly preferred retroviruses for the preparation or construction of retroviral in vitro or in vivo gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., ((1989) Proc Natl Acad Sci USA 86:9079-83), Julan et al., (1992) J Gen. Virol 3:3251-3255 and Neda et al., ((1991) J Biol Chem 266:14143-6).

Yet another viral vector system that is contemplated by the invention consists of the adeno-associated virus (AAV). The adeno-associated virus is a naturally occurring defective virus that requires another virus, such as an adenovirus or a herpes virus, as a helper virus for efficient replication and a productive life cycle (Muzyczka et al., (1992) Curr Top Microbiol Immunol 158:97-129). It is also one of the few viruses that may integrate its DNA into non-dividing cells, and exhibits a high frequency of stable integration (Flotte et al., (1992) Am J Respir Cell Mol Biol 7:349-56; Samulski et al., (1989) J Virol 63:3822-8; McLaughlin et al., (1989) Am J Hum Genet 59:561-569). One advantageous feature of AAV derives from its reduced efficacy for transducing primary cells relative to transformed cells.

5) Delivery of the Recombinant Vectors

In order to effect expression of the polynucleotides of the invention, these constructs must be delivered into a cell. This delivery may be accomplished in vitro, as in laboratory procedures for transforming cell lines, or in vivo or ex vivo, as in the treatment of certain disease states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., (1973) Virology 54:536-9; Chen et al., (1987) Mol Cell Biol 7:2745-52), DEAE-dextran (Gopal, (1985) Mol Cell Biol 5:1188-90), electroporation (Tur-Kaspa et al., (1986) Mol Cell Biol 6:716-8; Potter et al., (1984) Proc Natl Acad Sci USA 81:7161-5.), direct microinjection (Harland et al., (1985) J Cell Biol 101:1094-9), DNA-loaded liposomes (Nicolau et al., (1982) Biochim Biophys Acta 721:185-90; Fraley et al., (1979) Proc Natl Acad Sci USA 76:3348-52), and receptor-mediated transfection (Wu and Wu, (1987) J Biol Chem 262:4429-32; Wu and Wu (1988) Biochemistry 27:887-92). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO 95/11307 (Institut Pasteur, INSERM, Université d'Ottawa) as well as in the articles of Tascon et al. (1996) Nature Medicine 2:888-892 and of Huygen et al. ((1996) Nat Med 2:893-8).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. ((1990) Curr Genet 17:97-103).

In a further embodiment, the polynucleotide of the invention may be entrapped in a liposome (Ghosh and Bacchawat, (1991) Targeted Diagn Ther 4:87-103; Wong et al., (1980) Gene 10:87-94; Nicolau et al., (1987) Methods Enzymot. 149:157-76). These liposomes may further be targeted to cells expressing LSR by incorporating leptin, triglycerides, or other known LSR ligands into the liposome membrane.

In a specific embodiment, the invention provides a composition for the in vivo production of a GMG-7A, GMG-7B, GMG-8, GMG-9, GMG-10, or GMG-11 polypeptide described herein. It comprises a naked polynucleotide operatively coding for this polypeptide, in solution in a physiologically acceptable carrier, and suitable for introduction into a tissue to cause cells of the tissue to express the said polypeptide.

The amount of vector to be injected to the desired host organism varies according to the site of injection. As an indicative dose, it will be injected between 0.1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired GMG-7A, GMG-7B, GMG-8, GMG-9, GMG-10, or GMG-11 polypeptide or the desired fragment thereof is reintroduced into the animal body in order to deliver the recombinant protein within the body either locally or systemically.

IV. Recombinant Cells of the Invention

Another object of the invention consists of host cells recombinant for, i.e., that have been transformed or transfected with one of the polynucleotides described herein, and more precisely a polynucleotide comprising a polynucleotide encoding a GMG-7A, GMG-7B, GMG-8, GMG-9, GMG-10, or GMG-11 polypeptide of the invention such as any one of those described in "Polynucleotides of the Invention". These polynucleotides can be present in cells as a result of transient or stable transfection. The invention includes host cells that are transformed (prokaryotic cells) or that are transfected (eukaryotic cells) with a recombinant vector such as any one of those described in "Recombinant Vectors of the Invention".

Generally, a recombinant host cell of the invention comprises at least one of the polynucleotides or the recombinant vectors of the invention that are described herein.

Preferred host cells used as recipients for the recombinant vectors of the invention are the following:

a) Prokaryotic host cells: *Escherichia coli* strains (I.E. DH5-x strain), *Bacillus subtilis, Salmonella typhimurium*, and strains from species like *Pseudomonas, Streptomyces* and *Staphylococcus*, and b) Eukaryotic host cells: HeLa cells (ATCC N°CCL2; N°CCL2.1; N°CCL2.2), Cv 1 cells (ATCC N°CCL70), COS cells (ATCC N°CRL1650; N°CRL1651), Sf-9 cells (ATCC N°CRL1711), C127 cells (ATCC N° CRL-1804), 3T3 (ATCC N° CRL-6361), CHO (ATCC N° CCL-61), human kidney 293 (ATCC N° 45504; N° CRL-1573), BHK (ECACC N° 84100501; N° 84111301), PLC cells, HepG2, and Hep3B.

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

In a preferred embodiment, recombinant protein expressed by cells that have been stably or transiently transfected with a recombinant vector such as any one of those described in "Recombinant Vectors of the Invention" is recovered from culture supernatant.

Alternatively, cells may be harvested (typically by centrifugation), disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skilled artisan.

Further, according to the invention, these recombinant cells can be created in vitro or in vivo in an animal, preferably a mammal, most preferably selected from the group consisting of mice, rats, dogs, pigs, sheep, cattle, and primates, not to include humans. Recombinant cells created in vitro can also be later surgically implanted in an animal, for example. Methods to create recombinant cells in vivo in animals are well-known in the art.

The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, the polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a polynucleotide construct, the polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a polynucleotide construct, the polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell it vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a polynucleotide construct that alters the expression of a targeted gene in a cell type in which the gene is not normally expressed. This occurs when a polynucleotide construct is inserted into the chromosomal DNA of the target cell, wherein the polynucleotide construct comprises: a) a targeting sequence; b) a regulatory sequence and/or coding sequence; and c) an unpaired splice-donor site, if necessary. Further included are polynucleotide constructs, as described above, wherein the construct further comprises a polynucleotide that encodes a polypeptide and is in-frame with the targeted endogenous gene after homologous recombination with chromosomal DNA.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos: WO96/29411, WO 94/12650; and scientific articles described by Koller et al., (1994) Annu Rev Immunol 10:705-730; the disclosures of each of which are incorporated by reference in their entireties).

The expression of GMG-7A, GMG-7B, GMG-8, GMG-9, GMG-10, or GMG-11 in mammalian, and typically human, cells may be rendered defective, or alternatively it may be enhanced, with the insertion of a GMG-7A, GMG-7B, GMG-8, GMG-9, GMG-10, or GMG-11 genomic or cDNA sequence with the replacement of the GMG-7A, GMG-7B, GMG-8, GMG-9, GMG-10, or GMG-11 gene counterpart in the genome of an animal cell by a GMG-7A, GMG-7B, GMG-8, GMG-9, GMG-10, or GMG-11 polynucleotide according to the invention. These genetic alterations may be generated by homologous recombination events using specific DNA constructs that have been previously described.

One kind of host cell that may be used are mammalian zygotes, such as murine zygotes. For example, murine zygotes may undergo microinjection with a purified DNA molecule of interest, for example a purified DNA molecule that has previously been adjusted to a concentration range from 1 ng/ml—for BAC inserts—3 ng/μl—for P1 bacteriophage inserts—in 10 mM Tris-HCl, pH 7.4, 250 μM EDTA containing 100 mM NaCl, 30 μM spermine, and 70 μM spermidine. When the DNA to be microinjected has a large size, polyamines and high salt concentrations can be used in order to avoid mechanical breakage of this DNA, as described by Schedl et al ((1993) Nature 362:258-61).

Any one of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC No. CRL-1821), ES-D3 (ATCC No. CRL-1934 and No. CRL-11632), YS001 (ATCC No. CRL-11776), 36.5 (ATCC No. CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells are primary embryonic fibroblasts that are established from tissue of day 13-day 14 embryos of virtually any mouse strain, that are maintained in culture, such as described by Abbondanzo et al. (1993; Methods Enzymol 225:803-23) and are inhibited in growth by irradiation, such as described by Robertson ((1987) Embryo-derived stem cell lines. In: E. J. Robertson Ed. Teratocarcinomas and embrionic stem cells: a practical approach. IRL Press, Oxford), or by the presence of an inhibitory concentration of LIF, such as described by Pease and Williams (1990; Exp Cell Res 190:209-11).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period. Cells are typically harvested by centrifugation, disrupted by physical or chemical means, and the resulting crude extract retained for further purification. Microbial cells employed in the expression of proteins can be disrupted by any convenient method, including freeze-thaw cycling, sonication, mechanical disruption, or use of cell lysing agents. Such methods are well known by the skilled artisan.

V. Transgenic Animals

The present invention also provides methods and compositions for the generation of non-human animals and plants that express the recombinant GMG-7A, GMG-7B, GMG-8, GMG-9, GMG-10, or GMG-11 polypeptides, of the present invention. The animals or plants can be transgenic, i.e. each of their cells contains a gene encoding a GMG-7A, GMG-7B, GMG-8, GMG-9, GMG-10, or GMG-11 polypeptide, or, alternatively, a polynucleotide encoding a GMG-7A, GMG-7B, GMG-8, GMG-9, GMG-10, or GMG-11 polypeptide can be introduced into somatic cells of the animal or plant, e.g. into mammary secretory epithelial cells of a mammal. In preferred embodiments, the non-human animal is a mammal such as a cow, sheep, goat, pig, or rabbit.

Methods of making transgenic animals such as mammals are well known to those of skill in the art, and any such method can be used in the present invention. Briefly, transgenic mammals can be produced, e.g., by transfecting a pluripotential stem cell such as an ES cell with a polynucleotide encoding a polypeptide of interest. Successfully transformed ES cells can then be introduced into an early stage embryo that is then implanted into the uterus of a mammal of the same species. In certain cases, the transformed ("transgenic") cells will comprise part of the germ line of the resulting animal, and adult animals comprising the transgenic cells in the germ line can then be mated to other animals, thereby eventually producing a population of transgenic animals that have the transgene in each of their cells, and which can stably transmit the transgene to each of their offspring. Other methods of introducing the polynucleotide can be used, for example introducing the polynucleotide encoding the polypeptide of interest into a fertilized egg or early stage embryo via microinjection. Alternatively, the transgene may be introduced into an animal by infection of zygotes with a retrovirus containing the transgene (Jaenisch, R. (1976) Proc. Natl. Acad. Sci. USA 73, 1260-1264). Methods of making transgenic mammals are described, e.g., in Wall et al. (1992) J Cell Biochem 1992 49:113-20; Hogan, et al. (1986) in Manipulating the mouse embryo. A Laboratory Manual. Cold Spring Harbor Laboratory Press, Cold Spring Harbor, N.Y.; in WO 91/08216, or in U.S. Pat. No. 4,736,866.

In a preferred method, the polynucleotides are microinjected into the fertilized oocyte. Typically, fertilized oocytes are microinjected using standard techniques, and then cultured in vitrountil a "pre-implantation embryo" is obtained. Such pre-implantation embryos preferably contain approximately 16 to 150 cells. Methods for culturing fertilized oocytes to the pre-implantation stage are described, e.g., by Gordon et al. ((1984) Methods in Enzymology, 101, 414); Hogan et al. ((1986) in Manipulating the mouse embryo. A Laboratory Manual. Cold Spring Harbor Laboratory Press, Cold Spring Harbor, N.Y.) (for the mouse embryo); Hammer et al. ((1985) Nature, 315, 680) (for rabbit and porcine embryos); Gandolfi et al. ((1987) J. Reprod. Fert. 81, 23-28); Rexroad et al. ((1988) J. Anim. Sci. 66, 947-953) (for ovine embryos); and Eyestone et al. ((1989) J. Reprod. Fert. 85, 715-720); Camous et al. ((1984) J. Reprod. Fert. 72, 779-785); and Heyman et al. ((1987) Theriogenology 27, 5968) (for bovine embryos); the disclosures of each of which are incorporated herein in their entireties. Pre-implantation embryos are then transferred to an appropriate female by standard methods to permit the birth of a transgenic or chimeric animal, depending upon the stage of development when the transgene is introduced.

As the frequency of transgene incorporation is often low, the detection of transgene integration in pre-implantation embryos is often desirable using any of the herein-described methods. Any of a number of methods can be used to detect the presence of a transgene in a pre-implantation embryo. For example, one or more cells may be removed from the pre-implantation embryo, and the presence or absence of the transgene in the removed cell or cells can be detected using any standard method e.g. PCR. Alternatively, the presence of a transgene can be detected in utero or post partum using standard methods.

In a particularly preferred embodiment of the present invention, transgenic mammals are generated that secrete recombinant GMG-7A, GMG-7B, GMG-8, GMG-9, GMG-10, or GMG-11 polypeptides in their milk. As the mammary gland is a highly efficient protein-producing organ, such methods can be used to produce protein concentrations in the gram per liter range, and often significantly more. Preferably, expression in the mammary gland is accomplished by operably linking the polynucleotide encoding the GMG-7A, GMG-7B, GMG-8, GMG-9, GMG-10, or GMG-11 polypeptide to a mammary gland specific promoter and, optionally, other regulatory elements. Suitable promoters and other elements include, but are not limited to, those derived from mammalian short and long WAP, alpha, beta, and kappa, casein, alpha and beta lactoglobulin, beta-CN 5' genes, as well as the the mouse mammary tumor virus (MMTV) promoter. Such promoters and other elements may be derived from any mammal, including, but not limited to, cows, goats, sheep, pigs, mice, rabbits, and guinea pigs. Promoter and other regulatory sequences, vectors, and other relevant teachings are provided, e.g., by Clark (1998) J Mammary Gland Biol Neoplasia 3:337-50; Jost et al. (1999) Nat Biotechnol 17:160-4; U.S. Pat. Nos. 5,994,616; 6,140,552; 6,013,857; Sohn et al. (1999) DNA Cell Biol. 18:845-52; Kim et al. (1999) J Biochem (Japan) 126:320-5; Soulier et al. (1999) Euro J Biochem 260:533-9; Zhang et al. (1997) Chin J Biotech 13:271-6; Rijnkels et al. (1998) Transgen Res 7:5-14; Korhonen et al. (1997) Euro J Biochem 245:482-9; Uusi-Oukari et al. (1997) Transgen Res 6:75-84; Hitchin et al. (1996) Prot Expr Purif 7:247-52; Platenburg et al. (1994) Transgen Res 3:99-108; Heng-Cherl et al. (1993) Animal Biotech. 4:89-107; and Christa et al. (2000) Euro J Biochem 267:1665-71; the entire disclosures of each of which is herein incorporated by reference.

In another embodiment, the polypeptides of the invention can be produced in milk by introducing polynucleotides encoding the polypeptides into somatic cells of the mammary gland in vivo, e.g. mammary secreting epithelial cells. For example, plasmid DNA can be infused through the nipple canal, e.g. in association with DEAE-dextran (see, e.g., Hens et al. (2000) Biochim. Biophys. Acta 1523:161-171), in association with a ligand that can lead to receptor-mediated endocytosis of the construct (see, e.g., Sobolev et al. (1998) 273:7928-33), or in a viral vector such as a retroviral vector, e.g. the Gibbon ape leukemia virus (see, e.g., Archer et al. (1994) PNAS 91:6840-6844). In any of these embodiments, the polynucleotide may be operably linked to a mammary gland specific promoter, as described above, or, alternatively, any strongly expressing promoter such as CMV or MoMLV LTR.

The suitability of any vector, promoter, regulatory element, etc. for use in the present invention can be assessed beforehand by transfecting cells such as mammary epithelial cells, e.g. MacT cells (bovine mammary epithelial cells) or GME cells (goat mammary epithelial cells), in vitro and assessing the efficiency of transfection and expression of the transgene in the cells.

For in vivo administration, the polynucleotides can be administered in any suitable formulation, at any of a range of concentrations (e.g. 1-500 µg/ml, preferably 50-100 µg/ml), at any volume (e.g. 1-100 ml, preferably 1 to 20 ml), and can be administered any number of times (e.g. 1, 2, 3, 5, or 10 times), at any frequency (e.g. every 1, 2, 3, 5, 10, or any number of days). Suitable concentrations, frequencies, modes of administration, etc. will depend upon the particular polynucleotide, vector, animal, etc., and can readily be determined by one of skill in the art.

In a preferred embodiment, a retroviral vector such as as Gibbon ape leukemia viral vector is used, as described in Archer et al. ((1994) PNAS 91:6840-6844). As retroviral infection typically requires cell division, cell division in the mammary glands can be stimulated in conjunction with the administration of the vector, e.g. using a factor such as estrodiol benzoate, progesterone, reserpine, or dexamethasone. Further, retroviral and other methods of infection can be facilitated using accessory compounds such as polybrene.

In any of the herein-described methods for obtaining GMG-7A, GMG-7B, GMG-8, GMG-9, GMG-10, or GMG-11 polypeptides from milk, the quantity of milk obtained, and thus the quantity of GMG-7A, GMG-7B, GMG-8, GMG-9, GMG-10, or GMG-11 polypeptides produced, can be enhanced using any standard method of lactation induction, e.g. using hexestrol, estrogen, and/or progesterone.

The polynucleotides used in such embodiments can either encode a full-length GMG-7A, GMG-7B, GMG-8, GMG-9, GMG-10, or GMG-11 polypeptide or a GMG-7A, GMG-7B, GMG-8, GMG-9, GMG-10, or GMG-11 fragment. Typically, the encoded polypeptide will include a signal sequence to ensure the secretion of the protein into the milk. Where a full length GMG-7A, GMG-7B, GMG-8, GMG-9, GMG-10, or GMG-11 sequence is used, the full length protein can, e.g., be isolated from milk and cleaved in vitro using a suitable protease. Alternatively, a second, protease-encoding polynucleotide can be introduced into the animal or into the mammary gland cells, whereby expression of the protease results in the cleavage of the GMG-7A, GMG-7B, GMG-8, GMG-9, GMG-10, or GMG-11 polypeptide in vivo, thereby allowing the direct isolation of GMG-7A, GMG-7B, GMG-8, GMG-9, GMG-10, or GMG-11 fragments from milk.

VI. Pharmaceutical or Physiologically Acceptable Compositions of the Invention

The GMG-7A, GMG-7B, GMG-8, GMG-9, GMG-10, or GMG-11 polypeptides of the invention can be administered to non-human animals and/or humans, alone or in pharmaceutical or physiologically acceptable compositions where they are mixed with suitable carriers or excipient(s). The pharmaceutical or physiologically acceptable composition is then provided at a therapeutically effective dose. A therapeutically effective dose refers to that amount of a GMG-7A, GMG-7B, GMG-8, GMG-9, GMG-10, or GMG-11 polypeptide sufficient to result in prevention or amelioration of symptoms or physiological status of metabolic-related diseases or disorders as determined by the methods described herein. A therapeutically effective dose can also refer to the amount of a GMG-7A, GMG-7B, GMG-8, GMG-9, GMG-10, or GMG-11 polypeptide necessary for a reduction in weight or a prevention of an increase in weight or prevention of an increase in the rate of weight gain in persons desiring this affect for cosmetic reasons. A therapeutically effective dosage of a GMG-7A, GMG-7B, GMG-8, GMG-9, GMG-10, or GMG-11 polypeptide of the invention is that dosage that is adequate to promote weight loss or weight gain with continued periodic use or administration. Techniques for formulation and administration of GMG-7A, GMG-7B, GMG-8, GMG-9, GMG-10, or GMG-11 polypeptides may be found in "Remington's Pharmaceutical Sciences," Mack Publishing Co., Easton, Pa., latest edition.

Other diseases or disorders that GMG-7A, GMG-7B, GMG-8, GMG-9, GMG-10, or GMG-11 polypeptides of the invention could be used to treat or prevent include, but are not limited to, obesity and obesity-related diseases and disorders such as obesity, impaired glucose tolerance, insulin resistance, atherosclerosis, atheromatous disease, heart disease, hypertension, stroke, Syndrome X, Non-Insulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, cancer-related weight loss, anorexia, and bulimia. The GMG-7A, GMG-7B, GMG-8, GMG-9, GMG-10, or GMG-11 polypeptides may also be used to enhance physical performance during work or exercise or enhance a feeling of general well-being. Physical performance activities include walking, running, jumping, lifting and/or climbing.

The GMG-7A, GMG-7B, GMG-8, GMG-9, GMG-10, or GMG-11 polypeptides or antagonists thereof may also be used to treat dyslexia, attention-deficit disorder (ADD), attention-deficit/hyperactivity disorder (ADHD), and psychiatric disorders such as schizophrenia by modulating fatty acid metabolism, more specifically, the production of certain long-chain polyunsaturated fatty acids.

It is expressly considered that the GMG-7A, GMG-7B, GMG-8, GMG-9, GMG-10, or GMG-11 polypeptides of the invention may be provided alone or in combination with other pharmaceutically or physiologically acceptable compounds. Other compounds useful for the treatment of obesity and other diseases and disorders are currently well-known in the art.

In a preferred embodiment, the GMG-7A, GMG-7B, GMG-8, GMG-9, GMG-10, or GMG-11 polypeptides are useful for, and used in, the treatment of insulin resistance and diabetes using methods described herein and known in the art. More particularly, a preferred embodiments relates to process for the therapeutic modification and regulation of glucose metabolism in an animal or human subject, which comprises administering to a subject in need of treatment (alternatively on a timed daily basis) GMG-7A, GMG-7B, GMG-8, GMG-9, GMG-10, or GMG-11 polypeptide (or polynucleotide encoding said polypeptide) in dosage amount and for a period sufficient to reduce plasma glucose levels in said animal or human subject.

Further preferred embodiments relate to methods for the prophylaxis or treatment of diabetes comprising administering to a subject in need of treatment (alternatively on a timed daily basis) a GMG-7A, GMG-7B, GMG-8, GMG-9, GMG-10, or GMG-11 polypeptide (or polynucleotide encoding said polypeptide) in dosage amount and for a period sufficient to reduce plasma glucose levels in said animal or human subject.

Routes of Administration

Suitable routes of administration include oral, nasal, rectal, transmucosal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. A particularly useful method of administering compounds for promoting weight loss involves surgical implantation, for example into the abdominal cavity of the recipient, of a device for delivering GMG-7A, GMG-7B, GMG-8, GMG-9, GMG-10, or GMG-11 polypeptides over an extended period of time. Other particularly preferred routes of administration are aerosol and depot formulation. Sustained release formulations, particularly depot, of the invented medicaments are expressly contemplated.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable acceptable carrier and at least one polypeptide that is a GMG-7A, GMG-7B, GMG-8, GMG-9, GMG-10, or GMG-11 polypeptide of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent additional strategies for protein stabilization may be employed.

The pharmaceutical or physiologically acceptable compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to increase leptin or lipoprotein uptake or binding in an in vitro system. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g. for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD5O and ED5O. Compounds that exhibit high therapeutic indices are preferred.

The data obtained from these cell culture assays and animal studies can be used in formulating a range of dosage for use in humans. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to maintain or prevent weight loss or gain, depending on the particular situation. Dosages necessary to achieve these effects will depend on individual characteristics and route of administration.

Dosage intervals can also be determined using the value for the minimum effective concentration. Compounds should be administered using a regimen that maintains plasma levels above the minimum effective concentration for 10-90% of the time, preferably between 30-90%; and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

A preferred dosage range for the amount of a GMG-7A, GM 7B, GMG-8, GMG-9, GMG-10, or GMG-11 polypeptide of the invention, which can be administered on a daily or regular basis to achieve desired results, including a reduction in levels of circulating plasma triglyceride-rich lipoproteins, range from 0.05-1.0 mg/kg body mass. A more preferred dosage range is from 0.1-5 mg/kg. A more preferred dose is 0.25-2.5 mg/kg. Of course, these daily dosages can be delivered or administered in small amounts periodically during the course of a day. It is noted that these dosage ranges are only preferred ranges and are not meant to be limiting to the invention.

VII. Methods of Treatment

The invention is drawn inter alia to methods of preventing or treating metabolic-related diseases and disorders comprising providing an individual in need of such treatment with a GMG-7A, GMG-7B, GMG-8, GMG-9, GMG-10, or GMG-11 polypeptide of the invention. Preferably, the GMG-7A, GMG-7B, GMG-8, GMG-9, GMG-10, or GMG-11 polypeptide has metabolic-related activity either in vitro or in vivo. Preferably the GMG-7A, GMG-7B, GMG-8, GMG-9, GMG-10, or GMG-11 polypeptide is provided to the individual in a pharmaceutical composition that is preferably taken orally. Preferably the individual is a mammal, and most preferably a human. In preferred embodiments, the metabolic-related disease or disorder is selected from the group consisting of atherosclerosis, cardiovascular disease, impaired glucose tolerance, insulin resistance, hypertension, stroke, Syndrome X, Type I diabetes, Type II diabetes and lipoatrophic diabetes. Diabetes-related complications to be treated by the methods of the invention include microangiopathic lesions, ocular lesions, retinopathy, neuropathy and renal lesions. Heart disease includes, but is not limited to, cardiac insufficiency, coronary insufficiency, and high blood pressure. Other metabolic-related disorders to be treated by compounds of the invention include hyperlipidemia, hypertriglyceridemia, and hyperuricemia. Yet other metabolic-related diseases or disorders of the invention include cachexia, wasting, AIDS-related weight loss, cancer-related weight loss, neoplasia-related weight loss, anorexia, and bulimia. In preferred embodiments, GMG-7A, GMG-7B, GMG-8, GMG-9, GMG-10, or GMG-11 polypeptides in pharmaceutical compositions are used to modulate body weight in healthy individuals for cosmetic reasons.

The invention also features a method of preventing or treating metabolic-related diseases and disorders comprising providing an individual in need of such treatment with a compound identified by assays of the invention (described in Section VI of the Preferred Embodiments of the Invention and in the Examples). Preferably these compounds antagonize or agonize effects of GMG-7A, GMG-7B, GMG-8, GMG-9, GMG-10, or GMG-11 polypeptides in cells in vitro, muscles ex vivo, or in animal models. Alternatively, these compounds agonize or antagonize the effects of GMG-7A, GMG-7B, GMG-8, GMG-9, GMG-10, or GMG-11 polypeptides on leptin and/or lipoprotein uptake and/or binding. Optionally, these compounds prevent the interaction, binding, or uptake of GMG-7A, GMG-7B, GMG-8, GMG-9, GMG-10, or GMG-11 polypeptides with LSR in vitro or in vivo. Preferably, the compound is provided to the individual in a pharmaceutical composition that is preferably taken orally. Preferably the individual is a mammal, and most preferably a human. In preferred embodiments, the metabolic-related disease or disorder is selected from the group consisting of obesity and metabolic-related diseases and disorders such as atherosclerosis, heart disease, insulin resistance, hypertension, stroke, Syndrome X Type I diabetes, Type II diabetes, and lipoatrophic diabetes. Diabetes-related complications to be treated by the methods of the invention include microangiopathic lesions, ocular lesions, retinopathy, neuropathy and renal lesions. Heart disease includes, but is not limited to, cardiac insufficiency, coronary insufficiency, and high blood pressure. Other metabolic-related disorders to be treated by compounds of the invention include hyperlipidemia, hypertriglyceridemia, and hyperuricemia.

In further preferred embodiments, the present invention of said pharmaceutical or physiologically acceptable composition can be used as a method to control blood glucose in some individuals, particularly those with Type I diabetes, Type II diabetes, or insulin resistance, in combination with insulin therapy.

In further preferred embodiments, the present invention of said pharmaceutical or physiologically acceptable composition can be used as a method to control body weight in some individuals, particularly those with Type I diabetes, Type II diabetes, or insulin resistance, in combination with insulin therapy.

In further preferred embodiments, the present invention of said pharmaceutical or physiologically acceptable composition can be used as a method to control blood glucose in some individuals, particularly those with Type I diabetes, Type II diabetes, or insulin resistance, alone, without combination of insulin therapy.

In further preferred embodiments, the present invention of said pharmaceutical or physiologically acceptable composition can be used as a method to control body weight in some individuals, particularly those with Type II diabetes or insulin resistance, alone, without combination of insulin therapy. In still a further preferred embodiment, the control of body weight is due in part or in whole to a decrease in mass of 1) subcutaneous adipose tissue and/or 2) viseral (omental) adipose tissue.

In a further preferred embodiment, the present invention may be used in complementary therapy, particularly in some individuals, particularly those with Type I diabetes, Type II diabetes, or insulin resistance, to improve their weight or glucose control in combination with an insulin secretagogue or an insulin sensitising agent. Preferably, the insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of some individuals, particularly those with Type I diabetes, Type II diabetes, or insulin resistance, alone, without an insulin secretagogue or an insulin sensitising agent.

In a further preferred embodiment, the present invention may be administered either concomitantly or concurrently, with the insulin secretagogue or insulin sensitising agent for example in the form of separate dosage units to be used simultaneously, separately or sequentially (either before or after the secretagogue or either before or after the sensitising agent). Accordingly, the present invention further provides for a composition of pharmaceutical or physiologically acceptable composition and an oral insulin secretagogue or insulin sensitising agent as a combined preparation for simultaneous, separate or sequential use for the improvement of body weight or glucose control in some individuals, particularly those with Type I diabetes, Type II diabetes, or insulin resistance.

In further preferred embodiments, the present invention of said pharmaceutical or physiologically acceptable composition further provides a method for the use as an insulin sensitiser.

In further preferred embodiments, the present invention of said pharmaceutical or physiologically acceptable composition can be used as a method to improve insulin sensitivity in some individuals, particularly those with Type I diabetes, Type II diabetes, or insulin resistance, in combination with insulin therapy.

In further preferred embodiments, the present invention of said pharmaceutical or physiologically acceptable composition can be used as a method to improve insulin sensitivity in some individuals, particularly those with Type II diabetes or insulin resistance, without insulin therapy.

In further preferred embodiments, the present invention of said pharmaceutical or physiologically acceptable composition further provides a method for the use as an inhibitor of the progression from impaired glucose tolerance to insulin resistance.

VII. Ligands Interacting with GMG-7A, GMG-7B, GMG-8, GMG-9, GMG-10, or GMG-11 Polypeptides For the purpose of the present invention, a Ligand means a molecule, such as a protein, a peptide, an antibody or any synthetic chemical compound capable of binding to a GMG-7A, GMG-7B, GMG-8, GMG-9, GMG-10, or GMG-11 polypeptide or one of its fragments or variants or to modulate the expression of the polynucleotide coding for GMG-7A, GMG-7B, GMG-8, GMG-9, GMG-10, or GMG-11 polypeptide or a fragment or variant thereof.

In the Ligand screening method according to the present invention, a biological sample or a defined molecule to be tested as a putative Ligand of a GMG-7A, GMG-7B, GMG-8, GMG-9, GMG-10, or GMG-11 polypeptide is brought into contact with the corresponding purified GMG-7A, GMG-7B, GMG-8, GMG-9, GMG-10, or GMG-11 polypeptide, for example the corresponding purified recombinant GMG-7A, GMG-7B, GMG-8, GMG-9, GMG-10, or GMG-11 polypeptide produced by a recombinant cell host as described herein, in order to form a complex between this protein and the putative Ligand molecule to be tested.

As an illustrative example, to study the interaction of a GMG-7A, GMG-7B, GMG-8, GMG-9, GMG-10, or GMG-11 polypeptide, or a fragment comprising a contiguous span of at least 6 amino acids, preferably at least 8 to 10 amino acids, more preferably at least 12, 15, 20, 25, 30, 40, 50, or 100 amino acids of a polypeptide selected from the group consisting of of SEQ ID NO: 2, 4, 6, 8, 10, and 12, with drugs or small molecules, such as molecules generated through combinatorial chemistry approaches, the microdialysis coupled to HPLC method described by Wang et al. (1997) or the affinity capillary electrophoresis method described by Bush et al. (1997), the disclosures of which are incorporated by reference, can be used.

In further methods, peptides, drugs, fatty acids, lipoproteins, or small molecules which interact with a GMG-7A, GMG-7B, GMG-8, GMG-9, GMG-10, or GMG-11 polypeptide, or a fragment comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NO: 2, 4, 6, 8, 10, or 12 may be identified using assays such as the following. The molecule to be tested for binding is labelled with a detectable label, such as a fluorescent, radioactive, or enzymatic tag and placed in contact with immobilized GMG-7A, GMG-7B, GMG-8, GMG-9, GMG-10, or GMG-11 polypeptide, or a fragment thereof under conditions that permit specific binding to occur. After removal of non-specifically bound molecules, bound molecules are detected using appropriate means.

Various candidate substances or molecules can be assayed for interaction with a GMG-7A, GMG-7B, GMG-8, GMG-9, GMG-10, or GMG-11 polypeptide. These substances or molecules include, without being limited to, natural or synthetic organic compounds or molecules of biological origin such as polypeptides. When the candidate substance or molecule comprises a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

A. Candidate Ligands Obtained by Affinity Chromatography.

Proteins or other molecules interacting with a GMG-7A, GMG-7B, GMG-8, GMG-9, GMG-10, or GMG-11 polypeptide, or a fragment thereof comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NO: 2, 4, 6, 8, 10, and 12, can also be found using affinity columns which contain the GMG-7A, GMG-7B, GMG-8, GMG-9, GMG-10, or GMG-11 polypeptide, or a fragment thereof. The GMG-7A, GMG-7B, GMG-8, GMG-9, GMG-10, or GMG-11 polypeptide, or a fragment thereof, may be attached to the column using conventional techniques including chemical coupling to a suitable column matrix such as agarose, Affi Gel®, or other matrices familiar to those of skill in art. In some embodiments of this method, the affinity column contains chimeric proteins in which the GMG-7A, GMG-7B, GMG-8, GMG-9, GMG-10, or GMG-11 polypeptide, or a fragment thereof, is fused to glutathion S transferase (GST). A mixture of cellular proteins or pool of expressed proteins as described above is applied to the affinity column. Proteins or other molecules interacting with the GMG-7A, GMG-7B, GMG-8, GMG-9, GMG-10, or GMG-11 polypeptide, or a fragment thereof, attached to the column can then be isolated and analyzed on 2-D electrophoresis gel as described in Ramunsen et al. (1997), the disclosure of which is incorporated by reference. Alternatively, the proteins retained on the affinity column can be purified by electrophoresis-based methods and sequenced. The same method can be used to isolate antibodies, to screen phage display products, or to screen phage display human antibodies.

B. Candidate Ligands Obtained by Optical Biosensor Methods

Proteins interacting with a GMG-7A, GMG-7B, GMG-8, GMG-9, GMG-10, or GMG-11 polypeptide, or a fragment comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NO: 2, 4, 6, 8, 10, or 12, can also be screened by using an Optical Biosensor as described in Edwards and Leatherbarrow (1997) and also in Szabo et al. (1995), the disclosures of which are incorporated by reference. This technique permits the detection of interactions between molecules in real time, without the need of labelled molecules. This technique is based on the surface plasmon resonance (SPR) phenomenon. Briefly, the candidate Ligand molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate Ligand molecules cause a change in the refraction index on the surface, which change is detected as a change in the SPR signal. For screening of candidate Ligand molecules or substances that are able to interact with the GMG-7A, GMG-7B, GMG-8, GMG-9, GMG-10, or GMG-11 polypeptide, or a fragment thereof, the GMG-7A, GMG-7B, GMG-8, GMG-9, GMG-10, or GMG-11 polypeptide, or a fragment thereof, is immobilized onto a surface. This surface comprises one side of a cell through which flows the candidate molecule to be assayed. The binding of the candidate molecule on the GMG-7A, GMG-7B, GMG-8, GMG-9, GMG-10, or GMG-11 polypeptide, or a fragment thereof, is detected as a change of the SPR signal. The candidate molecules tested may be proteins, peptides, carbohydrates, lipids, or small molecules generated by combinatorial chemistry. Screening of candidate ligands by optical biosensor methods may also be performed by immobilizing eukaryotic or prokaryotic cells or lipid vesicles exhibiting an endogenous or a recombinantly expressed GMG-7A, GMG-7B, GMG-8, GMG-9, GMG-10, or GMG-11 polypeptide at their surface.

The main advantage of the method is that it allows the determination of the association rate between the GMG-7A, GMG-7B, GMG-8, GMG-9, GMG-10, or GMG-11 polypeptide and molecules interacting with the GMG-7A, GMG-7B, GMG-8, GMG-9, GMG-10, or GMG-11 polypeptide. It is thus possible to select specifically Ligand molecules interacting with the GMG-7A, GMG-7B, GMG-8, GMG-9, GMG-10, or GMG-11 polypeptide, or a fragment thereof, through strong or conversely weak association constants.

C. Candidate Ligands Obtained Through a Two-Hybrid Screening Assay.

The yeast two-hybrid system is designed to study protein-protein interactions in vivo (Fields and Song, 1989), which disclosure is hereby incorporated by reference in its entirety, and relies upon the fusion of a bait protein to the DNA binding domain of the yeast Gal4 protein. This technique is also described in the U.S. Pat. No. 5,667,973 and the U.S. Pat. No. 5,283,173, the technical teachings of both patents being herein incorporated by reference.

The general procedure of library screening by the two-hybrid assay may be performed as described by Harper et al. (1993) or as described by Cho et al. (1998) or also Fromont-Racine et al. (1997), which disclosures are hereby incorporated by reference in their entireties.

The bait protein or polypeptide comprises, consists essentially of, or consists of a GMG-7A, GMG-7B, GMG-8, GMG-9, GMG-10, or GMG-11 polypeptide or a fragment thereof comprising a contiguous span of at least 6 amino acids, preferably at least 8 to 10 amino acids, more preferably at least 12, 15, 20, 25, 30, 40, 50, or 100 amino acids of a polypeptide selected from the group consisting of sequences of SEQ ID NO: 2, 4, 6, 8, 10, and 12.

More precisely, the nucleotide sequence encoding the GMG-7A, GMG-7B, GMG-8, GMG-9, GMG-10, or GMG-11 polypeptide or a fragment or variant thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "prey" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non-limiting example the two different yeast strains may be the following:

Y190, the phenotype of which is (MATa, Leu2-3, 112 ura3-12, trp1-901, his3-D200, ade2-101, gal4Dgal180D URA3 GAL-LacZ, LYS GAL-HIS3, cyh$^r$);

Y187, the phenotype of which is (MATa gal4 gal80 his3 trp1-901 ade2-101 ura3-52 leu2-3, -112 URA3 GAL-lac-Zmet$^-$), which is the opposite mating type of Y190.

Briefly, 20 µg of pAS2/GMG-7A, pAS2/GMG-7B, pAS2/GMG-8, pAS2/GMG-9, pAS2/GMG-10, or pAS2/GMG-11 and 20 µg of pACT-cDNA library are co-transformed into yeast strain Y190. The transformants are selected for growth on minimal media lacking histidine, leucine and tryptophan, but containing the histidine synthesis inhibitor 3-AT (50 nM). Positive colonies are screened for beta galactosidase by filter lift assay. The double positive colonies (Mis$^+$, beta-gal$^+$) are then grown on plates lacking histidine, leucine, but containing tryptophan and cycloheximide (10 mg/ml) to select for loss of pAS2/GMG-7A, pAS2/GMG-7B, pAS2/GMG-8, pAS2/GMG-9, pAS2/GMG-10, or pAS2/GMG-11 plasmids but retention of pACT-cDNA library plasmids. The resulting Y190 strains are mated with Y187 strains expressing GMG-7A, GMG-7B, GMG-8, GMG-9, GMG-10, or GMG-11 or non-related control polypeptides such as cyclophilin B, lamin, or SNF1, as Gal4 fusions as described by Harper et al. (1993) and by Bram et al. (1993), which disclosures are hereby incorporated by reference in their entireties, and screened for beta galactosidase by filter lift assay. Yeast clones that are beta gal-after mating with the control Gal4 fusions are considered false positives.

In another embodiment of the two-hybrid method according to the invention, interaction between the GMG-7A, GMG-7B, GMG-8, GMG-9, GMG-10, or GMG-11 polypeptide or a fragment or variant thereof with cellular proteins may be assessed using the Matchmaker Two Hybrid System 2 (Catalog No. K1604-1, Clontech). As described in the manual accompanying the kit, the disclosure of which is incorporated herein by reference, nucleic acids encoding the GMG-7A, GMG-7B, GMG-8, GMG-9, GMG-10, or GMG-11 polypeptide or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformants capable of growing on medium lacking histidine are screened for GAL4 dependent lacZ expression. Those cells that are positive in both the histidine selection and the lacZ assay contain interaction between GMG-7A, GMG-7B, GMG-8, GMG-9, GMG-10, or GMG-11 polypeptide and the protein or peptide encoded by the initially selected cDNA insert.

IX. Assays for Identifying Modulators of GMG-7A, GMG-7B, GMG-8, GMG-9, GMG-10, or GMG-11 Polypeptide Activity The invention features methods of screening for one or more compounds that modulate the activity of GMG-7A, GMG-7B, GMG-8, GMG-9, GMG-10, or GMG-11 in cells, which includes providing potential compounds to be tested to the cells. Exemplary assays that may be used are described in the Examples section. To these assays would be added compounds to be tested for their inhibitory or stimulatory activity as compared to the effects of GMG-7A, GMG-7B, GMG-8, GMG-9, GMG-10, or GMG-11 polypeptides alone. Other assays in which an effect is observed based on the addition of GMG-7A, GMG-7B, GMG-8, GMG-9, GMG-10, or GMG-11 polypeptides can also be used to screen for modulators of GMG-7A, GMG-7B, GMG-8, GMG-9, GMG-10, or GMG-11 polypeptide activity or effects of the presence of GMG-7A, GMG-7B, GMG-8, GMG-9, GMG-10, or GMG-11 polypeptides on cells. The essential step is to apply an unknown compound and then to monitor an assay for a change from what is seen when only GMG-7A, GMG-7B, GMG-8, GMG-9, GMG-10, or GMG-11 polypeptides are applied to the cell. A change is defined as something that is significantly different in the presence of the compound plus GMG-7A, GMG-7B, GMG-8, GMG-9, GMG-10, or GMG-11 polypeptide compared to GMG 7A, GMG-7B, GMG-8, GMG-9, GMG-10, or GMG-11 polypeptide alone. In this case, significantly different would be an "increase" or a "decrease" in a measurable effect of at least 25%, 30%, 35%, 40%, 45%, 50%, 55%, 60%, 65%, 70%, or 75%.

The term "modulation" as used herein refers to a measurable change in an activity. Examples include, but are not limited to, lipolysis stimulated receptor (LSR) modulation, leptin modulation, lipoprotein modulation, plasma FFA levels, FFA oxidation, TG levels, glucose levels, and weight. These effects can be in vitro or preferably in vivo. Modulation of an activity can be either an increase or a decrease in the activity. Thus, LSR activity can be increased or decreased, leptin activity can be increased or decreased, and lipoprotein activity can be increased or decreased. Similarly, FFA, TG, glucose levels and weight can be increased or decreased in vivo. Free Fatty Acid oxidation can be increased or decreased in vivo or ex vivo.

By "LSR" activity is meant expression of LSR on the surface of the cell, or in a particular conformation, as well as its ability to bind, uptake, and degrade leptin and lipoprotein. By "leptin" activity is meant its binding, uptake and degradation by LSR, as well as its transport across a blood brain barrier, and potentially these occurrences where LSR is not necessarily the mediating factor or the only mediating factor. Similarly, by "lipoprotein" activity is meant its binding, uptake and degradation by LSR, as well as these occurrences where LSR is not necessarily the mediating factor or the only mediating factor. Exemplary assays are provided in the Examples. These assay and other comparable assays can be used to determine/identify compounds that modulate GMG-7A, GMG-7, GMG-8, GMG-9, GMG-10, or GMG-11 polypeptide activity. In some cases it may be important to identify compounds that modulate some but not all of the GMG-7A, GMG-7B, GMG 8, GMG-9, GMG-10, or GMG-11 polypeptide activities, although preferably all activities are modified.

The term "increasing" as used herein refers to the ability of a compound to increase the activity of GMG-7A, GMG-7B, GMG-8, GMG-9, GMG-10, or GMG-11 polypeptides in some measurable way compared to the effect of GMG-7A, GMG-7B, GMG-8, GMG-9, GMG-10, or GMG-11 polypeptides in its absence. As a result of the presence of the compound leptin binding and/or uptake might increase, for example, as compared to controls in the presence of the GMG-7A, GMG-7B, GMG-8, GMG-9, GMG-10, or GMG-11 polypeptide alone. Preferably, an increase in activity is at least 25%, 30%, 35%, 40%, 45%, 50%, 55%, 60%, 65%, 70%, or 75% compared to the level of activity in the presence of the GMG-7A, GMG-7B, GMG-8, GMG-9, GMG-10, or GMG-11 polypeptide. Preferably, but not intended to be limiting, said GMG-7A, GMG-7B, GMG-8, GMG-9, GMG-10, or GMG-11 polypeptide is GMG-7A, GMG-7B, GMG-8, GMG-9, GMG-10, or GMG-11 polypeptide fragment comprising all or part of the C-terminal globular C1q homology domain.

Similarly, the term "decreasing" as used herein refers to the ability of a compound to decrease an activity in some measurable way compared to the effect of a GMG-7A, GMG-7B, GMG-8, GMG-9, GMG-10, or GMG-11 polypeptide in its absence. For example, the presence of the compound decreases the plasma concentrations of FFA, TG, and glucose in mice. Also as a result of the presence of a compound leptin binding and/or uptake might decrease, for example, as compared to controls in the presence of the GMG-7A, GMG-7B, GMG-8, GMG-9, GMG-10, or GMG-11 polypeptides alone. Preferably, an decrease in activity is at least 25%, 30%, 35%, 40%, 45%, 50%, 55%, 60%, 65%, 70%, or 75% as compared to the level of activity in the presence of the GMG-7A, GMG-7B, GMG-8, GMG-9, GMG-10, or GMG-11 polypeptides alone. Preferably, but not intended to be limiting, said GMG-7A, GMG-7B, GMG-8, GMG-9, GMG-10, or GMG-11 polypeptide is GMG-7A, GMG-7B, GMG-8, GMG-9, GMG-10, or GMG-11 polypeptide fragment comprising all or part of the C-terminal globular C1q homology domain.

The invention features a method for identifying a potential compound to decrease body mass in individuals in need of decreasing body mass comprising: a) contacting a cell with a GMG-7A, GMG-7B, GMG-8, GMG-9, GMG-10, or GMG-11 polypeptide and a candidate compound; b) detecting a result selected from the group consisting of LSR modulation, leptin modulation, increase in glucose uptake or oxidation, decrease in blood lipid or triglyceride levels, increase in lipoprotein binding, uptake or degradation; FFA oxidation increase; and c) wherein said result identifies said potential compound if said result differs from said result when said cell is contacted with the GMG 7A, GMG-7B, GMG-8, GMG-9, GMG-10, or GMG-11 polypeptide alone.

Alternatively, the invention features a method for identifying a potential compound to increase body mass in individuals in need of increasing body mass comprising: a) contacting a cell with a GMG-7A, GMG-7B, GMG-8, GMG-9, GMG-10, or GMG-11 polypeptide and a candidate compound; b) detecting a result selected from the group consisting of LSR modulation, leptin modulation, decrease in glucose uptake or oxidation, increase in blood lipid or triglyceride levels, decrease in lipoprotein binding, uptake or degradation; FFA oxidation decrease; and c) wherein said result identifies said potential compound if said result differs from said result when said cell is contacted with the GMG-7A, GMG-7B, GMG-8, GMG-9, GMG-10, or GMG-11 polypeptide alone.

In still other preferred embodiments, said potential compound is selected from the group consisting of peptides, peptide libraries, non-peptide libraries, peptoids, fatty acids, lipoproteins, medicaments, antibodies, small molecules, proteases and protease inhibitors.

X. Epitopes and Antibody Fusions

A preferred embodiment of the present invention is directed to eiptope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes. See, e.g., Geysen, et al. (1983) Proc Natl Acad Sci USA 81:39984002. It is particularly noted that although a particular epitope nay not be immunogenic, it is nonetheless useful since antibodies can be made in vitro to any epitope.

An epitope can comprise as few as 3 amino acids in a spatial conformation which is unique to the epitope. Generally an epitope consists of at least 6 such amino acids, and more often at least 8-10 such amino acids. In preferred embodiment, antigenic epitopes comprise a number of amino acids that is any integer between 3 and 50. Fragments which function as epitopes may be produced by any conventional means. See, e.g., Houghten, R. A., Proc Natl Acad Sci USA 82:5131-5135 (1985), further described in U.S. Pat. No. 4,631,211. Methods for determining the amino acids which make up an immunogenic epitope include x-ray crystallography, 2-dimensional nuclear magnetic resonance, and epitope mapping, e.g., the Pepscan method described by H. Mario Geysen et al. (1984); Proc. Natl. Acad. Sci. U.S.A. 81:3998-4002; PCT Publication No. WO 84/03564; and PCT Publication No. WO 84/03506. Another example is the algorithm of Jameson and Wolf, Comp. Appl. Biosci. 4:181-186 (1988) (said references incorporated by reference in their entireties). The Jameson-Wolf antigenic analysis, for example, may be performed using the computer program PROTEAN, using default parameters (Version 4.0 Windows, DNASTAR, Inc., 1228 South Park Street Madison, Wis.).

The epitope-bearing fragments of the present invention preferably comprise 6 to 50 amino acids (i.e. any integer between 6 and 50, inclusive) of a polypeptide of the present invention. Also, included in the present invention are antigenic fragments between the integers of 6 and the full-length sequence of the sequence listing. All combinations of sequences between the integers of 6 and the full-length sequence of a polypeptide of the present invention are included. The epitope-bearing fragments may be specified by either the number of contiguous amino acid residues (as a sub-genus) or by specific N-terminal and C-terminal positions (as species) as described above for the polypeptide fragments of the present invention. Any number of epitope-bearing fragments of the present invention may also be excluded in the same manner.

Antigenic epitopes are useful, for example, to raise antibodies, including monoclonal antibodies that specifically bind the epitope (See, Wilson et al., 1984; and Sutcliffe, J. G. et al., 1983). The antibodies are then used in various techniques such as diagnostic and tissue/cell identification techniques, as described herein, and in purification methods.

Similarly, immunogenic epitopes can be used to induce antibodies according to methods well known in the art (See, Sutcliffe et al., supra; Wilson et al., supra; Chow, M. et al.; (1985) and Bittle, F. J. et al., (1985). A preferred immunogenic epitope includes the polypeptides of the sequence listing. The immunogenic epitopes may be presented together with a carrier protein, such as an albumin, to an animal system (such as rabbit or mouse) if necessary. Immunogenic epitopes comprising as few as 8 to 10 amino acids have been shown to be sufficient to raise antibodies capable of binding to, at the very least, linear epitopes in a denatured polypeptide (e.g., in Western blotting.).

Epitope-bearing polypeptides of the present invention are used to induce antibodies according to methods well known in the art including, but not limited to, in vivo immunization, in vitro immunization, and phage display methods (See, e.g., Sutcliffe, et al., supra; Wilson, et al., supra, and Bittle, et al., 1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as—maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µgs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention including, but not limited to, polypeptides comprising an immunogenic or antigenic epitope can be fused to heterologous polypeptide sequences. For example, the polypeptides of the present invention may be fused with the constant region comprising portions of immunoglobulins (IgA, IgE, IgG, IgM), or portions of the constant region (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins (See, e.g., EPA 0,394,827; and Traunecker et al., 1988). Fusion proteins that have a disulfide-linked dimeric structure due to the IgG portion can also be more efficient in binding and neutralizing other molecules than monomeric polypeptides or fragments thereof alone (See, e.g., Fountoulakis et al., 1995). Nucleic acids encoding the above epitopes can also be recombined with a gene of interest as an epitope tag to aid in detection and purification of the expressed polypeptide.

Additional fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos. 5,605,793; 5,811,238; 5,834,252; 5,837,458; and Patten, P. A., et al., (1997); Harayama, S., (1998); Hansson, L. O., et al (1999); and Lorenzo, M. M. and Blasco, R., (1998). (Each of these documents are hereby incorporated by reference). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

Antibodies

The present invention further relates to antibodies and T-cell antigen receptors (TCR) that specifically bind the polypeptides, and more specifically, the epitopes of the polypeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies, which specifically bind the polypeptides of the present invention. The present invention further includes antibodies that are anti-idiotypic to the antibodies of the present invention.

The antibodies of the present invention may be monospecific, bispecific, and trispecific or have greater multi-specificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991); U.S. Pat. Nos. 5,573,920, 4,474,893, 5,601,819, 4,714,681, 4,925,648; Kostelny, S. A. et al. (1992).

Antibodies of the present invention may be described or specified in terms of the epitope(s) or epitope-bearing portion(s) of a polypeptide of the present invention, which are recognized or specifically bound by the antibody. In the case of proteins of the present invention secreted proteins, the antibodies may specifically bind a full-length protein encoded by a nucleic acid of the present invention, a mature protein (i.e., the protein generated by cleavage of the signal peptide) encoded by a nucleic acid of the present invention, a signal peptide encoded by a nucleic acid of the present invention, or any other polypeptide of the present invention. Therefore, the epitope(s) or epitope bearing polypeptide portion(s) may be specified as described herein, e.g., by N-terminal and C-terminal positions, by size in contiguous amino acid residues, or otherwise described herein. Antibodies that specifically bind any epitope or polypeptide of the present invention may also be excluded as individual species. Therefore, the present invention includes antibodies that specifically bind specified polypeptides of the present invention, and allows for the exclusion of the same.

Antibodies of the present invention may also be described or specified in terms of their cross-reactivity. Antibodies that do not specifically bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein, eg., using FASTDB and the parameters set forth herein) to a polypeptide of the present invention are also included in the present invention. Further included in the present invention are antibodies, which only bind polypeptides encoded by polynucleotides, which hybridize to a polynucleotide of the present invention under stringent hybridization conditions (as described herein). Antibodies of the present invention may also be described or specified in terms of their binding affinity. Preferred binding affinities include those with a dissociation constant or Kd value less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples (See, e.g., Harlow et al., 1988).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, e.g., Harlow et al. 1988); Hammerling, et al, 1981)

(said references incorporated by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle, which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995); Ames, R. S. et al. (1995); Kettleborough, C. A. et al. (1994); Persic, L. et al. (1997); Burton, D. R. et al. (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax, R. L. et al. (1992); and Sawai, H. et al. (1995); and Better, M. et al. (1988).

Examples of techniques which can be used to produce single-chain Fvs and antibodies include those described in U.S. Pat. Nos. 4,946,778 and 5,258,498; Huston et al. (1991); Shu, L. et al. (1993); and Skerra, A. et al. (1988). For some uses, including in vivo use of antibodies in humans and in vitro detection assays, it may be preferable to use chimeric, humanized, or human antibodies. Methods for producing chimeric antibodies are known in the art. See e.g., Morrison, (1985); Oi et al., (1986); Gillies, S. D. et al. (1989); and U.S. Pat. No. 5,807,715. Antibodies can be humanized using a variety of techniques including CDR-grafting (EP 0 23 9 400; WO 91/09967; U.S. Pat. Nos. 5,530,101; and 5,585,089), veneering or resurfacing, (EP 0 592 106; EP 0 519 596; Padlan E. A., 1991; Studnicka G. M. et al., 1994; Roguska M. A. et al., 1994), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741.

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art (See e.g., Harbor et al. supra; WO 93/21232; EP 0 439 095; Naramura, M. et al. 1994; U.S. Pat. No. 5,474,981; Gillies, S. O. et al., 1992; Fell, H. P. et al., 1991).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half-life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991); Zheng, X. X. et al. (1995); and Vil, H. et al. (1992).

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies, which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies that bind the ligand and prevent binding of the ligand to the receptor, as well as antibodies that bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998); Chen, Z. et al. (1998); Harrop, J. A. et al. (1998); Zhu, Z. et al. (1998); Yoon, D. Y. et al. (1998); Prat, M. et al. (1998) J.; Pitard, V. et al. (1997); Liautard, J. et al. (1997); Carlson, N. G. et al. (1997) J.; Taryman, R. E. et al. (1995); Muller, Y. A. et al. (1998); Bartunek, P. et al. (1996).

As discussed above, antibodies of the polypeptides of the invention can, in turn, be utilized to generate anti-idiotypic antibodies that "mimic" polypeptides of the invention using techniques well known to those skilled in the art (See, e.g. Greenspan and Bona (1989); and Nissinoff (1991). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and therby block its biological activity, The invention also concerns a purified or isolated antibody capable of specifically binding to a mutated full length or mature polypeptide of the present invention or to a fragment or variant thereof comprising an epitope of the mutated polypeptide. In another preferred embodiment, the present invention concerns an antibody capable of binding to a polypeptide comprising at least 10 consecutive amino acids of a polypeptide of the present invention and including at least one of the amino acids which can be encoded by the trait causing mutations.

Non-human animals or mammals, whether wild-type or transgenic, which express a different species of a polypeptide of the present invention than the one to which antibody binding is desired, and animals which do not express a polypeptide of the present invention (i.e. a knockout animal) are particularly useful for preparing antibodies. Gene knock out animals will recognize all or most of the exposed regions of a polypeptide of the present invention as foreign antigens, and therefore produce antibodies with a wider array of epitopes. Moreover, smaller polypeptides with only 10 to 30 amino acids may be useful in obtaining specific binding to any one of the polypeptides of the present invention. In addition, the humoral immune system of animals that produce a species of a polypeptide of the present invention that resembles the antigenic sequence will preferentially recognize the differences between the animal's native polypeptide species and the antigen sequence, and produce antibodies to these unique sites in the antigen sequence. Such a technique will be particularly useful in obtaining antibodies that specifically bind to any one of the polypeptides of the present invention.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labelled by any one of the radioactive, fluorescent or enzymatic labels known in the art.

Consequently, the invention is also directed to a method for detecting specifically the presence of a polypeptide of the present invention according to the invention in a biological sample, said method comprising the following steps:
a) obtaining a biological sample suspected of containing a polypeptide of the present invention;
b) contacting the biological sample with a polyclonal or monoclonal antibody that specifically binds a polypeptide of the present invention under conditions suitable for antigen-antibody binding; and
c) detecting the antigen-antibody complex formed.

The invention also concerns a diagnostic kit for detecting in vitro the presence of a polypeptide of the present invention in a biological sample, wherein said kit comprises:
a) a polyclonal or monoclonal antibody that specifically binds a polypeptide of the present invention, optionally labelled;
b) a reagent allowing the detection of the antigen-antibody complexes formed, said reagent carrying optionally a label, or being able to be recognized itself by a labelled reagent, more particularly in the case when the above-mentioned monoclonal or polyclonal antibody is not labelled by itself.

A. Monoclonal Antibody Production by Hybridoma Fusion

Monoclonal antibody to epitopes of any of the peptides identified and isolated as described can be prepared from murine hybridomas according to the classical method of Kohler, G. and Milstein, C., Nature 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., Meth Enzymol 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, New York. Section 21-2.

In a preferred embodiment, said monoclonal antibody is specific for a GMG-7A, GMG-7B, GMG-8, GMG-9, GMG-10, or GMG-11 polypeptide or biologically active fragment thereof, wherein said biological activity is selected from the group consisting of lipid partitioning, lipid metabolism, and insulin-like activity. Preferably, but not intented to be limiting, said GMG-7A, GMG-7B, GMG-8, GMG-9, GMG-10, or GMG-11 polypeptide fragment comprises all or part of the C-terminal globular C1q homology domain. In preferred embodiments, said polypeptide fragment comprises, consists essentially of, or consists of, at least 6 consecutive amino acids and not more than 710 consecutive amino acids of SEQ ID NO: 2; at least 6 and not more than 471 consecutive amino acids of SEQ ID NO: 4; at least 6 consecutive amino acids and not more than 201 consecutive amino acids of SEQ ID NO: 6; at least 6 and not more than 446 consecutive amino acids of SEQ ID NO: 8; at least 6 and not more than 296 consecutive amino acids of SEQ ID NO: 10; or at least 6 and not more than 205 consecutive amino acids of SEQ ID NO: 12.

B. Polyclonal Antibody Production by Immunization

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appear to be most reliable. An effective immunization protocol for rabbits can be found in Vaitukaitis, J. et al. J. Clin. Endocrinol. Metab. 33:988-991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12 □M). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

In a preferred embodiment, said polyclonal antibody is specific for a GMG-7A, GMG-7B, GMG-8, GMG-9, GMG-10, or GMG-11 polypeptide or biologically active fragment thereof, wherein said biological activity is selected from the group consisting of lipid partitioning, lipid metabolism, and insulin-like activity. Preferably, but not intended to be limiting, said GMG-7A, GMG-7B, GMG-8, GMG-9, GMG-10, or GMG-11 polypeptide fragment comprises all or part of the C-terminal globular C1q homology domain. In preferred embodiments, said polypeptide fragment comprises, consists essentially of, or consists of, at least 6 consecutive amino acids and not more than 710 consecutive amino acids of SEQ ID NO: 2; at least 6 and not more than 471 consecutive amino acids of SEQ ED NO: 4; at least 6 consecutive amino acids and not more than 201 consecutive amino acids of SEQ ID NO: 6; at least 6 and not more than 446 consecutive amino acids of SEQ ID NO: 8; at least 6 and not more than 296 consecutive amino acids of SEQ ID NO: 10; or at least 6 and not more than 205 consecutive amino acids of SEQ ID NO: 12.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Other characteristics and advantages of the invention are described in the Examples. These are meant to be exemplary only, and not to limit the invention in any way. Throughout this application, various publications, patents and published patent applications are cited. The disclosures of these publications, patents and published patent specifications referenced in this application are hereby incorporated by reference into the present disclosure.

EXAMPLES

The following Examples are provided for illustrative purposes and not as a means of limitation. One of ordinary skill in the art would be able to design equivalent assays and methods based on the disclosure herein all of which form part of the instant invention.

Example 1

Northern Analysis of GMG-7A, GMG-7B, GMG-8, GMG-9, GMG-10, or GMG-11 Expression

Analysis of GMG-7A, GMG-7B, GMG-8, GMG-9, GMG-10, or GMG-11 expression in different human tissues (adult and fetal) and cell lines, as well as mouse embryos in different stages of development, is accomplished by using poly A+ RNA blots purchased from Clontech (e.g. #7780-1, 7757-1, 7756-1, 7768-1 and 7763-1). Labeling of RNA probes is performed using the RNA Strip-EZ kit from Ambion as per manufacture's instructions. Hybridization of RNA probes to RNA blots is performed Ultrahyb hybridization solution (Ambion). Briefly, blots are prehybridized for 30 min at 58° C. (low-strigency) or 65° C. (high stringency). After adding the labelled probe ($2 \times 10^6$ cpm/ml), blots are hybridized overnight (14-24 hrs), and washed 2×20 min at 50° C. with 2×SSC/0.1% SDS (low stringency), 2×20 min at 58° C. with 1×SSC/0.1% SDS (medium stringency) and 2×20 min at 65° C. with 1×SSC/0.1% SDS (high stringency). After washings are completed blots are exposed on the phosphoimager (Molecular Dynamics) for 1-3 days.

Example 2

In Vitro Tests of Metabolic-related Activity

The activity of various preparations and various sequence variants of GMG-7A, GMG-7B, GMG-8, GMG-9, GMG-10, or GMG-11 polypeptides are assessed using various in vitro assays including those provided below. These assays are also exemplary of those that can be used to develop GMG-7A, GMG-7B, GMG-8, GMG-9, GMG-10, or GMG-11 polypeptide antagonists and agonists. To do that, the effect of GMG-7A, GMG-7B, GMG-8, GMG-9, GMG-10, or GMG-11 polypeptides in the above assays, e.g. on leptin and/or LSR activity, in the presence of the candidate molecules would be compared with the effect of GMG-7A, GMG-7B, GMG-8, GMG-9, GMG-10, or GMG-11 polypeptides in the assays in the absence of the candidate molecules. Since GMG-7A, GMG-7B, GMG-8, GMG-9, GMG-10, or GMG-11 polypeptides reduce body weight in mice on a high-cafeteria diet (Example 5), these assays also serve to identify candidate treatments for reducing (or increasing) body weight.

Liver Cell Line

Tests of efficacy of GMG-7A, GMG-7B, GMG-8, GMG-9, GMG-10, or GMG-11 polypeptides on LSR can be performed using liver cell lines, including for example, PLC, HepG2, Hep3B (human), Hepa 1-6, BPRCL (mouse), or MCA-RH777, MCA-RH8994 (rat).

BPRCL mouse liver cells (ATCC Repository) are plated at a density of 300,000 cells/well in 6-well plates (day 0) in DMEM (high glucose) containing glutamine and penicillin-streptomycin (Bihain & Yen, 1992). Media is changed on day 2. On day 3, the confluent monolayers are washed once with phosphate-buffered saline (PBS, pH 7.4) (2 mL/well). Cells are incubated at 37° C. for 30 min with increasing concentrations of recombinant GMG-7A, GMG-7B, GMC-8, GMG-9, GMG-10, or GMG-11 polypeptide or GMG-7A, GMG-7B, GMG-8, GMG-9, GMG-10, or GMG-11 polypeptide fragment in DMEM containing 0.2% (w/v) BSA, 5 mM Hepes, 2 mM $CaCl_2$, 3.7 g/L sodium bicarbonate, pH 7.5. Incubations are continued for 3 h at 37° C. after addition of 10 ng/mL $^{125}$I-mouse leptin (specific activity, 22100 cpm/ng). Monolayers are washed 2 times consecutively with PBS containing 0.2% BSA, followed by 1 wash with PBS/BSA, and then 2 times consecutively with PBS. Cells are lysed with 0.1 N NaOH containing 0.24 mM EDTA. Lysates are collected into tubes, and counted in a gamma-counter.

Blood Brain Barrier Model

The effect of GMG-3, GMG-4, Cluster 1, GMG-6A, or GMG-6B polypeptides on leptin transport in the brain can be determined using brain-derived cells. One method that is envisioned is to use the blood/brain barrier model described by Dehouck, et al (J Neurochem 54:1798-801, 1990; hereby incorporated herein by reference in its entirety including any figures, tables, or drawings) that uses a co-culture of brain capillary endothelial cells and astrocytes to test the effects of GMG-7A, GMG-7B, GMG-8, GMG-9, GMG-10, or GMG-11 polypeptides on leptin (or other molecules) transport via LSR or other receptors.

This assay would be an indicator of the potential effect of GMG-7A, GMG-7B, GMG-8, GMG-9, GMG-10, or GMG-11 polypeptides on leptin transport to the brain and could be used to screen GMG-7A, GMG-7B, GMG-8, GMG-9, GMG-10, or GMG-11 polypeptide variants for their ability to modulate leptin transport through LSR or other receptors in the brain. In addition, putative agonists and antagonists of the effect of GMG-7A, GMG-7B, GMG-8, GMG-9, GMG-10, or GMG-11 polypeptides on leptin transport through LSR or other receptors could also be screened using this assay. Increased transport of leptin across the blood/brain barrier would presumably increase its action as a satiety factor.

FACS Analysis of LSR Expression

The effect of GMG-7A, GMG-7B, GMG-8, GMG-9, GMG-10, or GMG-11 polypeptides on LSR can also be determined by measuring the level of LSR expression at the cell surface by flow surface cytometry, using anti-LSR antibodies and fluorescent secondary antibodies. Flow cytometry is a laser-based technology that is used to measure characteristics of biological particles. The underlying principle of flow cytometry is that light is scattered and fluorescence is emitted as light from the excitation source strikes the moving particles.

This is a high throughput assay that could be easily adapted to screen GMG-7A, GMG-7B, GMG-8, GMG-9, GMG-10, or GMG-11 polypeptides and variants as well as putative agonists or antagonists of GMG-7A, GMG-7B, GMG-8, GMG-9, GMG-10, or GMG-11 polypeptides. Two assays are provided below. The antibody, cell-line and GMG-7A, GMG-7B, GMG-8, GMG-9, GMG-10, or GMG-11 polypeptide analogs would vary depending on the experiment, but a human cell-line, human anti-LSR antibody and GMG-7A, GMG-7B, GMG-8, GMG-9, GMG-10, or GMG-11 polypeptide fragment could be used to screen for variants, agonists, and antagonists to be used to treat humans.

Assay 1

Cells are pretreated with either intact GMG-7A, GMG-7B, GMG-8, GMG-9, GMG-10, or GMG-11 polypeptide or GMG-7A, GMG-7B, GMG-8, GMG-9, GMG-10, or GMG-11 polypeptide fragment (or untreated) before harvesting and analysis by FACS. Cells are harvested using non-enzymatic dissociation solution (Sigma), and then are incubated for 1 h at 4° C. with a 1:200 dilution of anti-LSR 81B or an irrelevant anti-serum in PBS containing 1% (w/v) BSA. After washing twice with the same buffer, goat anti-rabbit FITC-conjugated antibody (Rockland, Gilbertsville, Pa.) is added to the cells, followed by a further incubation for 30 min at 4° C. After washing, the cells are fixed in 2% formalin. Flow cytometry analysis is done on a FACSCalibur cytometer (Becton-Dickinson, Franklin Lakes, N.J.).

Assay 2

Cells are cultured in T175 flasks according to manufacturer's instructions for 48 hours prior to analysis.

Cells are washed once with FACS buffer (1×PBS/2% FBS, filter sterilized), and manually scraped from the flask in 10 mLs of FACS buffer. The cell suspension is transferred to a 15 mL conical tube and centrifuged at 1200 rpm, 4° C. for 5 minutes. Supernatant is discarded and cells are resuspended in 10 mL FACS buffer chilled to 4° C. A cell count is performed and the cell density adjusted with FACS buffer to a concentration of $1 \times 10^6$ cells/mL. One milliliter of cell suspension was added to each well of a 48 well plate for analysis. Cells are centrifuged at 1200 rpm for 5 minutes at 4° C. Plates are checked to ensure that cells are pelleted, the supernatant is removed and cells resuspended by running plate over a vortex mixer. One milliliter of FACS buffer is added to each well, followed by centrifugation at 1200 rpm for 5 minutes at 4° C. This described cell washing was performed a total of 3 times.

Primary antibody, titered in screening experiments to determine proper working dilutions (for example 1:25, 1:50, 1:100, 1:200, 1:400, 1:500, 1:800, 1:1000, 1:2000, 1:4000, 1:5000, or 1:10000), is added to cells in a total volume of 50 μL FACS buffer. Plates are incubated for 1 h at 4° C. protected from light. Following incubation, cells are washed 3 times as directed above. Appropriate secondary antibody, titered in screening experiments to determine proper working dilutions (for example 1:25, 1:50, 1:100, 1:200, 1:400, 1:500, 1:800, 1:1000, 1:2000, 1:4000, 1:5000, or 1:10000), is added to cells in a total volume of 50 μL FACS buffer. Plates are incubated for 1 h at 4° C. protected from light. Following incubation, cells are washed 3 times as directed above. Upon final wash, cells are resuspended in 500 μL FACS buffer and transferred to a FACS acquisition tube. Samples are placed on ice protected from light and analyzed within 1 hour.

Cellular Binding and Uptake of GMG-7A, GMG-7B, GMG-8, GMG-9, GMG-10, or GMG-11 Polypeptides as Detected by Fluorescence Microscopy Fluorescein isothiocyanate (FITC) conjugation of GMG-7A, GMG-7B, GMG-8, GMG-9, GMG-10, or GMG-11 polypeptides: Purified GMG-7A, GMG-7B, GMG-8, GMG-9, GMG-10, or GMG-11 polypeptides at 1 mg/mL concentration are labelled with FITC using Sigma's FluoroTag FITC conjugation kit (Stock No. FITC-1). Protocol outlined in the Sigma Handbook for small-scale conjugation is followed for GMG-7A, GMG-7B, GMG-8, GMG-9, GMG-10, or GMG-11 polypeptide labeling.

Cell Culture: C2C12 mouse skeletal muscle cells (ATCC, Manassas, Va. CRL-1772) and Hepa-1-6 mouse hepatocytes (ATCC, Manassas, Va. CRL-1830) are seeded into 6 well plates at a cell density of $2 \times 10^5$ cells per well. C2C12 and Hepa-1-6 cells are cultured according to repository's instructions for 24-48 hours prior to analysis. Assay is performed when cells were 80% confluent.

FITC labelled GMG-7A, GMG-7B, GMG-8, GMG-9, GMG-10, or GMG-11 polypeptide cellular binding and uptake using microscopy: C2C12 and Hepa 1-6 cells are incubated in the presence/absence of antibody directed against human LSR (81B: N-terminal sequence of human LSR; does not cross react with mouse LSR and 93A: c-terminal sequence, cross reacts with mouse LSR) or an antiserum directed against gC1qr (953) for 1 hour at 37° C., 5% CO2. LSR antibodies are added to the media at a concentration of 2 µg/mL. The anti-gC1qr antiserum is added to the media at a volume of 2.5 µL undiluted serum (high concentration) or 1:100 dilution (low concentration). Following incubation with specified antibody, FITC-GMG-7A, -GMG-7B, -GMG-8, -GMG-9, -GMG-10, or -GMG-11 polypeptide (50 nM/mL) is added to each cell culture well. Cells are again incubated for 1 hour at 37° C., 5% CO2. Cells are washed 2× with PBS, cells are scraped from well into 1 mL of PBS. Cell suspension is transferred to an eppendorf tube and centrifuged at 1000 rpm for 2 minutes. Supernatant is removed and cells resuspended in 200 µL of PBS. Binding and uptake of FITC-GMG-7A, -GMG-7B, -GMG-8, -GMG-9, -GMG-10, or -GMG-11 polypeptide is analyzed by fluorescence microscopy under 40× magnification.

This assay may be useful for identifying agents that facilitate or prevent the uptake and/or binding of GMG-7A, GMG-7B, GMG-8, GMG-9, GMG-10, or GMG-11 polypeptides to cells.

Effect on LSR as a Lipoprotein Receptor

The effect of GMG-7A, GMG-7B, GMG-8, GMG-9, GMG-10, or GMG-11 polypeptide on the lipoprotein binding, internalizing and degrading activity of LSR can also be tested. Measurement of LSR as lipoprotein receptor is described in Bihain & Yen, ((1992) Biochemistry 31:4628-36; hereby incorporated herein in its entirety including any drawings, tables, or figures). The effect of GMG-7A, GMG-7B, GMG-8, GMG-9, GMG-10, or GMG-11 polypeptide on the lipoprotein binding, internalizing and degrading activity of LSR (or other receptors) can be compared with that of intact GMG-7A, GMG-7B, GMG-8, GMG-9, GMG-10, or GMG-11 polypeptide, with untreated cells as an additional control. This assay can also be used to screen for active and inhibitory variants of GMG-7A, GMG-7B, GMG-8, GMG-9, GMG-10, or GMG-11 polypeptide, as well as agonists and antagonists of metabolic-related activity.

Human liver PLC cells (ATCC Repository) are plated at a density of 300,000 cells/well in 6-well plates (day 0) in DMEM (high glucose) containing glutamine and penicillin-streptomycin (Bihain & Yen, 1992). Media is changed on day 2. On day 3, the confluent monolayers are washed once with phosphate-buffered saline (PBS, pH 7.4) (2 mL/well). Cells are incubated at 37° C. for 30 min with 10 ng/mL human recombinant leptin in DMEM containing 0.2% (w/v) BSA, 5 mM Hepes, 2 mM $CaCl_2$, 3.7 g/L sodium bicarbonate, pH 7.5, followed by another 30 min incubation at 37° C. with increasing concentrations of GMG-7A, GMG-7B, GMG-8, GMG-9, GMG-10, or GMG-11 polypeptide. Incubations are continued for 2 h at 37° C. after addition of 0.8 mM oleate and 20 µg/mL $^{125}$I-LDL. Monolayers are washed 2 times consecutively with PBS containing 0.2% BSA, followed by 1 wash with PBS/BSA, and then 2 times consecutively with PBS. The amounts of oleate-induced binding, uptake and degradation of $^{125}$I-LDL are measured as previously described (Bihain & Yen, 1992, supra). Results are shown as the mean of triplicate determinations.

GMG-7A, GMG-7B, GMG-8, GMG-9, GMG-10, or GMG-11 polypeptide leads to an increased activity of LSR as a lipoprotein receptor. The oleate-induced binding and uptake of LDL would be more affected by GMG-7A, GMG-7B, GMG-8, GMG-9, GMG-10, or GMG-11 polypeptide as compared to the degradation. This increased LSR activity would potentially result in an enhanced clearance of triglyceride-rich lipoproteins during the postprandial state. Thus, more dietary fat would be removed through the liver, rather than being deposited in the adipose tissue.

This assay could be used to determine the efficiency of a compound (or agonists or antagonists) to increase or decrease LSR activity (or lipoprotein uptake, binding and degradation through other receptors), and thus affect the rate of clearance of triglyceride-rich lipoproteins.

Effect on Muscle Differentiation

C2C12 cells (murine skeletal muscle cell line; ATCC CRL 1772, Rockville, Md.) are seeded sparsely (about 15-20%) in complete DMEM (w/glutamine, pen/strep, etc)+10% FCS. Two days later they become 80-90% confluent. At this time, the media is changed to DMEM+2% horse serum to allow differentiation. The media is changed daily. Abundant myotube formation occurs after 3-4 days of being in 2% horse serum, although the exact time course of C2C12 differentiation depends on how long they have been passaged and how they have been maintained, among other things.

To test the effect of the presence of GMG-7A, GMG-7B, GMG-8, GMG-9, GMG-10, or GMG-11 polypeptide on muscle differentiation, GMG-7A, GMG-7B, GMG-8, GMG-9, GMG-10, or GMG-11 polypeptide or polypeptide fragment (1 to 2.5 µg/mL) is added the day after seeding when the cells are still in DMEM w/10% FCS. Two days after plating the cells (one day after said GMG-7A, GMG-7B, GMG-8, GMG-9, GMG-10, or GMG-11 polypeptide or polypeptide fragment was first added), at about 80-90% confluency, the media is changed to DMEM+2% horse serum plus said GMG-7A, GMG-7B, GMG-8, GMG-9, GMG-10, or GMG-11 polypeptide or polypeptide fragment.

Effect on Muscle Cell Fatty Acid Oxidation

C2C12 cells are differentiated in the presence or absence of 2 µg/mL GMG-7A, GMG-7B, GMG-8, GMG-9, GMG-10, or GMG-11 polypeptide for 4 days. On day 4, oleate oxidation rates are determined by measuring conversion of 1-$^{14}$C-oleate (0.2 mM) to $^{14}CO_2$ for 90 min. This experiment can be used to screen for active polypeptides and peptides as well as agonists and antagonists or activators and inhibitors of GMG-7A, GMG-7B, GMG-8, GMG-9, GMG-10, or GMG-11 polypeptides.

The effect of GMG-7A, GMG-7B, GMG-8, GMG-9, GMG-10, or GMG-11 polypeptide or polypeptide fragment on the rate of oleate oxidation can be compared in differentiated C2C12 cells (murine skeletal muscle cells; ATCC, Manassas, Va. CRL-1772) and in a hepatocyte cell line (Hepal-6; ATCC, Manassas, Va. CRL-1830). Cultured cells are maintained according to manufacturer's instructions. The oleate oxidation assay is performed as previously described Muoio et al (1999) Biochem J 338; 783-791). Briefly, nearly confluent myocytes are kept in low serum differentiation media (DMEM, 2.5% Horse serum) for 4 days, at which time formation of myotubes became maximal. Hepatocytes are kept in the same DMEM medium supplemented with 10% FCS for 2 days. One hour prior to the experiment the media is removed and 1 mL of preincubation media (MEM, 2.5% Horse serum, 3 mM glucose, 4 mM Glutamine, 25 mM Hepes, 1% FFA free BSA, 0.25 mM Oleate, 5 µg/mL gentamycin) is added. At the start of the oxidation experiment $^{14}$C-Oleic acid (1 µCi/mL, American Radiolabelled Chemical Inc., St. Louis, Mo.) is added and cells are incubated for 90 min at 37° C. in the absence/presence of 2.5 µg/mL GMG-7A, GMG-7B, GMG-8, GMG-9, GMG-10, or GMG-11 polypeptide or polypeptide fragment. After the incubation period 0.75 mL of the media is removed and assayed for $^{14}$C-oxidation products as described below for the muscle FFA oxidation experiment.

Triglyceride and Protein Analysis Following Oleate Oxidation in Cultured Cells

Following transfer of media for oleate oxidation assay, cells are placed on ice. To determine triglyceride and protein content, cells are washed with 1 mL of 1×PBS to remove residual media. To each well 300 µL of cell dissociation solution (Sigma) is added and incubated at 37° C. for 10 min. Plates are tapped to loosen cells, and 0.5 mL of 1×PBS was added. The cell suspension is transferred to an eppendorf tube, each well is rinsed with an additional 0.5 mL of 1×PBS, and is transferred to appropriate eppendorf tube. Samples are centrifuged at 1000 rpm for 10 minutes at room temperature. Supernatant is discarded and 750 µL of 1×PBS/ 2% chaps is added to cell pellet. Cell suspension is vortexed and placed on ice for 1 hour. Samples are then centrifuged at 13000 rpm for 20 min at 4° C. Supernatants are transferred to new tube and frozen at −20° C. until analyzed. Quantitative measure of triglyceride level in each sample is determined using Sigma Diagnostics GPO-TRIDER enzymatic kit. The procedure outlined in the manual is adhered to, with the following exceptions: assay is performed in 48 well plate, 350 µL of sample volume was assayed, control blank consisted of 350 µL PBS/2% chaps, and standard contained 10 µL standard provide in kit plus 690 µL PBS/2% chaps. Analysis of samples is carried out on a Packard Spectra Count at a wavelength of 550 nm. Protein analysis is carried out on 25 µL of each supernatant sample using the BCA protein assay Pierce) following manufacturer's instructions. Analysis of samples is carried out on a Packard Spectra Count at a wavelength of 550 nm.

In Vitro Glucose Uptake by Muscle Cells

L6 Muscle cells are obtained from the European Culture Collection (Porton Down) and are used at passages 7-11. Cells are maintained in standard tissue culture medium DMEM, and glucose uptake is assessed using [$^3$H]-2-deoxyglucose (2DG) with or without GMG-7A, GMG-7B, GMG-8, GMG-9, GMG-10, or GMG-11 polypeptide fragment in the presence or absence of insulin ($10^{-8}$M) as has been previously described (Walker, P. S. et al. (1990) Glucose transport activity in L6 muscle cells is regulated by the coordinate control of subcellular glucose transporter distribution, biosynthesis, and mRNA transcription, JBC 265: 1516-1523; and Kilp, A. et al. (1992) Stimulation of hexose transport by metformin in L6 muscle cells in culture, Endocrinology 130:2535-2544, which disclosures are hereby incorporated by reference in their entireties). Uptake of 2DG is expressed as the percentage change compared with control (no added insulin or GMG-7A, GMG-7B, GMG-8, GMG-9, GMG-10, or GMG-11 polypeptide fragment). Values are presented as mean±SEM of sets of 4 wells per experiment. Differences between sets of wells are evaluated by Student's t test, probability values p<0.05 are considered to be significant.

Example 3

Effect of GMG-7A, GMG-7B, GMG-8, GMG-9, GMG-10, or GMG-11 Polypeptides on Mice Fed a High-Fat Diet Experiments are performed using approximately 6 week old C57Bl/6 mice (8 per group). All mice are housed individually. The mice are maintained on a high fat diet throughout each experiment. The high fat diet (cafeteria diet; D12331 from Research Diets, Inc.) has the following composition: protein kcal % 16, sucrose kcal % 26, and fat kcal % 58. The fat is primarily composed of coconut oil, hydrogenated.

After the mice are fed a high fat diet for 6 days, microosmotic pumps are inserted using isoflurane anesthesia, and are used to provide full-length GMG-7A, GMG-7B, GMG-8, GMG-9, GMG-10, or GMG-11 polypeptides, GMG-7A, GMG-7B, GMG-8, GMG-9, GMG-10, or GMG-11 polypeptide fragments, saline, and an irrelevant peptide to the mice subcutaneously (s.c.) for 18 days. GMG-7A, GMG-7B, GMG-8, GMG-9, GMG-10, or GMG-11 polypeptides are provided at doses of 100, 50, 25, and 2.5 µg/day and the irrelevant peptide is provided at 10 µg/day. Body weight is measured on the first, third and fifth day of the high fat diet, and then daily after the start of treatment. Final blood samples are taken by cardiac puncture and are used to determine triglyceride (TG), total cholesterol (TC), glucose, leptin, and insulin levels. The amount of food consumed per day is also determined for each group.

Example 4

Tests of Metabolic-related Activity in Humans

Tests of the efficacy of GMG-7A, GMG-7B, GMG-8, GMG-9, GMG-10, or GMG-11 polypeptides in humans are performed in accordance with a physician's recommendations and with established guidelines. The parameters tested in mice are also tested in humans (e.g. food intake, weight, TG, TC, glucose, insulin, leptin, FFA). It is expected that the physiological factors would show changes over the short term. Changes in weight gain might require a longer period of time. In addition, the diet would need to be carefully monitored. GMG-7A, GMG-7B, GMG-8, GMG-9, GMG-10, or GMG-11 polypeptides, preferably biologically active polypeptide fragments thereof, would be given in daily doses of about 6 mg protein per 70 kg person or about 10 mg per day. Other doses would also be tested, for instance 1 mg or 5 mg per day up to 20 mg, 50 mg, or 100 mg per day.

Example 5

Tests of Metabolic-related Activity in a Murine Lipoatrophic Diabetes Model

Previously, leptin was reported to reverse insulin resistance and diabetes mellitus in mice with congenital lipodystrophy (Shimomura et al. Nature 401:73-76 (1999); hereby incorporated herein in its entirety including any drawings, figures, or tables). Leptin was found to be less effective in a different lipodystrophic mouse model of lipoatrophic diabetes (Gavrilova et al Nature 403: 850 (2000); hereby incorporated herein in its entirety including any drawings, figures, or tables). The instant invention encompasses the use of GMG-7A, GMG-7B, GMG-8, GMG-9, GMG-10, or GMG-11 polypeptides for reducing the insulin resistance and hyperglycaemia in this model either alone or in combination with leptin, the leptin peptide (U.S. provisional application No. 60/155,506), or other compounds. Assays include that described previously in Gavrilova et al. ((2000) Diabetes 49:1910-6; (2000) Nature 403:850) using A-ZIP/F-1 mice, except that GMG-7A, GMG-7B, GMG-8, GMG-9, GMG-10, or GMG-11 polypeptides would be administered using the methods previously described in Example 3 (or Examples 6-8). The glucose and insulin levels of the mice would be tested, and the food intake and liver weight monitored, as well as other factors, such as leptin, FFA, and TG levels, typically measured in our experiments (see Example 3, above, or Examples 6-8).

Example 6

Effect of GMG-7A, GMG-7B, GMG-8, GMG-9, GMG-10, or GMG-11 Polypeptides on Plasma Free Fatty Acid in C57 BL/6 Mice The effect of GMG-7A, GMG-7B, GMG-8, GMG-9, GMG-10, or GMG-11 polypeptides on postprandial lipemia (PPL) in normal C57BL6/J mice is tested.

The mice used in this experiment are fasted for 2 hours prior to the experiment after which a baseline blood sample is taken. All blood samples are taken from the tail using EDTA coated capillary tubes (50 µL each time point). At time 0 (8:30 AM), a standard high fat meal (6 g butter, 6 g sunflower oil, 10 g nonfat dry milk, 10 g sucrose, 12 mL distilled water prepared fresh following Nb#6, JF, pg. 1) is given by gavage (vol.=1% of body weight) to all animals. Immediately following the high fat meal, 25 µg a GMG-7A, GMG-7B, GMG-8, GMG-9, GMG-10, or GMG-11 polypeptide is injected i.p. in 100 µL saline. The same dose (25 µg/mL in 100 µL) is again injected at 45 min and at 1 hr 45 min. Control animals are injected with saline (3×100 µL). Untreated and treated animals are handled in an alternating-mode.

Blood samples are taken in hourly intervals, and are immediately put on ice. Plasma is prepared by centrifugation following each time point. Plasma is kept at −20° C. and free fatty acids (FFA), triglycerides (TG) and glucose are determined within 24 hours using standard test kits (Sigma and Wako). Due to the limited amount of plasma available, glucose is determined in duplicate using pooled samples. For each time point, equal volumes of plasma from all 8 animals per treatment group are pooled.

Example 7

Effect of GMG-7A, GMG-7B, GMG-8, GMG-9, GMG-10, or GMG-11 Polypeptides on Plasma Leptin and Insulin in C57 BL/6 Mice The effect of GMG-7A, GMG-7B, GMG-8, GMG-9, GMG-10, or GMG-11 polypeptides on plasma leptin and insulin levels during postprandial lipemia (PPL) in normal C57BL6/J mice is tested. The experimental procedure is the same as that described in Example 6, except that blood was drawn only at 0, 2 and 4 hours to allow for greater blood samples needed for the determination of leptin and insulin by RIA.

Briefly, 16 mice are fasted for 2 hours prior to the experiment after which a baseline blood sample is taken. All blood samples are taken from the tail using EDTA coated capillary tubes (100 µL each time point). At time 0 (9:00 AM), a standard high fat meal (see Example 6) is given by gavage (vol.=1% of body weight) to all animals. Immediately following the high fat meal, 25 fig of a GMG-7A, GMG-7B, GMG-8, GMG-9, GMG-10, or GMG-11 polypeptide is injected i.p. in 100 µL saline. The same dose (25 µg in 100 µL) is again injected at 45 min and at 1 hr 45 min (treated group). Control animals are injected with saline (3×100 µL). Untreated and treated animals are handled in an alternating mode.

Blood samples are immediately put on ice and plasma is prepared by centrifugation following each time point. Plasma is kept at −20° C. and free fatty acids (FFA) are determined within 24 hours using a standard test kit (Wako). Leptin and Insulin are determined by RIA (ML-82K and SRI-13K, LINCO Research, Inc., St. Charles, Mo.) following the manufacturer's protocol; however, only 20 µL plasma is used. Each determination is done in duplicate. Due to the limited amount of plasma available, leptin and insulin are determined in 4 pools of 2 animals each in both treatment groups.

Example 8

Effect of GMG-7A, GMG-7B, GMG-8, GMG-9, GMG-10, or GMG-11 Polypeptides on Plasma FFA, TG and Glucose in C57 BL/6 Mice The effect of GMG-7A, GMG-7B, GMG-8, GMG-9, GMG-10, or GMG-11 polypeptides on plasma FFA, TG, glucose, leptin and insulin levels during postprandial lipemia (PPL) in normal C57BL6/J mice has been described. Weight loss resulting from GMG-7A, GMG-7B, GMG-8, GMG-9, GMG-10, or GMG-11 polypeptides (2.5 µg/day) given to normal C57BL6/J mice on a high fat diet has also been shown (Example 3).

The experimental procedure is similar to that described in Example 6. Briefly, 14 mice re fasted for 2 hours prior to the experiment after which a baseline blood sample is taken. All blood samples are taken from the tail using EDTA coated capillary tubes (50 µL each time point). At time 0 (9:00 AM), a standard high fat meal (see Example 6) is given by gavage (vol.=1% of body weight) to all animals. Immediately following the high fat meal, 4 mice are injected 25 µg of a GMG-7A, GMG-7B, GMG-8, GMG-9, GMG-10, or GMG-11 polypeptide i.p. in 100 µL saline. The same dose (25 µg in 100 µL) is again injected at 45 min and at 1 hr 45 min. A second treatment group receives 3 times 50 µg GMG-7A, GMG-7B, GMG-8, GMG-9, GMG-10, or GMG-11 polypeptide at the same intervals. Control animals are injected with saline (3×100 µL). Untreated and treated animals are handled in an alternating mode.

Blood samples are immediately put on ice. Plasma is prepared by centrifugation following each time point. Plasma is kept at −20° C. and free fatty acids (FFA), triglycerides (TG) and glucose are determined within 24 hours using standard test kits (Sigma and Wako).

Example 9

Effect of GMG-7A, GMG-7B, GMG-8, GM 9, GMG-10, or GMG-11 Polypeptides on FFA Following Epinephrine Injection In mice, plasma free fatty acids increase after intragastric administration of a high fat/sucrose test meal. These free fatty acids are mostly produced by the activity of lipolytic enzymes i.e. lipoprotein lipase (LPL) and hepatic lipase (HL). In this species, these enzymes are found in significant amounts both bound to endothelium and freely circulating in plasma. Another source of plasma free fatty acids is hormone sensitive lipase (HSL) that releases free fatty acids from adipose tissue after β-adrenergic stimulation. To test whether GMG-7A, GMG-7B, GMG-8, GMG-9, GMG-10, or GMG-11 polypeptides also regulate the metabolism of free fatty acid released by HSL, mice are injected with epinephrine.

Two groups of mice are given epinephrine (5 µg) by intraperitoneal injection. A treated group is injected with a GMG-7A, GMG-7B, GMG-8, GMG-9, GMG-10, or GMG-11 polypeptide (25 µg) one hour before and again together with epinephrine, while control animals receive saline. Plasma is isolated and free fatty acids and glucose are measured as described above (Example 8).

Example 10

Effect of GMG-7A GMG-7B, GMG-8, GMG-9, GMG-10, or GMG-11 Polypeptides on Muscle FFA Oxidation To investigate the effect of GMG-7A, GMG-7B, GMG-8, GMG-9, GMG-10, or GMG-11 polypeptides on muscle free fatty acid oxidation, intact hind limb muscles from C57BL/6J mice are isolated and FFA oxidation is measured using oleate as substrate (Clee, S. M. et al. Plasma and vessel wall lipoprotein lipase have different roles in atherosclerosis. J Lipid Res 41, 521-531 (2000); Muoio, D. M., Dohm, G. L., Tapscott, E. B. & Coleman, R. A. Leptin opposes insulin's effects on fatty acid partitioning in muscles isolated from obese ob/ob mice. Am J Physiol 276, E913-921 (1999)) Oleate oxidation in isolated muscle is measured as previously described (Cuendet et al (1976) J Clin Invest 58:1078-1088; Le Marchand-Brustel, Y., Jeanrenaud, B. & Freychet, P. Insulin binding and effects in isolated soleus muscle of lean and obese mice. Am J Physiol 234, E348-E358 (1978). Briefly, mice are sacrificed by cervical dislocation and soleus and EDL muscles are rapidly isolated from the hind limbs. The distal tendon of each muscle is tied to a piece of suture to facilitate transfer among different media. All incubations are carried out at 30° C. in 1.5 mL of Krebs-Henseleit bicarbonate buffer (118.6 mM NaCl, 4.76 mM KCl, 1.19 mM $KH_2PO_4$, 1.19 mM $MgSO_4$, 2.54 mM $CaCl_2$, 25 mM $NaHCO_3$, 10 mM Hepes, pH 7.4) supplemented with 4% FFA free bovine serum albumin (fraction V, RIA grade, Sigma) and 5 mM glucose (Sigma). The total concentration of oleate (Sigma) throughout the experiment is 0.25 mM. All media are oxygenated (95% $O_2$; 5% $CO_2$) prior to incubation. The gas mixture is hydrated throughout the experiment by bubbling through a gas washer (Kontes Inc., Vineland, N.J.).

Muscles are rinsed for 30 min in incubation media with oxygenation. The muscles are then transferred to fresh media (1.5 mL) and incubated at 30° C. in the presence of 1 µCi/mL [1-$^{14}$C] oleic acid (American Radiolabelled Chemicals). The incubation vials containing this media are sealed with a rubber septum from which a center well carrying a piece of Whatman paper (1.5 cm×11.5 cm) is suspended.

After an initial incubation period of 10 min with constant oxygenation, gas circulation is removed to close the system to the outside environment and the muscles are incubated for 90 min at 30° C. At the end of this period, 0.45 mL of Solvable (Packard Instruments, Meriden, Conn.) is injected onto the Whatman paper in the center well and oleate oxidation by the muscle is stopped by transferring the vial onto ice.

After 5 min, the muscle is removed from the medium, and an aliquot of 0.5 mL medium is also removed. The vials are closed again and 1 mL of 35% perchloric acid is injected with a syringe into the media by piercing through the rubber septum. The $CO_2$ released from the acidified media is collected by the Solvable in the center well. After a 90 min collection period at 30° C., the Whatman paper is removed from the center well and placed in scintillation vials containing 15 mL of scintillation fluid (HionicFlour, Packard Instruments, Meriden, Conn.). The amount of $^{14}$C radioactivity is quantitated by liquid scintillation counting. The rate of oleate oxidation is expressed as nmol oleate produced in 90 min/g muscle.

To test the effect of full-length GMG-7A, GMG-7B, GMG-8, GMG-9, GMG-10, or GMG-11 polypeptide or GMG-7A, GMG-7B, GMG-8, GMG-9, GMG-10, or GMG-11 polypeptide fragment on oleate oxidation, these proteins are added to the media at a final concentration of 2.5 µg/mL and maintained in the media throughout the procedure.

Example 11

Effect of GMG-7A, GMG-7B, GMG-8, GMG-9, GMG-10, or GMG-11 Polypeptides on Triglyceride in Muscle & Liver Isolated from Mice To determine whether the increased FFA oxidation induced by GMG-7A, GMG-7B, GMG-8, GMG-9, GMG-10, or GMG-11 polypeptides is also accompanied by increased FFA delivery into muscle or liver, the hindlimb muscle and liver triglyceride content is measured after the GMG-7A, GMG-7B, GMG-8, GMG-9, GMG-10, or GMG-11 polypeptide treatment of mice. Hind limb muscles as well as liver samples are removed from treated and untreated animals and the triglyceride and free fatty acid concentration is determined following a standard lipid extraction method (Shimabukuro, M. et al. Direct antidiabetic effect of leptin through triglyceride depletion of tissues. Proc Natl Acad Sci USA 94:4637-4641 (1997)) followed by TG and FFA analysis using standard test kits.

Example 12

Effect of GMG-7A, GMG-7B, GMG-8, GMG-9, GMG-10, or GMG-11 Polypeptides on FFA Following Intralipid Injection Two groups of mice are intravenously (tail vein) injected with 30 µL bolus of Intralipid-20% (Clintec) to generate a sudden rise in plasma FFAs, thus by-passing intestinal absorption. (Intralipid is an intravenous fat emulsion used in nutritional therapy). A treated group (GMG-7A, GMG-7B, GMG-8, GMG-9, GMG-10, or GMG-11 polypeptide-treated) is injected with a GMG-7A, GMG-7B, GMG-8, GMG-9, GMG-10, or GMG-11 polypeptide (25 µg) at 30 and 60 minutes before Intralipid is given, while control animals (0 control) received saline. Plasma is isolated and FFAs are measured as described previously. The effect of GMG-7A, GMG-7B, GMG-8, GMG-9, GMG-10, or GMG-11 polypeptides on the decay in plasma FFAs following the peak induced by Intralipid injection is then monitored.

Example 13

In Vitro Glucose Uptake by Muscle Cells

L6 Muscle cells are obtained from the European Culture Collection (Porton Down) and are used at passages 7-11. Cells are maintained in standard tissue culture medium DMEM, and glucose uptake is assessed using [$^3$H]-2-deoxyglucose (2DG) with or without GMG-7A, GMG-7B, GMG-8, GMG-9, GMG-10, or GMG-11 polypeptides in the presence or absence of insulin ($10^{-8}$ M) as has been previously described (Walker, P. S. et al. (1990) Glucose transport activity in L6 muscle cells is regulated by the coordinate control of subcellular glucose transporter distribution, biosynthesis, and mRNA transcription. JBC 265:1516-1523; and Kilp, A. et al. (1992) Stimulation of hexose transport by metformin in L6 muscle cells in culture, Endocrinology 130:2535-2544, which disclosures are hereby incorporated by reference in their entireties). Uptake of 2DG is expressed as the percentage change compared with control (no added insulin or GMG-7A, GMG-7B, GMG-8, GMG-9, GMG-10, or GMG-11). Values are presented as mean±SEM of sets of 4 wells per experiment. Differences between sets of wells are evaluated by Student's t test, probability values p<0.05 are considered to be significant.

Example 14

In Vivo Tests for Metabolic-related Activity in Rodent Diabetes Models

As metabolic profiles differ among various animal models of obesity and diabetes, analysis of multiple models is undertaken to separate the effects GMG-7A, GMG-7B, GMG-8, GMG-9, GMG-10, or GMG-11 polypeptides on hyperglycemia, hyperinsulinemia, hyperlipidemia and obesity. Mutations within colonies of laboratory animals and different sensitivities to dietary regimens have made the development of animal models with non-insulin dependent diabetes associated with obesity and insulin resistance possible. Genetic models such as db/db and ob/ob (See Diabetes, (1982) 31:1-6) in mice and fa/fa in zucker rats have been developed by the various laboratories for understanding the pathophysiology of disease and testing the efficacy of new antidiabetic compounds (Diabetes, (1983) 32:830-838; Annu Rep Sankyo Res Lab (1994) 46:1-57). The homozygous animals, C57 BL/KsJ-db/db mice developed by Jackson Laboratory, US, are obese, hyperglycemic, hyperinsulinemic and insulin resistant (J Clin Invest, (1990) 85:962-967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention are tested for blood sugar and triglycerides lowering activities. Zucker (fa/fa) rats are severely obese, hyperinsulinemic, and insulin resistant (Coleman, Diabetes 31:1, 1982; E. Shafrir, in Diabetes Mellitus; H. Riflin and D. Porte, Jr. Eds. (Elsevier Science Publishing Co., Inc., New York, ed. 4, 1990), pp. 299-340), and the fa/fa mutation may be the rat equivalent of the murine db mutation (Friedman et al., Cell 69:217-220, 1992; Truett et al., Proc Natl Acad Sci USA 88:7806, 1991). Tubby (tub/tub) mice are characterized by obesity, moderate insulin resistance and hyperinsulinemia without significant hyperglycemia (Coleman et al., J. Heredity 81:424, 1990).

Previously, leptin was reported to reverse insulin resistance and diabetes mellitus in mice with congenital lipodystrophy (Shimomura et al. Nature 401: 73-76 (1999). Leptin is found to be less effective in a different lipodystrophic mouse model of lipoatrophic diabetes (Gavrilova et al Nature 403: 850 (2000); hereby incorporated herein in its entirety including any drawings, figures, or tables).

The streptozotocin (STZ) model for chemically-induced diabetes is tested to examine the effects of hyperglycemia in the absence of obesity. STZ-treated animals are deficient in insulin and severely hyperglycemic (Coleman, Diabetes 31:1, 1982; E. Shafrir, in Diabetes Mellitus; H. Rifkin and D. Porte, Jr. Eds. (Elsevier Science Publishing Co., Inc., New York, ed. 4, 1990), pp. 299-340). The monosodium glutamate (MSG) model for chemically-induced obesity (Olney, Science 164:719, 1969; Cameron et al., Clin Exp Pharmacol Physiol 5:41, 1978), in which obesity is less severe than in the genetic models and develops without hyperphagia, hyperinsulinemia and insulin resistance, is also examined. Finally, a non-chemical, non-genetic model for induction of obesity includes feeding rodents a high fat/high carbohydrate (cafeteria diet) diet ad libitum.

The instant invention encompasses the use of GMG-7A, GMG-7B, GMG-8, GMG-9, GMG-10, or GMG-11 polypeptides for reducing the insulin resistance and hyperglycemia in any or all of the above rodent diabetes models or in humans with Type I or Type II diabetes or other prefered metabolic diseases described previously or models based on other mammals. In the compositions of the present invention the GMG-7A, GMG-7B, GMG-8, GMG-9, GMG-10, or GMG-11 polypeptides may, if desired, be associated with other compatible pharmacologically active antidiabetic agents such as insulin, leptin (U.S. provisional application No. 60/155,506), or troglitazone, either alone or in combination. Assays include that described previously in Gavrilova et al. ((2000) Diabetes 49:1910-6; (2000) Nature 403:850) using A-ZIP/F-1 mice, except that GMG-7A, GMG-7B, GMG-8, GMG-9, GMG-10, or GMG-11 polypeptides are administered intraperitoneally, subcutaneously, intramuscularly or intravenously. The glucose and insulin levels of the mice would be tested, and the food intake and liver weight monitored, as well as other factors, such as leptin, FFA, and TG levels, typically measured in our experiments.

In Vivo Assay for Anti-hyperglycemic Activity of GMG-7A, GMG-7B GMG-8, GMG-9, GMG-10, or GMG-11 Polypeptides Genetically altered obese diabetic mice (db/db) (male, 7-9 weeks old) are housed (7-9 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch Basic Glucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed by micro-osmotic pumps, inserted using isoflurane anesthesia, to provide GMG-7A, GMG-7B, GMG-8, GMG-9, GMG-10, or GMG-11 polypeptides, saline, and an irrelevant peptide to the mice subcutaneously (s.c.). Blood is sampled from the tail vein hourly for 4 hours and at 24, 30 h post-dosing and analyzed for blood glucose concentrations. Food is withdrawn from 0-4 h post dosing and reintroduced thereafter. Individual body weights and mean food consumption (each cage) are also measured after 24 h. Significant differences between groups (comparing GMG-7A, GMG-7B, GMG-8, GMG-9, GMG-10, or GMG-11 treated to saline-treated) are evaluated using Student t-test.

In Vivo Insulin Sensitivity Assay

In vivo insulin sensitivity is examined by utilizing two-step hyperinsulinemic-euglycemic clamps according to the following protocol. Rodents from any or all of the various models described in Example 2 are housed for at least a week prior to experimental procedures. Surgeries for the placement of jugular vein and carotid artery catheters are performed under sterile conditions using ketamine and xylazine (i.m.) anesthesia. After surgery, all rodents are allowed to regain consciousness and placed in individual cages. GMG-7A, GMG-7B, GMG-8, GMG-9, GMG-10, or GMG-11 polypeptides or vehicle is administered through the jugular vein after complete recovery and for the following two days. Sixteen hours after the last treatment, hyperinsulinemic-euglycemic clamps are performed. Rodents are placed in restrainers and a bolus of 4 μCi [3-$^3$H] glucose (NEN) is administered, followed by a continuous infusion of the tracer at a dose of 0.2 μCi/min (20 μl/min). Two hours after the start of the tracer infusion, 3 blood samples (0.3 ml each) are collected at 10 minute intervals (−20-0 min) for basal measurements. An insulin infusion is then started (5 mU/kg/min), and 100 μl blood samples are taken every 10 min. to monitor plasma glucose. A 30% glucose solution is infused using a second pump based on the plasma glucose levels in order to reach and maintain euglycemia. Once a steady state is established at 5 mU/kg/min insulin (stable glucose infusion rate and plasma glucose), 3 additional blood samples (0.3 ml each) are obtained for measurements of glucose, [3-$^3$H] glucose and insulin (100-120 min.). A higher dose of insulin (25 mU/kg/min.) is then administered and glucose infusion rates are adjusted for the second euglycemic clamp and blood samples are taken at min. 220-240. Glucose specific activity is determined in deproteinized plasma and the calculations of Rd and hepatic glucose output (HGO) are made, as described (Lang et al., Endocrinology 130:43, 1992). Plasma insulin levels at basal period and after 5 and 25 mU/kg/min. infusions are hen determined and compared between GMG-7A, GMG-7B, GMG-8, GMG-9, GMG-10, or GMG-11 treated and vehicle treated rodents.

Insulin regulation of glucose homeostasis has two major components; stimulation of peripheral glucose uptake and suppression of hepatic glucose output. Using tracer studies in the glucose clamps, it is possible to determine which portion of the insulin response is affected by the GMG-7A, GMG-7B, GMG-8, GMG-9, GMG-10, or GMG-11 polypeptides.

What is claimed is:

1. An isolated polypeptide selected from the group consisting of:
   a) a polypeptide comprising SEQ ID NO: 2;
   b) a polypeptide comprising amino acids 2-710 of SEQ ID NO: 2 and
   c) a polypeptide comprising SEQ ID NO: 2 or amino acids 2-710 of SEQ ID NO: 2 fused to a heterologous amino acid sequence, wherein the polypeptide of a) or b) or c) increases fatty acid oxidation in muscle cells.

2. A composition comprising a carrier and one or more of the polypeptides of claim 1.

3. The isolated polypeptide according to claim 1, wherein said polypeptide comprising SEQ ID NO: 2 or amino acids 2-710 of SEQ ID NO: 2 is fused to a heterologous amino acid sequence.

4. The isolated polypeptide according to claim 3, wherein said heterologous amino acid sequence is a tag sequence.

5. The isolated polypeptide according to claim 3, wherein said heterologous amino acid sequence is an Fc fragment.

6. The isolated polypeptide according to claim 1, wherein said polypeptide comprises amino acids 2-710 of SEQ ID NO: 2.

7. The isolated polypeptide according to claim 1, wherein said polypeptide comprises SEQ ID NO: 2.

8. The isolated polypeptide according to claim 1, wherein said heterologous amino acid sequence is a tag sequence and said polypeptide comprises SEQ ID NO: 2.

9. The isolated polypeptide according to claim 1, wherein said heterologous amino acid sequence is a tag sequence and said polypeptide comprises amino acids 2-710 of SEQ ID NO: 2.

10. The isolated polypeptide according to claim 1, wherein said heterologous amino acid sequence is an Fc fragment and said polypeptide comprises SEQ ID NO: 2.

11. The isolated polypeptide according to claim 1, wherein said heterologous amino acid sequence is an Fc fragment and said polypeptide comprises amino acids 2-710 of SEQ ID NO: 2.

12. The composition according to claim 2, wherein said one or more polypeptides comprises a heterologous amino acid sequence comprising a Fc fragment fused to a polypeptide comprising amino acids 2-710 of SEQ ID NO: 2.

13. The composition according to claim 2, wherein said one or more polypeptides comprises a heterologous amino acid sequence comprising a tag sequence fused to a polypeptide comprising amino acids 2-710 of SEQ ID NO: 2.

14. The composition according to claim 2, wherein said one or more polypeptides comprises a heterologous amino acid sequence comprising a Fc fragment fused to a polypeptide comprising SEQ ID NO: 2.

15. The composition according to claim 2, wherein said one or more polypeptides comprises a heterologous amino acid sequence comprising a Fc fragment fused to a polypeptide comprising amino acids 2-710 of SEQ ID NO: 2.

* * * * *